US006893845B1

(12) United States Patent
Huse

(10) Patent No.: US 6,893,845 B1
(45) Date of Patent: May 17, 2005

(54) SURFACE EXPRESSION LIBRARIES OF HETEROMERIC RECEPTORS

(75) Inventor: William D. Huse, Del Mar, CA (US)

(73) Assignee: Applied Molecular Evolution, Inc., San Diego, CA (US)

( * ) Notice: Subject to any disclaimer, the term of this patent is extended or adjusted under 35 U.S.C. 154(b) by 0 days.

(21) Appl. No.: 08/471,622

(22) Filed: Jun. 5, 1995

Related U.S. Application Data

(63) Continuation of application No. 08/349,131, filed on Dec. 2, 1994, now Pat. No. 5,871,974, which is a continuation of application No. 08/120,648, filed on Sep. 13, 1993, now abandoned, which is a continuation of application No. 07/767,136, filed on Sep. 27, 1991, now abandoned, which is a continuation-in-part of application No. 07/590,219, filed on Sep. 28, 1990, now abandoned.

(51) Int. Cl.[7] .................... C07K 14/705; C07K 19/00; C12N 15/62
(52) U.S. Cl. .................. 435/69.7; 435/7.1; 435/7.2; 435/172.3; 435/252.3; 435/320.1; 536/23.4
(58) Field of Search .................... 435/7.1, 7.2, 69.7, 435/172.3, 252.3, 320.1; 536/23.4

(56) References Cited

U.S. PATENT DOCUMENTS

| 5,223,409 A | 6/1993 | Ladner et al. ............. 435/69.7 |
| 5,270,163 A | 12/1993 | Gold et al. ..................... 435/6 |
| 5,403,484 A | 4/1995 | Ladner et al. ........... 435/235.1 |
| 5,427,908 A | 6/1995 | Dower et al. .................. 435/5 |
| 5,432,018 A | 7/1995 | Dower et al. .................. 435/5 |
| 5,698,417 A | 12/1997 | Robinson et al. |
| 5,698,435 A | 12/1997 | Robinson et al. |

FOREIGN PATENT DOCUMENTS

| WO | WO 87/02671 | 5/1987 |
| WO | WO 88/06630 | 9/1988 |
| WO | WO 92/01047 | 1/1992 |

OTHER PUBLICATIONS

Nakanishi, Molecular Diversity of Glutamate Receptors and Implications for Brain Function, Science 258:597–603, Oct. 1992.*
Zarmley & Smits (1989) Adv. Exp. Med. Biol. 251: 215–218.*
Barbas et al., "Assembly of Combinatorial Antibody Libraries on Phage Surfaces: The Gene III Site". *Proc. Natl. Acad. Sci. USA* 88:7978–7982 (1991).
Better et al., "*Escherichia coli* Secretion of an Active Chimeric Antibody Fragment". *Science* 240:1041–1043 (1988).
Cabilly et al. "Generation of Antibody Activity from Immunoglobulin Polypeptide Chains Produced in *Escherichia coli*". *Proc. Natl. Acad. Sci. USA* 81:3273–3277 (1984).

Caton, Andrew J. and Koprowski, Hilary, "Influenza Virus Hemaglutinin–Specific Antibodies Isolated from a Combinational Expression Library are Closely Related to the Immune Response of the Donor". *Proc. Natl. Acad. Sci. USA* 87:6450–6454 (1990).
Clackson et al., "Making Antibody Fragments Using Phage Display Libraries". *Nature* 352:624–628 (1991).
Cwirla et al., "Peptides on Phage: A Vast Library of Peptides for Identifying Ligands". *Proc. Natl. Acad. Sci. USA* 87:6378–6382 (1990).
Derbyshire et al., "A Simple and Efficient Procedure for Saturation Mutagenesis Using Mixed Oligodeoxynucleotides". *Gene* 46:145–152 (1986).
Devlin et al., "Random Peptide Libraries: A Source of Specific Protein Binding Molecules". *Science* 249:404–406 (1990).
Hellström et al. "Epitope Mapping and Use of Anti–Idiotypic Antibodies to the L6 Monoclonal Anticarcinoma Antibody". *Cancer Res.* 50:2449–2454 (1990).
Hoogenboom et al., "Multi–Subunit Proteins on the Surface of Filamentous Phage: Methodologies for Displaying Antibody (Fab) Heavy and Light Chains". *Nucleic Acids Res.* 19:4133–4137 (1991).
Huse et al., "Generation of a Large Combinatorial Library of the Immunoglobulin Repertoire on Phage Lamba". *Science* 246:1275–1281 (1989).
Kunkel et all, "Rapid and Efficient Site–Specific Mutagensis Without Phenotypic Selection". *Methods in Enzymology* 154:367–382 (1987).
Marvin et al., "Structure and Assembly of Filamentous Bacterial Viruses". *Nature* 253:19–23 (1975).
Parmley, Stephan F. and Smith, George P., "Filamentous Fusion Phage Cloning Vectors for the Study of Epitopes and Design of Vaccine". *Adv. Exp. Med. Biol.* 251:215–218 (1989).
Parmley, Stephen F. and Smith, George P., "Antibody–selectable Filamentous fd Phage Vectors: Affinity Purification of Target Genes". *Gene* 73:305–318 (1988).
Plückthun, A. "Antibodies from *Escherichia coli*". *Nature* 347:497–498 (1990).
Reidhaar–Olson et al, "Combinatorial Cassette Mutagenesis as a Probe of the Informational Content of Protein Sequences". *Science* 241:53–57 (1988).
Roberts et al., "Generation of an Antibody with Enhanced Affinity and Specificity for its Antigen by Protein Engineering". *Nature* 328:731–734 (1987).

(Continued)

*Primary Examiner*—John D. Ulm
(74) *Attorney, Agent, or Firm*—McDermott, Will & Emery

(57) ABSTRACT

The invention is directed to a composition of matter consisiting of a plurality of procaryotic cells. The plurality of procaryotic cells contain diverse combinations of first and second DNA sequences encoding first and second polypeptides which form a heteromeric receptor exhibiting binding activity toward a preselected molecule. The heteromeric receptors being expressed on the surface of filamentous bacteriophage.

34 Claims, 16 Drawing Sheets

OTHER PUBLICATIONS

Sastry et al., "Cloning of the Immunological Repertoire in *Escherichia coli* for Generation of Monoclonal Catalytic Antibodies: Construction of a Heavy Chain Variable Region–Specific cDNA Library". *Proc. Natl. Sci. USA* 86:5728–5732 (1989).

Scott et al., "Searching for Peptide Ligands with an Epitope Library". *Science* 249:386–390 (1990).

Skerra, Arne and Plückthun, Andreas, "Assembly of a Functional Immunoglobulin $F_v$ Fragment in *Escherichia coli*". *Science* 240:1038–1041 (1988).

Smith, George, P., "Filamentous Fusion Phage: Novel Expression Vectors That Display Cloned Antigens on the Virion Surface". *Science* 228:1315–1317 (1985).

Ward et al. "Binding Activities of a Repertoire of Single Immunoglobulin Variable Domains Secreted from *Escherichia coli*". *Nature* 341:544–546 (1989).

* cited by examiner

FIG. 2A

```
      |   1        |  10        |  20        |  30        |  40        |  50        |  60
3001  GGCTTAACTC  AATTCTTGTG  GGTTATCTCT  CTGATATTAG  CGCTCAATTA  CCCTCTGACT  3060
3061  TTGTTCAGGG  TGTTCAGTTA  ATTCTCCCGT  CTAATGCGCT  TCCCTGTTTT  TATGTTATTC  3120
3121  TCTCTGTAAA  GGCTGCTATT  TTCATTTTTG  ACGTTAAACA  AAAAATCGTT  TCTTATTTGG  3180
3181  ATTGGGATAA  ATAATATGGC  TGTTTATTTT  GTAACTGGCA  AATTAGGCTC  TGGAAAGACG  3240
3241  CTCGTTAGCG  TTGGTAAGAT  TCAGGATAAA  ATTGTAGCTG  GGTGCAAAAT  AGCAACTAAT  3300
3301  CTTGATTTAA  GGCTTCAAAA  CCTCCCGCAA  GTCGGGAGGT  TCGCTAAAAC  GCCTCGCGTT  3360
3361  CTTAGAATAC  CGGATAAGCC  TTCTATATCT  GATTTGCTTG  CTATTGGGCG  CGGTAATGAT  3420
3421  TCCTACGATG  AAAATAAAAA  CGGCTTGCTT  GTTCTCGATG  AGTGCGGTAC  TTGGTTTAAT  3480
3481  ACCCGTTCTT  GGAATGATAA  GGAAAGACAG  CCGATTATTG  ATTGGTTTCT  ACATGCTCGT  3540
3541  AAATTAGGAT  GGGATATTAT  TTTTCTTGTT  CAGGACTTAT  CTATTGTTGA  TAAACAGGCG  3600
3601  CGTTCTGCAT  TAGCTGAACA  TGTTGTTTAT  TGTCGTCGTC  TGGACAGAAT  TACTTTACCT  3660
3661  TTTGTCGGTA  CTTTATATTC  TCTTATTACT  GGCTCGAAAA  TGCCTCTGCC  TAAATTACAT  3720
3721  GTTGGCGTTG  TTAAATATGG  CGATTCTCAA  TTAAGCCCTA  CTGTTGAGCG  TTGGCTTTAT  3780
3781  ACTGGTAAGA  ATTTGTATAA  CGCATATGAT  ACTAAACAGG  CTTTTTCTAG  TAATTATGAT  3840
3841  TCCGGTGTTT  ATTCTTATTT  AACGCCTTAT  TTATCACACG  GTCGGTATTT  CAAACCATTA  3900
3901  AATTTAGGTC  AGAAGATGAA  GCTTACTAAA  ATATATTTGA  AAAAGTTTTC  ACGCGTTCTT  3960
3961  TGTCTTGCGA  TTGGATTTGC  ATCAGCATTT  ACATATAGTT  ATATAACCCA  ACCTAAGCCG  4020
4021  GAGGTTAAAA  AGGTAGTCTC  TCAGACCTAT  GATTTTGATA  AATTCACTAT  TGACTCTTCT  4080
4081  CAGCGTCTTA  ATCTAAGCTA  TCGCTATGTT  TTCAAGGATT  CTAAGGGAAA  ATTAATTAAT  4140
4141  AGCGACGATT  TACAGAAGCA  AGGTTATTCA  CTCACATATA  TTGATTTATG  TACTGTTTCC  4200
4201  ATTAAAAAAG  GTAATTCAAA  TGAAATTGTT  AAATGTAATT  AATTTTGTTT  TCTTGATGTT  4260
4261  TGTTTCATCA  TCTTCTTTTG  CTCAGGTAAT  TGAAATGAAT  AATTCGCCTC  TGCGCGATTT  4320
4321  TGTAACTTGG  TATTCAAAGC  AATCAGGCGA  ATCCGTTATT  GTTTCTCCCG  ATGTAAAAGG  4380
4381  TACTGTTACT  GTATATTCAT  CTGACGTTAA  ACCTGAAAAT  CTACGCAATT  TCTTTATTTC  4440
4441  TGTTTTACGT  GCTAATAATT  TTGATATGGT  TGGTTCAATT  CCTTCCATAA  TTCAGAAGTA  4500
4501  TAATCCAAAC  AATCAGGATT  ATATTGATGA  ATTGCCATCA  TCTGATAATC  AGGAATATGA  4560
4561  TGATAATTCC  GCTCCTTCTG  GTGGTTTCTT  TGTTCCGCAA  AATGATAATG  TTACTCAAAC  4620
4621  TTTTAAAATT  AATAACGTTC  GGGCAAAGGA  TTTAATACGA  GTTGTCGAAT  TGTTTGTAAA  4680
4681  GTCTAATACT  TCTAAATCCT  CAAATGTATT  ATCTATTGAC  GGCTCTAATC  TATTAGTTGT  4740
4741  TAGTGCACCT  AAAGATATTT  TAGATAACCT  TCCTCAATTC  CTTTCTACTG  TTGATTTGCC  4800
4801  AACTGACCAG  ATATTGATTG  AGGGTTTGAT  ATTTGAGGTT  CAGCAAGGTG  ATGCTTTAGA  4860
4861  TTTTTCATTT  GCTGCTGGCT  CTCAGCGTGG  CACTGTTGCA  GGCGGTGTTA  ATACTGACCG  4920
4921  CCTCACCTCT  GTTTTATCTT  CTGCTGGTGG  TTCGTTCGGT  ATTTTTAATG  GCGATGTTTT  4980
4981  AGGGCTATCA  GTTCGCGCAT  TAAAGACTAA  TAGCCATTCA  AAAATATTGT  CTGTGCCACG  5040
5041  TATTCTTACG  CTTTCAGGTC  AGAAGGGTTC  TATCTCTGTT  GGCCAGAATG  TCCCTTTTAT  5100
5101  TACTGGTCGT  GTGACTGGTG  AATCTGCCAA  TGTAAATAAT  CCATTTCAGA  CGATTGAGCG  5160
5161  TCAAAATGTA  GGTATTTCCA  TGAGCGTTTT  TCCTGTTGCA  ATGGCTGGCG  GTAATATTGT  5220
5221  TCTGGATATT  ACCAGCAAGG  CCGATAGTTT  GAGTTCTTCT  ACTCAGGCAA  GTGATGTTAT  5280
5281  TACTAATCAA  AGAAGTATTG  CTACAACGGT  TAATTTGCGT  GATGGACAGA  CTCTTTTACT  5340
5341  CGGTGGCCTC  ACTGATTATA  AAAACACTTC  TCAAGATTCT  GGCGTACCGT  TCCTGTCTAA  5400
5401  AATCCCTTTA  ATCGGCCTCC  TGTTTAGCTC  CCGCTCTGAT  TCCAACGAGG  AAAGCACGTT  5460
5461  ATACGTGCTC  GTCAAAGCAA  CCATAGTACG  CGCCCTGTAG  CGGCGCATTA  AGCGCGGCGG  5520
5521  GTGTGGTGGT  TACGCGCAGC  GTGACCGCTA  CACTTGCCAG  CGCCCTAGCG  CCCGCTCCTT  5580
5581  TCGCTTTCTT  CCCTTCCTTT  CTCGCCACGT  TCGCCGGCTT  TCCCCGTCAA  GCTCTAAATC  5640
5641  GGGGGCTCCC  TTTAGGGTTC  CGATTTAGTG  CTTTACGGCA  CCTCGACCCC  AAAAAACTTG  5700
5701  ATTTGGGTGA  TGGTTCACGT  AGTGGGCCAT  CGCCCTGATA  GACGGTTTTT  CGCCCTTTGA  5760
5761  CGTTGGAGTC  CACGTTCTTT  AATAGTGGAC  TCTTGTTCCA  AACTGGAACA  ACACTCAACC  5820
5821  CTATCTCGGG  CTATTCTTTT  GATTTATAAG  GGATTTTGCC  GATTTCGGAA  CCACCATCAA  5880
5881  ACAGGATTTT  CGCCTGCTGG  GGCAAACCAG  CGTGGACCGC  TTGCTGCAAC  TCTCTCAGGG  5940
5941  CCAGGCGGTG  AAGGGCAATC  AGCTGTTGCC  CGTCTCGCTG  GTGAAAAGAA  AAACCACCCT  6000
      |  10        |  20        |  30        |  40        |  50        |  60
```

FIG. 2B

```
          |   10      |   20      |   30      |   40      |   50      |   60
6001  GGCGCCCAAT ACGCAAACCG CCTCTCCCCG CGCGTTGGCC GATTCATTAA TGCAGCTGGC  6060
6061  ACGACAGGTT TCCCGACTGG·AAAGCGGGCA GTGAGCGCAA CGCAATTAAT GTGAGTTAGC  6120
6121  TCACTCATTA GGCACCCCAG GCTTTACACT TTATGCTTCC GGCTCGTATG TTGTGTGGAA  6180
6181  TTGTGAGCGG ATAACAATTT CACACGCGTC ACTTGGCACT GGCCGTCGTT TTACAACGTC  6240
6241  GTGACTGGGA AAACCCTGGC GTTACCCAAG CTTTGTACAT GGAGAAAATA AAGTGAAACA  6300
6301  AAGCACTATT GCACTGGCAC TCTTACCGTT ACCGTTACTG TTTACCCCTG TGACAAAAGC  6360
6361  CGCCCAGGTC CAGCTGCTCG AGTCAGGCCT ATTGTGCCCA GGGGATTGTA CTACTGGATC  6420
6421  CTAGGCTGAA GGCGATGACC CTGCTAAGGC TGCATTCAAT AGTTTACAGG CAAGTGCTAC  6480
6481  TGAGTACATT GGCTACGCTT GGGCTATGGT AGTAGTTATA GTTGGTGCTA CCATAGGGAT  6540
6541  TAAATTATTC AAAAAGTTTA CGAGCAAGGC TTCTTAAGCA ATAGCGAAGA GGCCCGCACC  6600
6601  GATCGCCCTT CCCAACAGTT GCGCAGCCTG AATGGCGAAT GGCGCTTTGC CTGGTTTCCG  6660
6661  GCACCAGAAG CGGTGCCGGA AAGCTGGCTG GAGTGCGATC TTCCTGAGGC CGATACGGTC  6720
6721  GTCGTCCCCT CAAACTGGCA GATGCAGGGT TACGATGCGC CCATCTACAC CAACGTAACC  6780
6781  TATCCCATTA CGGTCAATCC GCCGTTTGTT CCCACGGAGA ATCCGACGGG TTGTTACTCG  6840
6841  CTCACATTTA ATGTTGATGA AAGCTGGCTA CAGGAAGGCC AGACGCGAAT TATTTTTGAT  6900
6901  GGCGTTCCTA TTGGTTAAAA AATGAGCTGA TTTAACAAAA ATTTAACGCG AATTTTAACA  6960
6961  AAATATTAAC GTTTACAATT TAAATATTTG CTTATACAAT CTTCCTGTTT TTGGGGCTTT  7020
7021  TCTGATTATC AACCGGGGTA CATATGATTG ACATGCTAGT TTTACGATTA CCGTTCATCG  7080
7081  ATTCTCTTGT TTGCTCCAGA CTCTCAGGCA ATGACCTGAT AGCCTTTGTA GATCTCTCAA  7140
7141  AAATAGCTAC CCTCTCCGGC ATTAATTTAT CAGCTAGAAC GGTTGAATAT CATATTGATG  7200
7201  GTGATTTGAC TGTCTCCGGC CTTTCTCACC CTTTTGAATC TTTACCTACA CATTACTCAG  7260
7261  GCATTGCATT TAAAATATAT GAGGGTTCTA AAAATTTTTA TCCTTGCGTT GAAATAAAGG  7320
7321  CTTCTCCCGC AAAAGTATTA CAGGGTCATA ATGTTTTTGG TACAACCGAT·TTAGCTTTAT  7380
7381  GCTCTGAGGC TTTATTGCTT AATTTTGCTA ATTCTTTGCC TTGCCTGTAT GATTTATTGG  7440
7441  ACGTT                                                              7445
          |   10      |   20      |   30      |   40      |   50      |   60
```

FIG. 2C

```
      1         10          20          30          40          50          60
      1  AATGCTACTA  CTATTAGTAG  AATTGATGCC  ACCTTTTCAG  CTCGCGCCCC  AAATGAAAAT    60
     61  ATAGCTAAAC  AGGTTATTGA  CCATTTGCGA  AATGTATCTA  ATGGTCAAAC  TAAATCTACT   120
    121  CGTTCGCAGA  ATTGGGAATC  AACTGTTACA  TGGAATGAAA  CTTCCAGACA  CCGTACTTTA   180
    181  GTTGCATATT  TAAAACATGT  TGAGCTACAG  CACCAGATTC  AGCAATTAAG  CTCTAAGCCA   240
    241  TCCGCAAAAA  TGACCTCTTA  TCAAAAGGAG  CAATTAAAGG  TACTCTCTAA  TCCTGACCTG   300
    301  TTGGAGTTTG  CTTCCGGTCT  GGTTCGCTTT  GAAGCTCGAA  TTAAAACGCG  ATATTTGAAG   360
    361  TCTTTCGGGC  TTCCTCTTAA  TCTTTTTGAT  GCAATCCGCT  TTGCTTCTGA  CTATAATAGT   420
    421  CAGGGTAAAG  ACCTGATTTT  TGATTTATGG  TCATTCTCGT  TTTCTGAACT  GTTTAAAGCA   480
    481  TTTGAGGGGG  ATTCAATGAA  TATTTATGAC  GATTCCGCAG  TATTGGACGC  TATCCAGTCT   540
    541  AAACATTTTA  CTATTACCCC  CTCTGGCAAA  ACTTCTTTTG  CAAAAGCCTC  TCGCTATTTT   600
    601  GGTTTTTATC  GTCGTCTGGT  AAACGAGGGT  TATGATAGTG  TTGCTCTTAC  TATGCCTCGT   660
    661  AATTCCTTTT  GGCGTTATGT  ATCTGCATTA  GTTGAATGTG  GTATTCCTAA  ATCTCAACTG   720
    721  ATGAATCTTT  CTACCTGTAA  TAATGTTGTT  CCGTTAGTTC  GTTTTATTAA  CGTAGATTTT   780
    781  TCTTCCCAAC  GTCCTGACTG  GTATAATGAG  CCAGTTCTTA  AAATCGCATA  AGGTAATTCA   840
    841  CAATGATTAA  AGTTGAAATT  AAACCATCTC  AAGCCCAATT  TACTACTCGT  TCTGGTGTTT   900
    901  CTCGTCAGGG  CAAGCCTTAT  TCACTGAATG  AGCAGCTTTG  TTACGTTGAT  TTGGGTAATG   960
    961  AATATCCGGT  TCTTGTCAAG  ATTACTCTTG  ATGAAGGTCA  GCCAGCCTAT  GCGCCTGGTC  1020
   1021  TGTACACCGT  TCATCTGTCC  TCTTTCAAAG  TTGGTCAGTT  CGGTTCCCTT  ATGATTGACC  1080
   1081  GTCTGCGCCT  CGTTCCGGCT  AAGTAACATG  GAGCAGGTCG  GGGATTTCGA  CACAATTTAT  1140
   1141  CAGGCGATGA  TACAAATCTC  CGTTGTACTT  TGTTTCGCGC  TTGGTATAAT  CGCTGGGGGT  1200
   1201  CAAAGATGAG  TGTTTTAGTG  TATTCTTTCG  CCTCTTTCGT  TTTAGGTTGG  TGCCTTCGTA  1260
   1261  GTGGCATTAC  GTATTTTACC  CGTTTAATGG  AAACTTCCTC  ATGAAAAAGT  CTTTAGTCCT  1320
   1321  CAAAGCCTCT  GTAGCCGTTG  CTACCCTCGT  TCCGATGCTG  TCTTTCGCTG  CTGAGGGTGA  1380
   1381  CGATCCCGCA  AAAGCGGCCT  TTAACTCCCT  GCAAGCCTCA  GCGACCGAAT  ATATCGGTTA  1440
   1441  TGCGTGGGCG  ATGGTTGTTG  TCATTGTCGG  CGCAACTATC  GGTATCAAGC  TGTTTAAGAA  1500
   1501  ATTCACCTCG  AAAGCAAGCT  GATAAACCGA  TACAATTAAA  GGCTCCTTTT  GGAGCCTTTT  1560
   1561  TTTTTGGAGA  TTTTCAACGT  GAAAAAATTA  TTATTCGCAA  TTCCTTTAGT  TGTTCCTTTC  1620
   1621  TATTCTCACT  CCGCTGAAAC  TGTTGAAAGT  TGTTTAGCAA  AACCCCATAC  AGAAAATTCA  1680
   1681  TTTACTAACG  TCTGGAAAGA  CGACAAAACT  TTAGATCGTT  ACGCTAACTA  TGAGGGTTGT  1740
   1741  CTGTGGAATG  CTACAGGCGT  TGTAGTTTGT  ACTGGTGACG  AAACTCAGTG  TTACGGTACA  1800
   1801  TGGGTTCCTA  TTGGGCTTGC  TATCCCTGAA  AATGAGGGTG  GTGGCTCTGA  GGGTGGCGGT  1860
   1861  TCTGAGGGTG  GCGGTTCTGA  GGGTGGCGGT  ACTAAACCTC  CTGAGTACGG  TGATACACCT  1920
   1921  ATTCCGGGCT  ATACTTATAT  CAACCCTCTC  GACGGCACTT  ATCCGCCTGG  TACTGAGCAA  1980
   1981  AACCCCGCTA  ATCCTAATCC  TTCTCTTGAG  GAGTCTCAGC  CTCTTAATAC  TTTCATGTTT  2040
   2041  CAGAATAATA  GGTTCCGAAA  TAGGCAGGGG  GCATTAACTG  TTTATACGGG  CACTGTTACT  2100
   2101  CAAGGCACTG  ACCCCGTTAA  AACTTATTAC  CAGTACACTC  CTGTATCATC  AAAAGCCATG  2160
   2161  TATGACGCTT  ACTGGAACGG  TAAATTCAGA  GACTGCGCTT  TCCATTCTGG  CTTTAATGAA  2220
   2221  GATCCATTCG  TTTGTGAATA  TCAAGGCCAA  TCGTCTGACC  TGCCTCAACC  TCCTGTCAAT  2280
   2281  GCTGGCGGCG  GCTCTGGTGG  TGGTTCTGGT  GGCGGCTCTG  AGGGTGGTGG  CTCTGAGGGT  2340
   2341  GGCGGTTCTG  AGGGTGGCGG  CTCTGAGGGA  GGCGGTTCCG  GTGGTGGCTC  TGGTTCCGGT  2400
   2401  GATTTTGATT  ATGAAAAGAT  GGCAAACGCT  AATAAGGGGG  CTATGACCGA  AAATGCCGAT  2460
   2461  GAAAACGCGC  TACAGTCTGA  CGCTAAAGGC  AAACTTGATT  CTGTCGCTAC  TGATTACGGT  2520
   2521  GCTGCTATCG  ATGGTTTCAT  TGGTGACGTT  TCCGGCCTTG  CTAATGGTAA  TGGTGCTACT  2580
   2581  GGTGATTTTG  CTGGCTCTAA  TTCCCAAATG  GCTCAAGTCG  GTGACGGTGA  TAATTCACCT  2640
   2641  TTAATGAATA  ATTTCCGTCA  ATATTTACCT  TCCCTCCCTC  AATCGGTTGA  ATGTCGCCCT  2700
   2701  TTTGTCTTTA  GCGCTGGTAA  ACCATATGAA  TTTTCTATTG  ATTGTGACAA  AATAAACTTA  2760
   2761  TTCCGTGGTG  TCTTTGCGTT  TCTTTTATAT  GTTGCCACCT  TTATGTATGT  ATTTTCTACG  2820
   2821  TTTGCTAACA  TACTGCGTAA  TAAGGAGTCT  TAATCATGCC  AGTTCTTTTG  GGTATTCCGT  2880
   2881  TATTATTGCG  TTTCCTCGGT  TTCCTTCTGG  TAACTTTGTT  CGGCTATCTG  CTTACTTTTC  2940
   2941  TTAAAAGGGG  CTTCGGTAAG  ATAGCTATTG  CTATTTCATT  GTTTCTTGCT  CTTATTATTG  3000
          |    10      |    20      |    30      |    40      |    50      |    60
```

FIG. 3A

```
        |   10      |   20      |   30      |   40      |   50      |   60
3001  GGCTTAACTC AATTCTTGTG GGTTATCTCT CTGATATTAG CGCTCAATTA CCCTCTGACT  3060
3061  TTGTTCAGGG TGTTCAGTTA ATTCTCCCGT CTAATGCGCT TCCCTGTTTT TATGTTATTC  3120
3121  TCTCTGTAAA GGCTGCTATT TTCATTTTTG ACGTTAAACA AAAAATCGTT TCTTATTTGG  3180
3181  ATTGGGATAA ATAATATGGC TGTTTATTTT GTAACTGGCA AATTAGGCTC TGGAAAGACG  3240
3241  CTCGTTAGCG TTGGTAAGAT TCAGGATAAA ATTGTAGCTG GGTGCAAAAT AGCAACTAAT  3300
3301  CTTGATTTAA GGCTTCAAAA CCTCCCGCAA GTCGGGAGGT TCGCTAAAAC GCCTCGCGTT  3360
3361  CTTAGAATAC CGGATAAGCC TTCTATATCT GATTTGCTTG CTATTGGGCG CGGTAATGAT  3420
3421  TCCTACGATG AAAATAAAAA CGGCTTGCTT GTTCTCGATG AGTGCGGTAC TTGGTTTAAT  3480
3481  ACCCGTTCTT GGAATGATAA GGAAAGACAG CCGATTATTG ATTGGTTTCT ACATGCTCGT  3540
3541  AAATTAGGAT GGGATATTAT TTTTCTTGTT CAGGACTTAT CTATTGTTGA TAAACAGGCG  3600
3601  CGTTCTGCAT TAGCTGAACA TGTTGTTTAT TGTCGTCGTC TGGACAGAAT TACTTTACCT  3660
3661  TTTGTCGGTA CTTTATATTC TCTTATTACT GGCTCGAAAA TGCCTCTGCC TAAATTACAT  3720
3721  GTTGGCGTTG TTAAATATGG CGATTCTCAA TTAAGCCCTA CTGTTGAGCG TTGGCTTTAT  3780
3781  ACTGGTAAGA ATTTGTATAA CGCATATGAT ACTAAACAGG CTTTTTCTAG TAATTATGAT  3840
3841  TCCGGTGTTT ATTCTTATTT AACGCCTTAT TTATCACACG GTCGGTATTT CAAACCATTA  3900
3901  AATTTAGGTC AGAAGATGAA GCTTACTAAA ATATATTTGA AAAGTTTTC ACGCGTTCTT  3960
3961  TGTCTTGCGA TTGGATTTGC ATCAGCATTT ACATATAGTT ATATAACCCA ACCTAAGCCG  4020
4021  GAGGTAAAA AGGTAGTCTC TCAGACCTAT GATTTTGATA AATTCACTAT TGACTCTTCT  4080
4081  CAGCGTCTTA ATCTAAGCTA TCGCTATGTT TTCAAGGATT CTAAGGGAAA ATTAATTAAT  4140
4141  AGCGACGATT TACAGAAGCA AGGTTATTCA CTCACATATA TTGATTTATG TACTGTTTCC  4200
4201  ATTAAAAAAG GTAATTCAAA TGAAATTGTT TGAAATGAAT AATCGCCTC TGCGCGATTT  4260
4261  TGTTTCATCA TCTCTTTTTG CTCAGGTAAT ATCCGTTATT GTTTCTCCCG ATGTAAAAGG  4320
4321  TGTAACTTGG TATTCAAAGC AATCAGGCGA ACCTGAAAAT CTACGCAATT TCTTTATTTC  4380
4381  TACTGTTACT GTATATTCAT CTGACGTTAA TGGTTCAATT CCTTCCATAA TTCAGAAGTA  4440
4441  TGTTTACGT GCTAATAATT TTGATATGGT TGGTTCAATT CCTTCCATAA TTCAGAAGTA  4500
4501  TAATCCAAAC AATCAGGATT ATATTGATGA ATTGCCATCA TCTGATAATC AGGAATATGA  4560
4561  TGATAATTCC GCTCCTTCTG GTGGTTTCTT TGTTCCGCAA AATGATAATG TTACTCAAAC  4620
4621  TTTTAAAATT AATAACGTTC GGGCAAGGA TTTAATACGA GTTGTCGAAT TGTTTGTAAA  4680
4681  GTCTAATACT TCTAAATCCT CAAATGTATT ATCTATTGAC GGCTCTAATC TATTAGTTGT  4740
4741  TAGTGCACCT AAAGATATTT TAGATAACCT CTTTCTACTG TTTCATTTGT TTGATTTGCC  4800
4801  AACTGACCAG ATATTGATTG AGGGTTTGAT ATTTGAGGTT CAGCAAGGTG ATGCTTTAGA  4860
4861  TTTTTCATTT GCTGCTGGCT CTCAGCGTGG CACTGTTGCA GGCGGTGTTA ATACTGACCG  4920
4921  CCTCACCTCT GTTTTATCTT CTGCTGGTGG TTCGTTCGGT ATTTTTAATG GCGATGTTTT  4980
4981  AGGGCTATCA GTTCGCGCAT TAAAGACTAA TAGCCATTCA AAAATATTGT CTGTGCCACG  5040
5041  TATTCTTACG CTTTCAGGTC AGAAGGGTTC TATCTCTGTT GGCCAGAATG TCCCTTTTAT  5100
5101  TACTGGTCGT GTGACTGGTG AATCTGCCAA TGTAAATAAT CCATTTCAGA CGATTGAGCG  5160
5161  TCAAAATGTA GGTATTTCCA TGAGCGTTTT TCCTGTTGCA ATGGCTGGCG GTAATATTGT  5220
5221  TCTGGATATT ACCAGCAAGG CCGATATTT GAGTTCTTCT ACTCAGGCAA GTGATGTTAT  5280
5281  TACTAATCAA AGAAGTATTG CTACAACGGT TAATTTGCGT GATGGACAGA CTCTTTTACT  5340
5341  CGGTGGCCTC ACTGATTATA AAAACACTTC TCAAGATTCT GGCGTACCGT TCCTGTCTAA  5400
5401  AATCCCTTTA ATCGGCCTCC TGTTTAGCTC CCGCTCTGAT TCCAACGAGG AAAGCACGTT  5460
5461  ATACGTGCTC GTCAAAGCAA CCATAGTACG CGCCCTGTAG CGGCGCATTA AGCGCGGCGG  5520
5521  GTGTGGTGGT TACGCGCAGC GTGACCGCTA CACTTGCCAG CGCCCTAGCG CCCGCTCCTT  5580
5581  TCGCTTTCTT CCCTTCCTTT CTCGCCACGT TCGCCGGCTT TCCCCGTCAA GCTCTAAATC  5640
5641  GGGGGCTCCC TTTAGGGTTC CGATTTAGTG CTTTACGGCA CCTCGACCCC AAAAAACTTG  5700
        |   10      |   20      |   30      |   40      |   50      |   60
```

FIG. 3B

```
        1         20        30        40        50        60
5701 ATTTGGGTGA TGGTTCACGT AGTGGGCCAT CGCCCTGATA GACGGTTTTT CGCCCTTTGA 5760
5761 CGTTGGAGTC CACGTTCTTT AATAGTGGAC TCTTGTTCCA AACTGGAACA ACACTCAACC 5820
5821 CTATCTCGGG CTATTCTTTT GATTTATAAG GGATTTTGCC GATTTCGGAA CCACCATCAA 5880
5881 ACAGGATTTT CGCCTGCTGG GGCAAACCAG CGTGGACCGC TTGCTGCAAC TCTCTCAGGG 5940
5941 CCAGGCGGTG AAGGGCAATC AGCTGTTGCC CGTCTCGCTG GTGAAAAGAA AAACCACCCT 6000
6001 GGCGCCCAAT ACGCAAACCG CCTCTCCCCG CGCGTTGGCC GATTCATTAA TGCAGCTGGC 6060
6061 ACGACAGGTT TCCCGACTGG AAAGCGGGCA GTGAGCGCAA CGCAATTAAT GTGAGTTAGC 6120
6121 TCACTCATTA GGCACCCCAG GCTTTACACT TTATGCTTCC GGCTCGTATG TTGTGTGGAA 6180
6181 TTGTGAGCGG ATAACAATTT CACACGCCAA GGAGACAGTC ATAATGAAAT ACCTATTGCC 6240
6241 TACGGCAGCC GCTGGATTGT TATTACTCGC TGCCCAACCA GCCATGGCCG AGCTCGTGAT 6300
6301 GACCCAGACT CCAGATATCC AACAGGAATG AGTGTTAATT CTAGAACGCG TCACTTGGCA 6360
6361 CTGGCCGTCG TTTTACAACG TCGTGACTGG GAAAACCCTG GCGTTACCCA AGCTTAATCG 6420
6421 CCTTGCAGAA TTCCCTTTCG CCAGCTGGCG TAATAGCGAA GAGGCCCGCA CCGATCGCCC 6480
6481 TTCCAACAG TTGCGCAGCC TGAATGGCGA ATGGCGCTTT GCCTGGTTTC CGGCACCAGA 6540
6541 AGCGGTGCCG GAAAGCTGGC TGGAGTGCGA TCTTCCTGAG GCCGATACGG TCGTCGTCCC 6600
6601 CTCAAACTGG CAGATGCACG GTTACGATGC GCCCATCTAC ACCAACGTAA CCTATCCCAT 6660
6661 TACGGTCAAT CCGCCGTTTG TTCCCACGGA GAATCCGACG GGTTGTTACT CGCTCACATT 6720
6721 TAATGTTGAT GAAAGCTGGC TACAGGAAGG CCAGACGCGA ATTATTTTTG ATGGCGTTCC 6780
6781 TATTGGTTAA AAAATGAGCT GATTTAACAA AAATTTAACG CGAATTTTAA CAAAATATTA 6840
6841 ACGTTTACAA TTTAAATATT TGCTTATACA ATCTTCCTGT TTTTGGGGCT TTTCTGATTA 6900
6901 TCAACCGGGG TACATATGAT TGACATGCTA GTTTTACGAT TACCGTTCAT CGATTCTCTT 6960
6961 GTTTGCTCCA GACTCTCAGG CAATGACCTG ATAGCCTTTG TAGATCTCTC AAAAATAGCT 7020
7021 ACCCTCTCCG GCATTAATTT ATCAGCTAGA ACGGTTGAAT ATCATATTGA TGGTGATTTG 7080
7081 ACTGTCTCCG GCCTTTCTCA CCCTTTTGAA TCTTTACCTA CACATTACTC AGGCATTGCA 7140
7141 TTTAAAATAT ATGAGGGTTC TAAAAATTTT TATCCTTGCG TTGAAATAAA GGCTTCTCCC 7200
7201 GCAAAAGTAT TACAGGGTCA TAATGTTTTT GGTACAACCG ATTTAGCTTT ATGCTCTGAG 7260
7261 GCTTTATTGC TTAATTTTGC TAATTCTTTG CCTTGCCTGT ATGATTTATT GGATGTT     7317
        10        20        30        40        50        60
```

```
         |   10       |   20       |   30       |   40       |   50       |   60
 6001  AATACGCAAA  CCGCCTCTCC  CCGCGCGTTG  GCCGATTCAT  TAATGCAGCT  GGCACGACAG  6060
 6061  GTTTCCCGAC  TGGAAAGCGG  GCAGTGAGCG  CAACGCAATT  AATGTGAGTT  AGCTCACTCA  6120
 6121  TTAGGCACCC  CAGGCTTTAC  ACTTTATGCT  TCCGGCTCGT  ATGTTGTGTG  GAATTGTGAG  6180
 6181  CGGATAACAA  TTCACACGC   CAAGGAGACA  GTCATAATGA  AATACCTATT  GCCTACGGCA  6240
 6241  GCCGCTGGAT  TGTTATTACT  CGCTGCCCAA  CCAGCCATGG  CCGAGCTCTT  CCCGCCATCT  6300
 6301  GATGAGCAGT  TGAAATCTGG  AACTGCCTCT  GTTGTGTGCC  TGCTGAATAA  CTTCTATCCC  6360
 6361  AGAGAGGCCA  AAGTACAGTG  GAAGGTGGAT  AACGCCCTCC  AATCGGGTAA  CTCCCAGGAG  6420
 6421  AGTGTCACAG  AGCAGGACAG  CAAGGACAGC  ACCTACAGCC  TCAGCAGCAC  CCTGACGCTG  6480
 6481  AGCAAAGCAG  ACTACGAGAA  ACACAAAGTC  TACGCCTGCG  AAGTCACCCA  TCAGGGCCTG  6540
 6541  AGCTCGCCCG  TCACAAAGAG  CTTCAACAGG  GGAGAGTGTT  CTAGAACGCG  TCACTTGGCA  6600
 6601  CTGGCCGTCG  TTTTACAACG  TCGTGACTGG  GAAAACCCTG  GCGTTACCCA  AGCTTAATCG  6660
 6661  CCTTGCAGAA  TTCCCTTTCG  CCAGCTGGCG  TAATAGCGAA  GAGGCCCGCA  CCGATCGCCC  6720
 6721  TTCCCAACAG  TTGCGCAGCC  TGAATGGCGA  ATGGCGCTTT  GCCTGGTTTC  CGGCACCAGA  6780
 6781  AGCGGTGCCG  GAAAGCTGGC  TGGAGTGCGA  TCTTCCTGAG  GCCGATACGG  TCGTCGTCCC  6840
 6841  CTCAAACTGG  CAGATGCACG  GTTACGATGC  GCCCATCTAC  ACCAACGTAA  CCTATCCCAT  6900
 6901  TACGGTCAAT  CCGCCGTTTG  TTCCCACGGA  GAATCCGACG  GGTTGTTACT  CGCTCACATT  6960
 6961  TAATGTTGAT  GAAAGCTGGC  TACAGGAAGG  CCAGACGCGA  ATTATTTTTG  ATGGCGTTCC  7020
 7021  TATTGGTTAA  AAAATGAGCT  GATTTAACAA  AAATTTAACG  CGAATTTTAA  CAAAATATTA  7080
 7081  ACGTTTACAA  TTTAAATATT  TGCTTATACA  ATCTTCCTGT  TTTTGGGGCT  TTTCTGATTA  7140
 7141  TCAACCGGGG  TACATATGAT  TGACATGCTA  GTTTTACGAT  TACCGTTCAT  CGATTCTCTT  7200
 7201  GTTTGCTCCA  GACTCTCAGG  CAATGACCTG  ATAGCCTTTG  TAGATCTCTC  AAAAATAGCT  7260
 7261  ACCCTCTCCG  GCATTAATTT  ATCAGCTAGA  ACGGTTGAAT  ATCATATTGA  TGGTGATTTG  7320
 7321  ACTGTCTCCG  GCCTTTCTCA  CCCTTTTGAA  TCTTTACCTA  CACATTACTC  AGGCATTGCA  7380
 7381  TTTAAAATAT  ATGAGGGTTC  TAAAAATTTT  TATCCTTGCG  TTGAAATAAA  GGCTTCTCCC  7440
 7441  GCAAAAGTAT  TACAGGGTCA  TAATGTTTTT  GGTACAACCG  ATTTAGCTTT  ATGCTCTGAG  7500
 7501  GCTTTATTGC  TTAATTTTGC  TAATTCTTTG  CCTTGCCTGT  ATGATTTATT  GGATGTT     7557
         |   10       |   20       |   30       |   40       |   50       |   60
```

FIG. 4C

```
         1        10        20        30         40        50         60
   1  AATGCTACTA CTATTAGTAG AATTGATGCC ACCTTTTCAG CTCGCGCCCC AAATGAAAAT   60
  61  ATAGCTAAAC AGGTTATTGA CCATTTGCGA AATGTATCTA ATGGTCAAAC TAAATCTACT  120
 121  CGTTCGCAGA ATTGGGAATC AACTGTTACA TGGAATGAAA CTTCCAGACA CCGTACTTTA  180
 181  GTTGCATATT TAAAACATGT TGAGCTACAG CACCAGATTC AGCAATTAAG CTCTAAGCCA  240
 241  TCTGCAAAAA TGACCTCTTA TCAAAAGGAG CAATTAAAGG TACTCTCTAA TCCTGACCTG  300
 301  TTGGAGTTTG CTTCCGGTCT GGTTCGCTTT GAAGCTCGAA TTAAAACGCG ATATTTGAAG  360
 361  TCTTTCGGGC TTCCTCTTAA TCTTTTTGAT GCAATCCGCT TTGCTTCTGA CTATAATAGT  420
 421  CAGGGTAAAG ACCTGATTTT TGATTTATGG TCATTCTCGT TTTCTGAACT GTTTAAAGCA  480
 481  TTTGAGGGGG ATTCAATGAA TATTTATGAC GATTCCGCAG TATTGGACGC TATCCAGTCT  540
 541  AAACATTTTA CTATTACCCC CTCTGGCAAA ACTTCTTTTG CAAAAGCCTC TCGCTATTTT  600
 601  GGTTTTTATC GTCGTCTGGT AAACGAGGGT TATGATAGTG TTGCTCTTAC TATGCCTCGT  660
 661  AATTCCTTTT GGCGTTATGT ATCTGCATTA GTTGAATGTG GTATTCCTAA ATCTCAACTG  720
 721  ATGAATCTTT CTACCTGTAA TAATGTTGTT CCGTTAGTTC GTTTTATTAA CGTAGATTTT  780
 781  TCTTCCCAAC GTCCTGACTG GTATAATGAG CCAGTTCTTA AAATCGCATA AGGTAATTCA  840
 841  CAATGATTAA AGTTGAAATT AAACCATCTC AAGCCCAATT TACTACTCGT TCTGGTGTTT  900
 901  CTCGTCAGGG CAAGCCTTAT TCACTGAATG AGCAGCTTTG TTACGTTGAT TTGGGTAATG  960
 961  AATATCCGGT TCTTGTCAAG ATTACTCTTG ATGAAGGTCA GCCAGCCTAT GCGCCTGGTC 1020
1021  TGTACACCGT TCATCTGTCC TCTTTCAAAG TTGGTCAGTT CGGTTCCCTT ATGATTGACC 1080
1081  GTCTGCGCCT CGTTCCGGCT AAGTAACATG GAGCAGGTCG CGGATTTCGA CACAATTTAT 1140
1141  CAGGCGATGA TACAAATCTC CGTTGTACTT TGTTTCGCGC TTGGTATAAT CGCTGGGGGT 1200
1201  CAAAGATGAG TGTTTTAGTG TATTCTTTCG CCTCTTTCGT TTTAGGTTGG TGCCTTCGTA 1260
1261  GTGGCATTAC GTATTTTACC CGTTTAATGG AAACTTCCTC ATGAAAAAGT CTTTAGTCCT 1320
1321  CAAAGCCTCT GTAGCCGTTG CTACCCTCGT TCCGATGCTG TCTTTCGCTG CTGAGGGTGA 1380
1381  CGATCCCGCA AAAGCGGCCT TTAACTCCCT GCAAGCCTCA GCGACCGAAT ATATCGGTTA 1440
1441  TGCGTGGGCG ATGGTTGTTG TCATTGTCGG CGCAACTATC GGTATCAAGC TGTTTAAGAA 1500
1501  ATTCACCTCG AAAGCAAGCT GATAAACCGA TACAATTAAA GGCTCCTTTT GGAGCCTTTT 1560
1561  TTTTTGGAGA TTTTCAACGT GAAAAAATTA TTATTCGCAA TTCCTTTAGT TGTTCCTTTC 1620
1621  TATTCTCACT CCGCTGAAAC TGTTGAAAGT TGTTTAGCAA AACCCCATAT AGAAAATTCA 1680
1681  TTTACTAACG TCTGGAAAGA CGACAAAACT TTAGATCGTT ACGCTAACTA TGAGGGTTGT 1740
1741  CTGTGGAATG CTACAGGCGT TGTAGTTTGT ACTGGTGACG AAACTCAGTG TTACGGTACA 1800
1801  TGGGTTCCTA TTGGGCTTGC TATCCCTGAA AATGAGGGTG GTGGCTCTGA GGGTGGCGGT 1860
1861  TCTGAGGGTG GCGGTTCTGA GGGTGGCGGT ACTAAACCTC CTGAGTACGG TGATACACCT 1920
1921  ATTCCGGGCT ATACTTATAT CAACCCTCTC GACGGCACTT ATCCGCCTGG TACTGAGCAA 1980
1981  AACCCCGCTA ATCCTAATCC TTCTCTTGAG GAGTCTCAGC CTCTTAATAC TTTCATGTTT 2040
2041  CAGAATAATA GGTTCCGAAA TAGGCAGGGG GCATTAACTG TTTATACGGG CACTGTTACT 2100
2101  CAAGGCACTG ACCCCGTTAA AACTTATTAC CAGTACACTC CTGTATCATC AAAAGCCATG 2160
2161  TATGACGCTT ACTGGAACGG TAAATTCAGA GACTGCGCTT TCCATTCTGG CTTTAATGAA 2220
2221  GATCCATTCG TTTGTGAATA TCAAGGCCAA TCGTCTGACC TGCCTCAACC TCCTGTCAAT 2280
2281  GCTGGCGGCG GCTCTGGTGG TGGTTCTGGT GGCGGCTCTG AGGGTGGTGG CTCTGAGGGT 2340
2341  GGCGGTTCTG AGGGTGGCGG CTCTGAGGGA GGCGGTTCCG GTGGTGGCTC TGGTTCCGGT 2400
2401  GATTTTGATT ATGAAAAGAT GGCAAACGCT AATAAGGGGG CTATGACCGA AAATGCCGAT 2460
2461  GAAAACGCGC TACAGTCTGA CGCTAAAGGC AAACTTGATT CTGTCGCTAC TGATTACGGT 2520
2521  GCTGCTATCG ATGGTTTCAT TGGTGACGTT TCCGGCCTTG CTAATGGTAA TGGTGCTACT 2580
2581  GGTGATTTTG CTGGCTCTAA TTCCCAAATG GCTCAAGTCG GTGACGGTGA TAATTCACCT 2640
2641  TTAATGAATA ATTTCCGTCA ATATTTACCT TGCCTCCCTC AATCGGTTGA ATGTCGCCCT 2700
2701  TTTGTCTTTA GCGCTGGTAA ACCATATGAA TTTTCTATTG ATTGTGACAA AATAAACTTA 2760
2761  TTCCGTGGTG TCTTTGCGTT TCTTTTATAT GTTGCCACCT TTATGTATGT ATTTTCTACG 2820
2821  TTTGCTAACA TACTGCGTAA TAAGGAGTCT TAATCATGCC AGTTCTTTTG GGTATTCCGT 2880
2881  TATTATTGCG TTTCCTCGGT TTCCTTCTGG TAACTTTGTT CGGCTATCTG CTTACTTTTC 2940
2941  TTAAAAAGGG CTTCGGTAAG ATAGCTATTG CTATTTCATT GTTTCTTGCT GTTATTATTG 3000
```

FIG. 5A

```
         1  10         |  20         |  30         |  40         |  50         |  60
3001  GGCTTAACTC  AATTCTTGTG  GGTTATCTCT  CTGATATTAG  CGCTCAATTA  CCCTCTGACT  3060
3061  TTGTTCAGGG  TGTTCAGTTA  ATTCTCCCGT  CTAATGCGCT  TCCCTGTTTT  TATGTTATTC  3120
3121  TCTCTGTAAA  GGCTGCTATT  TTCATTTTTG  ACGTTAAACA  AAAAATCGTT  TCTTATTTGG  3180
3181  ATTGGGATAA  ATAATATGGC  TGTTTATTTT  GTAACTGGCA  AATTAGGCTC  TGGAAAGACG  3240
3241  CTCGTTAGCG  TTGGTAAGAT  TCAGGATAAA  ATTGTAGCTG  GGTGCAAAAT  AGCAACTAAT  3300
3301  CTTGATTTAA  GGCTTCAAAA  CCTCCGCAA   GTCGGAGGT  TCGCTAAAAC  GCCTCGCGTT  3360
3361  CTTAGAATAC  CGGATAAGCC  TTCTATATCT  GATTTGCTTG  CTATTGGGCG  CGGTAATGAT  3420
3421  TCCTACGATG  AAAATAAAAA  CGGCTTGCTT  GTTCTCGATG  AGTGCGGTAC  TTGGTTTAAT  3480
3481  ACCCGTTCTT  GGAATGATAA  GGAAAGACAG  CCGATTATTG  ATTGGTTTCT  ACATGCTCGT  3540
3541  AAATTAGGAT  GGGATATTAT  TTTTCTTGTT  CAGGACTTAT  CTATTGTTGA  TAAACAGGCG  3600
3601  CGTTCTGCAT  TAGCTGAACA  TGTTGTTTAT  TGTCGTCGTC  TGGACAGAAT  TACTTTACCT  3660
3661  TTTGTCGGTA  CTTTATATTC  TCTTATTACT  GGCTCGAAAA  TGCCTCTGCC  TAAATTACAT  3720
3721  GTTGGCGTTG  TTAAATATGG  CGATTCTCAA  TTAAGCCCTA  CTGTTGAGCG  TTGGCTTTAT  3780
3781  ACTGGTAAGA  ATTTGTATAA  CGCATATGAT  ACTAAACAGG  CTTTTTCTAG  TAATTATGAT  3840
3841  TCCGGTGTTT  ATTCTTATTT  AACGCCTTAT  TTATCACACG  GTCGGTATTT  CAAACCATTA  3900
3901  AATTTAGGTC  AGAAGATGAA  GCTTACTAAA  ATATATTTGA  AAAAGTTTTC  ACGCGTTCTT  3960
3961  TGTCTTGCGA  TTGGATTTGC  ATCAGCATTT  ACATATAGTT  ATATAACCCA  ACCTAAGCCG  4020
4021  GAGGTTAAAA  AGGTAGTCTC  TCAGACCTAT  GATTTTGATA  AATTCACTAT  TGACTCTTCT  4080
4081  CAGCGTCTTA  ATCTAAGCTA  TCGCTATGTT  TTCAAGGATT  CTAAGGGAAA  ATTAATTAAT  4140
4141  AGCGACGATT  TACAGAAGCA  AGGTTATTCA  CTCACATATA  TTGATTTATG  TACTGTTTCC  4200
4201  ATTAAAAAAG  GTAATTCAAA  TGAAATTGTT  AAATGTAATT  AATTTTGTTT  TCTTGATGTT  4260
4261  TGTTTCATCA  TCTTCTTTTG  CTCAGGTAAT  TGAAATGAAT  AATTCGCCTC  TGCGCGATTT  4320
4321  TGTAACTTGG  TATTCAAAGC  AATCAGGCGA  ATCCGTTATT  GTTTCTCCCG  ATGTAAAAGG  4380
4381  TACTGTTACT  GTATATTCAT  CTGACGTTAA  ACCTGAAAAT  CTACGCAATT  TCTTTATTTC  4440
4441  TGTTTTACGT  GCTAATAATT  TTGATATGGT  TGGTTCAATT  CCTTCCATAA  TTCAGAAGTA  4500
4501  TAATCCAAAC  AATCAGGATT  ATATTGATGA  ATTGCCATCA  TCTGATAATC  AGGAATATGA  4560
4561  TGATAATTCC  GCTCCTTCTG  GTGGTTTCTT  TGTTCCGCAA  AATGATAATG  TTACTCAAAC  4620
4621  TTTTAAAATT  AATAACGTTC  GGGCAAAGGA  TTTAATACGA  GTTGTCGAAT  TGTTTGTAAA  4680
4681  GTCTAATACT  TCTAAATCCT  CAAATGTATT  ATCTATTGAC  GGCTCTAATC  TATTAGTTGT  4740
4741  TAGTGCACCT  AAAGATATTT  TAGATAACCT  TCCTCAATTC  CTTTCTACTG  TTGATTTGCC  4800
4801  AACTGACCAG  ATATTGATTG  AGGGTTTGAT  ATTTGAGGTT  CAGCAAGGTG  ATGCTTTAGA  4860
4861  TTTTTCATTT  GCTGCTGGCT  CTCAGCGTGG  CACTGTTGCA  GGCGGTGTTA  ATACTGACCG  4920
4921  CCTCACCTCT  GTTTTATCTT  CTGCTGGTGG  TTCGTTCGGT  ATTTTTAATG  GCGATGTTTT  4980
4981  AGGGCTATCA  GTTCGCGCAT  TAAAGACTAA  TAGCCATTCA  AAAATATTGT  CTGTGCCACG  5040
5041  TATTCTTACG  CTTTCAGGTC  AGAAGGGTTC  TATCTCTGTT  GGCCAGAATG  TCCCTTTTAT  5100
5101  TACTGGTCGT  GTGACTGGTG  AATCTGCCAA  TGTAAATAAT  CCATTTCAGA  CGATTGAGCG  5160
5161  TCAAAATGTA  GGTATTTCCA  TGAGCGTTTT  TCCTGTTGCA  ATGGCTGGCG  GTAATATTGT  5220
5221  TCTGGATATT  ACCAGCAAGG  CCGATAGTTT  GAGTTCTTCT  ACTCAGGCAA  GTGATGTTAT  5280
5281  TACTAATCAA  AGAAGTATTG  CTACAACGGT  TAATTTGCGT  GATGGACAGA  CTCTTTTTACT  5340
5341  CGGTGGCCTC  ACTGATTATA  AAAACACTTC  TCAAGATTCT  GGCGTACCGT  TCCTGTCTAA  5400
5401  AATCCCTTTA  ATCGGCCTCC  TGTTTAGCTC  CCGCTCTGAT  TCCAACGAGG  AAAGCACGTT  5460
5461  ATACGTGCTC  GTCAAAGCAA  CCATAGTACG  CGCCCTGTAG  CGGCGCATTA  AGCGCGGCGG  5520
5521  GTGTGGTGGT  TACGCGCAGC  GTGACCGCTA  CACTTGCCAG  CGCCCTAGCG  CCCGCTCCTT  5580
5581  TCGCTTTCTT  CCCTTCCTTT  CTCGCCACGT  TCGCCGGCTT  TCCCCGTCAA  GCTCTAAATC  5640
5641  GGGGGCTCCC  TTTAGGGTTC  CGATTTAGTG  CTTTACGGCA  CCTCGACCCC  AAAAAACTTG  5700
5701  ATTTGGGTGA  TGGTTCACGT  AGTGGGCCAT  CGCCCTGATA  GACGGTTTTT  CGCCCTTTGA  5760
5761  CGTTGGAGTC  CACGTTCTTT  AATAGTGGAC  TCTTGTTCCA  AACTGGAACA  ACACTCAACC  5820
5821  CTATCTCGGG  CTATTCTTTT  GATTTATAAG  GGATTTTGCC  GATTTCGGAA  CCACCATCAA  5880
5881  ACAGGATTTT  CGCCTGCTGG  GGCAAACCAG  CGTGGACCGC  TTGCTGCAAC  TCTCTCAGGG  5940
5941  CCAGGCGGTG  AAGGGCAATC  AGCTGTTGCC  CGTCTCGCTG  GTGAAAAGAA  AAACCACCCT  6000
         |  10         |  20         |  30         |  40         |  50         |  60
```

FIG. 5B

```
        |  10        |  20        |  30        |  40        |  50        |  60
6001    GGCGCCCAAT   ACGCAAACCG   CCTCTCCCCG   CGCGTTGGCC   GATTCATTAA   TGCAGCTGGC   6060
6061    ACGACAGGTT   TCCCGACTGG   AAAGCGGGCA   GTGAGCGCAA   CGCAATTAAT   GTGAGTTAGC   6120
6121    TCACTCATTA   GGCACCCCAG   GCTTTACACT   TTATGCTTCC   GGCTCGTATG   TTGTGTGGAA   6180
6181    TTGTGAGCGG   ATAACAATTT   CACACGCGTC   ACTTGGCACT   GGCCGTCGTT   TTACAACGTC   6240
6241    GTGACTGGGA   AAACCCTGGC   GTTACCCAAG   CTTTGTACAT   GGAGAAAATA   AAGTGAAACA   6300
6301    AAGCACTATT   GCACTGGCAC   TCTTACCGTT   ACTGTTTACC   CCTGTGGCAA   AAGCCCAGGT   6360
6361    CCAGCTGCTC   GAGTCGGTCT   TCCCCCTGGC   ACCCTCCTCC   AAGAGCACCT   CTGGGGGCAC   6420
6421    AGCGGCCCTG   GGCTGCCTGG   TCAAGACTAA   TTCCCCGAAC   CGGTGACGGT   GTCGTGGAAC   6480
6481    TCAGGCGCCC   TGACCAGCGG   CGTGCACACC   TTCCCGGCTG   TCCTACAGTC   CTCAGGACTC   6540
6541    TACTCCCTCA   GCAGCGTGGT   GACCGTGCCC   TCCAGCAGCT   TGGGCACCCA   GACCTACATC   6600
6601    TGCAACGTGA   ATCACAAGCC   CAGCAACACC   AAGGTGGACA   AGAAAGCAGA   GCCCAAATCT   6660
6661    TGTACTAGTG   GATCCTACCC   GTACGACGTT   CCGGACTACG   CTTCTTAGGC   TGAAGGCGAT   6720
6721    GACCCTGCTA   AGGCTGCATT   CAATAGTTTA   CAGGCAAGTG   CTACTGAGTA   CATTGGCTAC   6780
6781    GCTTGGGCTA   TGGTAGTAGT   TATAGTTGGT   GCTACCATAG   GGATTAAATT   ATTCAAAAAG   6840
6841    TTTACGAGCA   AGGCTTCTTA   AGCAATAGCG   AAGAGGCCCG   CACCGATCGC   CCTTCCCAAC   6900
6901    AGTTGCGCAG   CCTGAATGGC   GAATGGCGCT   TTGCCTGGTT   TCCGGCACCA   GAAGCGGTGC   6960
6961    CGGAAAGCTG   GCTGGAGTGC   GATCTTCCTG   AGGCCGATAC   GGTCGTCGTC   CCCTCAAACT   7020
7021    GGCAGATGCA   CGGTTACGAT   GCGCCCATCT   ACACCAACGT   AACCTATCCC   ATTACGGTCA   7080
7081    ATCCGCCGTT   TGTTCCCACG   GAGAATCCGA   CGGGTTGTTA   CTCGCTCACA   TTTAATGTTG   7140
7141    ATGAAAGCTG   GCTACAGGAA   GGCCAGACGC   GAATTATTTT   TGATGGCGTT   CCTATTGGTT   7200
7201    AAAAAATGAG   CTGATTTAAC   AAAAATTTAA   CGCGAATTTT   AACAAAATAT   TAACGTTTAC   7260
7261    AATTTAAATA   TTTGCTTATA   CAATCTTCCT   GTTTTTGGGG   CTTTTCTGAT   TATCAACCGG   7320
7321    GGTACATATG   ATTGACATGC   TAGTTTTACG   ATTACCGTTC   ATCGATTCTC   TTGTTTGCTC   7380
7381    CAGACTCTCA   GGCAATGACC   TGATAGCCTT   TGTAGATCTC   TCAAAAATAG   CTACCCTCTC   7440
7441    CGGCATTAAT   TTATCAGCTA   GAACGGTTGA   ATATCATATT   GATGGTGATT   TGACTGTCTC   7500
7501    CGGCCTTTCT   CACCCTTTTG   AATCTTTACC   TACACATTAC   TCAGGCATTG   CATTTAAAAT   7560
7561    ATATGAGGGT   TCTAAAAATT   TTTATCCTTG   CGTTGAAATA   AAGGCTTCTC   CCGCAAAAGT   7620
7621    ATTACAGGGT   CATAATGTTT   TTGGTACAAC   CGATTTAGCT   TTATGCTCTG   AGGCTTTATT   7680
7681    GCTTAATTTT   GCTAATTCTT   TGCCTTGCCT   GTATGATTTA   TTGGACGTT                7729
        |  10        |  20        |  30        |  40        |  50        |  60
```

FIG. 5C

```
     |   10      |   20      |   30      |   40      |   50      |   60
   1 AATGCTACTA CTATTAGTAG AATTGATGCC ACCTTTTCAG CTCGCGCCCC AAATGAAAAT   60
  61 ATAGCTAAAC AGGTTATTGA CCATTTGCGA AATGTATCTA ATGGTCAAAC TAAATCTACT  120
 121 CGTTCGCAGA ATTGGGAATC AACTGTTACA TGGAATGAAA CTTCCAGACA CCGTACTTTA  180
 181 GTTGCATATT TAAAACATGT TGAGCTACAG CACCAGATTC AGCAATTAAG CTCTAAGCCA  240
 241 TCTGCAAAAA TGACCTCTTA TCAAAAGGAG CAATTAAAGG TACTCTCTAA TCCTGACCTG  300
 301 TTGGAGTTTG CTTCCGGTCT GGTTCGCTTT GAAGCTCGAA TTAAAACGCG ATATTTGAAG  360
 361 TCTTTCGGGC TTCCTCTTAA TCTTTTTGAT GCAATCCGCT TTGCTTCTGA CTATAATAGT  420
 421 CAGGGTAAAG ACCTGATTTT TGATTTATGG TCATTCTCGT TTTCTGAACT GTTTAAAGCA  480
 481 TTTGAGGGGG ATTCAATGAA TATTTATGAC GATTCCGCAG TATTGGACGC TATCCAGTCT  540
 541 AAACATTTTA CTATTACCCC CTCTGGCAAA ACTTCTTTTG CAAAAGCCTC TCGCTATTTT  600
 601 GGTTTTTATC GTCGTCTGGT AAACGAGGGT TATGATAGTG TTGCTCTTAC TATGCCTCGT  660
 661 AATTCCTTTT GGCGTTATGT ATCTGCATTA GTTGAATGTG GTATTCCTAA ATCTCAACTG  720
 721 ATGAATCTTT CTACCTGTAA TAATGTTGTT CCGTTAGTTC GTTTTATTAA CGTAGATTTT  780
 781 TCTTCCCAAC GTCCTGACTG GTATAATGAG CCAGTTCTTA AAATCGCATA AGGTAATTCA  840
 841 CAATGATTAA AGTTGAAATT AAACCATCTC AAGCCCAATT TACTACTCGT TCTGGTGTTT  900
 901 CTCGTCAGGG CAAGCCTTAT TCACTGAATG AGCAGCTTTG TTACGTTGAT TTGGGTAATG  960
 961 AATATCCGGT TCTTGTCAAG ATTACTCTTG ATGAAGGTCA GCCAGCCTAT GCGCCTGGTC 1020
1021 TGTACACCGT TCATCTGTCC TCTTTCAAAG TTGGTCAGTT CGGTTCCCTT ATGATTGACC 1080
1081 GTCTGCGCCT CGTTCCGGCT AAGTAACATG GAGCAGGTCG CGGATTTCGA CACAATTTAT 1140
1141 CAGGCGATGA TACAAATCTC CGTTGTACTT TGTTTCGCGC TTGGTATAAT CGCTGGGGGT 1200
1201 CAAAGATGAG TGTTTTAGTG TATTCTTTCG CCTCTTTCGT TTTAGGTTGG TGCCTTCGTA 1260
1261 GTGGCATTAC GTATTTTACC CGTTTAATGG AAACTTCCTC ATGAAAAAGT CTTTAGTCCT 1320
1321 CAAAGCCTCT GTAGCCGTTG CTACCCTCGT TCCGATGCTG TCTTTCGCTG CTGAGGGTGA 1380
1381 CGATCCCGCA AAAGCGGCCT TTAACTCCCT GCAAGCCTCA GCGACCGAAT ATATCGGTTA 1440
1441 TGCGTGGGCG ATGGTTGTTG TCATTGTCGG CGCAACTATC GGTATCAAGC TGTTTAAGAA 1500
1501 ATTCACCTCG AAAGCAAGCT GATAAACCGA TACAATTAAA GGCTCCTTTT GGAGCCTTTT 1560
1561 TTTTTGGAGA TTTTCAACGT GAAAAAATTA TTATTCGCAA TTCCTTTAGT TGTTCCTTTC 1620
1621 TATTCTCACT CCGCTGAAAC TGTTGAAAGT TGTTTAGCAA AACCCCATAC AGAAAATTCA 1680
1681 TTTACTAACG TCTGGAAAGA CGACAAAACT TTAGATCGTT ACGCTAACTA TGAGGGTTGT 1740
1741 CTGTGGAATG CTACAGGCGT TGTAGTTTGT ACTGGTGACG AAACTCAGTG TTACGGTACA 1800
1801 TGGGTTCCTA TTGGGCTTGC TATCCCTGAA AATGAGGGTG GTGGCTCTGA GGGTGGCGGT 1860
1861 TCTGAGGGTG GCGGTTCTGA GGGTGGCGGT ACTAAACCTC CTGAGTACGG TGATACACCT 1920
1921 ATTCCGGGCT ATACTTATAT CAACCCTCTC GACGGCACTT ATCCGCCTGG TACTGAGCAA 1980
1981 AACCCCGCTA ATCCTAATCC TTCTCTTGAG GAGTCTCAGC CTCTTAATAC TTTCATGTTT 2040
2041 CAGAATAATA GGTTCCGAAA TAGGCAGGGG GCATTAACTG TTTATACGGG CACTGTTACT 2100
2101 CAAGGCACTG ACCCCGTTAA AACTTATTAC CAGTACACTC CTGTATCATC AAAAGCCATG 2160
2161 TATGACGCTT ACTGGAACGG TAAATTCAGA GACTGCGCTT TCCATTCTGG CTTTAATGAA 2220
2221 GATCCATTCG TTTGTGAATA TCAAGGCCAA TCGTCTGACC TGCCTCAACC TCCTGTCAAT 2280
2281 GCTGGCGGCG GCTCTGGTGG TGGTTCTGGT GGCGGCTCTG AGGGTGGTGG CTCTGAGGGT 2340
2341 GGCGGTTCTG AGGGTGGCGG CTCTGAGGGA GGCGGTTCCG GTGGTGGCTC TGGTTCCGGT 2400
2401 GATTTTGATT ATGAAAAGAT GGCAAACGCT AATAAGGGGG CTATGACCGA AAATGCCGAT 2460
2461 GAAAACGCGC TACAGTCTGA CGCTAAAGGC AAACTTGATT CTGTCGCTAC TGATTACGGT 2520
2521 GCTGCTATCG ATGGTTTCAT TGGTGACGTT TCCGGCCTTG CTAATGGTAA TGGTGCTACT 2580
2581 GGTGATTTTG CTGGCTCTAA TTCCCAAATG GCTCAAGTCG GTGACGGTGA TAATTCACCT 2640
2641 TTAATGAATA ATTTCCGTCA ATATTTACCT TCCCTCCCTC AATCGGTTGA ATGTCGCCCT 2700
2701 TTTGTCTTTA GCGCTGGTAA ACCATATGAA TTTTCTATTG ATTGTGACAA AATAAACTTA 2760
2761 TTCCGTGGTG TCTTTGCGTT TCTTTTATAT GTTGCCACCT TTATGTATGT ATTTTCTACG 2820
2821 TTTGCTAACA TACTGCGTAA TAAGGAGTCT TAATCATGCC ATGGCTTTTG GGTATTCCGT 2880
2881 TATTATTGCG TTTCCTCGGT TTCCTTCTGG TAACTTTGTT CGGCTATCTG CTTACTTTTC 2940
2941 TTAAAAAGGG CTTCGGTAAG ATAGCTATTG CTATTTCATT GTTTCTTGCT CTTATTATTG 3000
     |   10      |   20      |   30      |   40      |   50      |   60
```

FIG. 6A

```
        |   10       |   20       |   30       |   40       |   50       |   60
3001    GGCTTAACTC   AATTCTTGTG   GGTTATCTCT   CTGATATTAG   CGCTCAATTA   CCCTCTGACT   3060
3061    TTGTTCAGGG   TGTTCAGTTA   ATTCTCCCGT   CTAATGCGCT   TCCCTGTTTT   TATGTTATTC   3120
3121    TCTCTGTAAA   GGCTGCTATT   TTCATTTTTG   ACGTTAAACA   AAAAATCGTT   TCTTATTTGG   3180
3181    ATTGGGATAA   ATAATATGGC   TGTTTATTTT   GTAACTGGCA   AATTAGGCTC   TGGAAAGACG   3240
3241    CTCGTTAGCG   TTGGTAAGAT   TCAGGATAAA   ATTGTAGCTG   GGTGCAAAAT   AGCAACTAAT   3300
3301    CTTGATTTAA   GGCTTCAAAA   CCTCCCGCAA   GTCGGGAGGT   TCGCTAAAAC   GCCTCGCGTT   3360
3361    CTTAGAATAC   CGGATAAGCC   TTCTATATCT   GATTTGCTTG   CTATTGGGCG   CGGTAATGAT   3420
3421    TCCTACGATG   AAAATAAAAA   CGGCTTGCTT   GTTCTCGATG   AGTGCGGTAC   TTGGTTTAAT   3480
3481    ACCCGTTCTT   GGAATGATAA   GGAAAGACAG   CCGATTATTG   ATTGGTTTCT   ACATGCTCGT   3540
3541    AAATTAGGAT   GGGATATTAT   TTTTCTTGTT   CAGGACTTAT   CTATTGTTGA   TAAACAGGCG   3600
3601    CGTTCTGCAT   TAGCTGAACA   TGTTGTTTAT   TGTCGTCGTC   TGGACAGAAT   TACTTTACCT   3660
3661    TTTGTCGGTA   CTTTATATTC   TCTTATTACT   GGCTCGAAAA   TGCCTCTGCC   TAAATTACAT   3720
3721    GTTGGCGTTG   TTAAATATGG   CGATTCTCAA   TTAAGCCCTA   CTGTTGAGCG   TTGGCTTTAT   3780
3781    ACTAAGTAAGA  ATTTGTATAA   CGCATATGAT   ACTAAACAGG   CTTTTTCTAG   TAATTATGAT   3840
3841    TCCGGTGTTT   ATTCTTATTT   AACGCCTTAT   TTATCACACG   GTCGGTATTT   CAAACCATTA   3900
3901    AATTTAGGTC   AGAAGATGAA   GCTTACTAAA   ATATATTTGA   AAAAGTTTTC   ACGCGTTCTT   3960
3961    TGTCTTGCGA   TTGGATTTGC   ATCAGCATTT   ACATATAGTT   ATATAACCCA   ACCTAAGCCG   4020
4021    GAGGTTAAAA   AGGTAGTCTC   TCAGACCTAT   GATTTTGATA   AATTCACTAT   TGACTCTTCT   4080
4081    CAGCGTCTTA   ATCTAAGCTA   TCGCTATGTT   TTCAAGGATT   CTAAGGGAAA   ATTAATTAAT   4140
4141    AGCGACGATT   TACAGAAGCA   AGGTTATTCA   CTCACATATA   TTGATTTATG   TACTGTTTCC   4200
4201    ATTAAAAAAG   GTAATTCAAA   TGAAATTGTT   AAATGTAATT   AATTTTGTTT   TCTTGATGTT   4260
4261    TGTTTCATCA   TCTTCTTTTG   CTCAGGTAAT   TGAAATGAAT   AATTCGCCTC   TGCGCGATTT   4320
4321    TGTAACTTGG   TATTCAAAGC   AATCAGGCGA   ATCCGTTATT   GTTTCTCCCG   ATGTAAAAGG   4380
4381    TACTGTTACT   GTATATTCAT   CTGACGTTAA   ACCTGAAAAT   CTACGCAATT   TCTTTATTTC   4440
4441    TGTTTTACGT   GCTAATAATT   TTGATATGGT   TGGTTCAATT   CCTTCCATAA   TTCAGAAGTA   4500
4501    TAATCCAAAC   AATCAGGATT   ATATTGATAA   ATTGCATCA   TCTGATAATC   AGGAATATGA   4560
4561    TGATAATTCC   GCTCCTTCTG   GTGGTTTCTT   TGTTCCGCAA   AATGATAATG   TTACTCAAAC   4620
4621    TTTTAAAATT   AATAACGTTC   GGGCAAAGGA   TTTAATACGA   GTTGTCGAAT   TGTTTGTAAA   4680
4681    GTCTAATACT   TCTAAATCCT   CAAATGTATT   ATCTATTGAC   GGCTCTAATC   TATTAGTTGT   4740
4741    TAGTGCACCT   AAAGATATTT   TAGATAACCT   TCCTCAATTC   CTTTCTACTG   TTGATTTGCC   4800
4801    AACTGACCAG   ATATTGATTG   AGGGTTTGAT   ATTTGAGGTT   CAGCAAGGTG   ATGCTTTAGA   4860
4861    TTTTTCATTT   GCTGCTGGCT   CTCAGCGTGG   CACTGTTGCA   GGCGGTGTTA   ATACTGACCG   4920
4921    CCTCACCTCT   GTTTTATCTT   CTGCTGGTGG   TTCGTTCGGT   ATTTTTAATG   GCGATGTTTT   4980
4981    AGGGCTATCA   GTTCGCGCAT   TAAAGACTAA   TAGCCATTCA   AAAATATTGT   CTCTGCCACG   5040
5041    TATTCTTACG   CTTTCAGGTC   AGAAGGGTTC   TATCTCTGTT   GGCCAGAATG   TCCCTTTTAT   5100
5101    TACTGGTCGT   GTGACTGGTG   AATCTGCCAA   TGTAAATAAT   CCATTTCAGA   CGATTGAGCG   5160
5161    TCAAAATGTA   GGTATTTCCA   TGAGCGTTTT   TCCTGTTGCA   ATGGCTGGCG   GTAATATTGT   5220
5221    TCTGGATATT   ACCAGCAAGG   GCGATAGTTT   GAGTTCTTCT   ACTCAGGCAA   GTGATGTTAT   5280
5281    TACTAATCAA   AGAAGTATTG   CTACAACGGT   TAATTTGCGT   GATGGACAGA   CTCTTTTACT   5340
5341    CGGTGGCCTC   ACTGATTATA   AAAACACTTC   TCAAGATTCT   GGCGTACCGT   TCCTGTCTAA   5400
5401    AATCCCTTTA   ATCGGCCTCC   TGTTTAGCTC   CCGCTCTGAT   TCCAACGAGG   AAAGCACGTT   5460
5461    ATACGTGCTC   GTCAAAGCAA   CCATAGTACG   CGCCCTGTAG   CGGCGCATTA   AGCGCGGCGG   5520
5521    GTGTGGTGGT   TACGCGCAGC   GTGACCGCTA   CACTTGCCAG   CGCCCTAGCG   CCCGCTCCTT   5580
5581    TCGCTTTCTT   CCCTTCCTTT   CTCGCCACGT   TCGCCGGCTT   TCCCCGTCAA   GCTCTAAATC   5640
5641    GGGGGCTCCC   TTTAGGGTTC   CGATTTAGTG   CTTTACGGCA   CCTCGACCCC   AAAAAACTTG   5700
5701    ATTTGGGTGA   TGGTTCACGT   AGTGGGCCAT   CGCCCTGATA   GACGGTTTTT   CGCCCTTTGA   5760
5761    CGTTGGAGTC   CACGTTCTTT   AATAGTGGAC   TCTTGTTCCA   AACTGGAACA   ACACTCAACC   5820
5821    CTATCTCGGG   CTATTCTTTT   GATTTATAAG   GGATTTTGCC   GATTTCGGAA   CCACCATCAA   5880
5881    ACAGGATTTT   CGCCTGCTGG   GGCAAACCAG   CGTGGACCGC   TTGCTGCAAC   TCTCTCAGGG   5940
5941    CCAGGCGGTG   AAGGGCAATC   AGCTGTTGCC   CGTCTCGCTG   GTGAAAAGAA   AAACCACCCT   6000
        |   10       |   20       |   30       |   40       |   50       |   60
```

FIG. 6B

```
       |   10         |   20         |   30         |   40         |   50         |   60
6001   GGCGCCCAAT    ACGCAAACCG    CCTCTCCCCG    CGCGTTGGCC    GATTCATTAA    TGCAGCTGGC    6060
6061   ACGACAGGTT    TCCCGACTGG    AAAGCGGGCA    GTGAGCGCAA    CGCAATTAAT    GTGAGTTAGC    6120
6121   TCACTCATTA    GGCACCCCAG    GCTTTACACT    TTATGCTTCC    GGCTCGTATG    TTGTGTGGAA    6180
6181   TTGTGAGCGG    ATAACAATTT    CACACGCCAA    GGAGACAGTC    ATAATGAAAT    ACCTATTGCC    6240
6241   TACGGCAGCC    GCTGGATTGT    TATTACTCGC    TGCCCAACCA    GCCATGGCCG    AGCTCTTCCC    6300
6301   GCCATCTGAT    GAGCAGTTGA    AATCTGGAAC    TGCCTCTGTT    GTGTGCCTGC    TGAATAACTT    6360
6361   CTATCCCAGA    GAGGCCAAAG    TACAGTGGAA    GGTGGATAAC    GCCCTCCAAT    CGGGTAACTC    6420
6421   CCAGGAGAGT    GTCACAGAGC    AGGACAGCAA    GGACAGCACC    TACAGCCTCA    GCAGCACCCT    6480
6481   GACGCTGAGC    AAAGCAGACT    ACGAGAAACA    CAAAGTCTAC    GCCTGCGAAG    TCACCCATCA    6540
6541   GGGCCTGAGC    TCGCCCGTCA    CAAAGAGCTT    CAACAGGGGA    GAGTGTTCTA    GAACGCGTCA    6600
6601   CTTGGCACTG    GCCGTCGTTT    TACAACGTCG    TGACTGGGAA    AACCCTGGCG    TTACCCAAGC    6660
6661   TTTGTACATG    GAGAAAATAA    AGTGAAACAA    AGCACTATTG    CACTGGCACT    CTTACCGTTA    6720
6721   CTGTTTACCC    CTGTGGCAAA    AGCCGCCTCC    ACCAAGGGCC    CATCGGTCTT    CCCCCTGGCA    6780
6781   CCCTCCTCCA    AGAGCACCTC    TGGGGGCACA    GCGGCCCTGG    GCTGCCTGGT    CAAGACTAAT    6840
6841   TCCCCGAACC    GGTGACGGTG    TCGTGGAACT    CAGGCGCCCT    GACCAGCGGC    GTGCACACCT    6900
6901   TCCCGGCTGT    CCTACAGTCC    TCAGGACTCT    ACTCCCTCAG    CAGCGTGGTG    ACCGTGCCCT    6960
6961   CCAGCAGCTT    GGGCACCCAG    ACCTACATCT    GCAACGTGAA    TCACAAGCCC    AGCAACACCA    7020
7021   AGGTGGACAA    GAAAGCAGAG    CCCAAATCTT    GTACTAGTGG    ATCCTACCCG    TACGACGTTC    7080
7081   CGGACTACGC    TTCTTAGGCT    GAAGGCGATG    ACCCTGCTAA    GGCTGCATTC    AATAGTTTAC    7140
7141   AGGCAAGTGC    TACTGAGTAC    ATTGGCTACG    CTTGGGCTAT    GGTAGTAGTT    ATAGTTGGTG    7200
7201   CTACCATAGG    GATTAAATTA    TTCAAAAAGT    TTACGAGCAA    GGCTTCTTAA    GCAATAGCGA    7260
7261   AGAGGCCCGT    ACCGATCGCC    CTTCCCAACA    GTTGCGCAGC    CTGAATGGCG    AATGGCGCTT    7320
7321   TGCCTGGTTT    CAAAAATAGC    TACCCTCTCC    GGAAAGCTGG    GTGGAGTGCG    ATCTTCCTGA    7380
7381   GGCCGATACG    GTCGTCGTCC    CCTCAAACTG    GCAGATGCAC    GGTTACGATG    CGCCCATCTA    7440
7441   CACCAACGTA    ACCTATCCCA    TTACGGTCAA    TCCGCCGTTT    GTTCCCACGG    AGAATCCGAC    7500
7501   GGGTTGTTAC    TCGCTCACAT    TTAATGTTGA    TGAAAGCTGG    CTACAGGAAG    GCCAGACGCG    7560
7561   AATTATTTTT    GATGGCGTTC    CTATTGGTTA    AAAAATGAGC    TGATTTAACA    AAAATTTAAC    7620
7621   GCGAATTTTA    ACAAAATATT    AACGTTTACA    ATTTAAATAT    TTGCTTATAC    AATCTTCCTG    7680
7681   TTTTTGGGGC    TTTTCTGATT    ATCAACCGGG    GTACATATGA    TTGACATGCT    AGTTTTACGA    7740
7741   TTACCGTTCA    TCGATTCTCT    TGTTTGCTCC    AGACTCTCAG    GCAATGACCT    GATAGCCTTT    7800
7801   GTAGATCTCT    CAAAAATAGC    TACCCTCTCC    GGCATTAATT    TATCAGCTAG    AACGGTTGAA    7860
7861   TATCATATTG    ATGGTGATTT    GACTGTCTCC    GGCCTTTCTC    ACCCTTTTGA    ATCTTTACCT    7920
7921   ACACATTACT    CAGGCATTGC    ATTTAAAATA    TATGAGGGTT    CTAAAAATTT    TTATCCTTGC    7980
7981   GTTGAAATAA    AGGCTTCTCC    CGCAAAAGTA    TTACAGGGTC    ATAATGTTTT    TGGTACAACC    8040
8041   GATTTAGCTT    TATGCTCTGA    GGCTTTATTG    CTTAATTTTG    CTAATTCTTT    GCCTTGCCTG    8100
8101   TATGATTTAT    TGGACGTT                                                              8118
       |   10         |   20         |   30         |   40         |   50         |   60
```

SURFACE EXPRESSION LIBRARIES OF HETEROMERIC RECEPTORS

This application is a continuation of application Ser. No. 08/349,131, filed Dec. 2, 1994, now U.S. Pat. No. 5,871,974, which is a continuation of application Ser. No. 08/120,648, filed Sep. 13, 1993, now abandoned, which is a continuation of application Ser. No. 07/767,136, filed Sep. 27, 1991, now abandoned which is a continuation-in-part of application Ser. No. 07/590,219, filed Sep. 28, 1990, now abandoned.

BACKGROUND OF THE INVENTION

This invention relates generally to recombinant expression of heteromeric receptors and, more particularly, to expression of such receptors on the surface of filamentous bacteriophage.

Antibodies are heteromeric receptors generated by a vertebrates organism's immune system which bind to an antigen. The molecules are composed of two heavy and two light chains disulfide bonded together. Antibodies have the appearance of a "Y"-shaped structure and the antigen binding portion being located at the end of both short arms of the Y. The region on the heavy and light chain polypeptides which corresponds to the antigen binding portion is known as variable region. The differences between antibodies within this region are primarily responsible for the variation in binding specificities between antibody molecules. The binding specificities are a composite of the antigen interactions with both heavy and light chain polypeptides.

The immune system has the capability of generating an almost infinite number of different antibodies. Such a large diversity is generated primarily through recombination to form the variable regions of each chain and through differential pairing of heavy and light chains. The ability to mimic the natural immune system and generate antibodies that bind to any desired molecule is valuable because such antibodies can be used for diagnostic and therapeutic purposes.

Until recently, generation of antibodies against a desired molecule was accomplished only through manipulation of natural immune responses. Methods included classical immunization techniques of laboratory animals and monoclonal antibody production. Generation of monoclonal antibodies is laborious and time consuming. It involves a series of different techniques and is only performed on animal cells. Animal cells have relatively long generation times and require extra precautions to be taken compared to procaryotic cells to ensure viability of the cultures.

A method for the generation of a large repertoire of diverse antibody molecules in bacteria has been described, Huse et al., Science, 246, 1275–1281 (1989), which is herein incorporated by reference. The method uses the bacteriophage lambda as the vector. The lambda vector is a long, linear double-stranded DNA molecule. Production of antibodies using this vector involves the cloning of heavy and light chain populations of DNA sequences into separate vectors. The vectors are subsequently combined randomly to form a single vector which directs the coexpression of heavy and light chains to form antibody fragments. A disadvantage to this method is that undesired combinations of vector portions are brought together when generating the coexpression vector. Although these undesired combinations do not produce viable phage, they do however, result in a significant loss of sequences from the population and, therefore, a loss in diversity of the number of different combinations which can be obtained between heavy and light chains. Additionally, the size of the lambda phage gen is large compared to the genes that encode the antibody segments. This makes the lambda system inherently more difficult to manipulate as compared to other available vector systems.

There thus exists a need for a method to generate diverse populations of heteromeric receptors which mimics the natural immune system, which is fast and efficient and results in only desired combinations without loss of diversity. The present invention satisfies these needs and provides related advantages as well.

SUMMARY OF THE INVENTION

The invention relates to a plurality of cells containing diverse combinations of first and second DNA sequences encoding first and second polypeptides which form a heteromeric receptor, said heteromeric receptors being expressed on the surface of a cell, preferably one which produces filamentous bacteriophage, such as M13. Vectors, cloning systems and methods of making and screening the heteromeric receptors are also provided.

BRIEF DESCRIPTION OF THE DRAWINGS

FIG. 1C shows the joining of vector population from heavy and light chain libraries to form the functional surface expression vector M13IXHL. FIG. 1D shows the generation of a surface expression library in a non-suppressor strain and the production of phage. The phage are used to infect a suppressor strain (FIG. 1E) for surface expression and screening of the library.

FIGS. 2A, 2B and 2C is the nucleotide sequence of M13IX30 (SEQ ID NO: 1).

FIGS. 3A, 3B and 3C is the nucleotide sequence of M13IX11 (SEQ ID NO:2).

FIGS. 4A, 4B and 4C is the nucleotide sequence of M13IX34 (SEQ ID NO: 3).

FIGS. 5A, 5B and 5C is the nucleotide sequence of M13IX13 (SEQ ID NO: 4).

FIGS. 6A, 6B and 6C is the nucleotide sequence of M13IX60 (SEQ ID NO: 5).

DETAILED DESCRIPTION OF THE INVENTION

Figure 1:
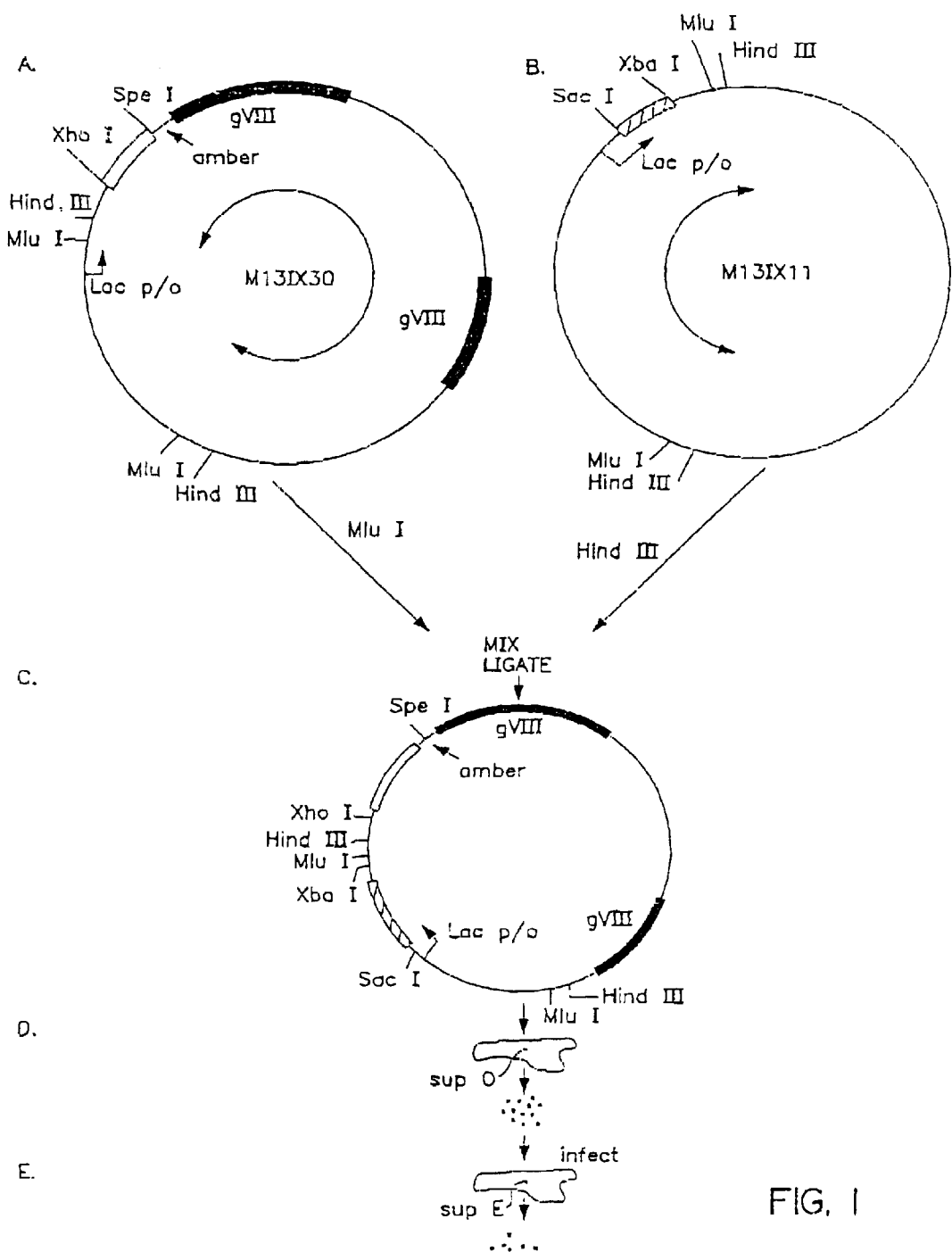
FIG. 1 is a schematic diagram of the two vectors used for surface expression library construction from heavy and light chain libraries. M13IX30 (FIG. 1A) is the vector used to clone the heavy chain sequences (open box). The single-headed arrow represents the Lac p/o expression sequences and the double-headed arrow represents the portion of M13IX30 which is to be combined with M13IX11. The amber stop codon and relevant restriction sites are also shown. M13IX11 (FIG. 1B) is the vector used to clone the light chain sequences (hatched box). Thick lines represent the pseudo-wild type (ψ gVIII) and wild type (gVIII) gene VIII sequences. The double-headed arrow represents the portion of M13IX11 which is to be combined with M13IX30. Relevant restriction sites are also shown.

This invention is directed to simple and efficient methods to generate a large repertoire of diverse combinations of heteromeric receptors. The method is advantageous in that only proper combinations of vector portions are randomly brought together for the coexpression of different DNA sequences without loss of population size or diversity. The receptors can be expressed on the surface of cells, such as those producing filamentous bacteriophage, which can be screened in large numbers. The nucleic acid sequences encoding the receptors can be readily characterized because the filamentous bacteriophage produce single strand DNA for efficient sequencing and mutagenesis methods. The heteromeric receptors so produced are useful in an unlimited number of diagnostic and therapeutic procedures.

In one embodiment, two populations of diverse heavy (Hc) and light (Lc) chain sequences are synthesized by polymerase chain reaction (PCR). These populations are cloned into separate M13-based vectors containing elements necessary for expression. The heavy chain vector contains a gene VIII (gVIII) coat protein sequence so that translation of the Hc sequences produces gVIII-Hc fusion proteins. The populations of the two vectors are randomly combined such that only the vector portions containing the Hc and Lc sequences are joined into a single circular vector. The combined vector directs the coexpression of both Hc and Lc sequences for assembly of the two polypeptides and surface expression on M13. A mechanism also exists to control the expression of gVIII-Hc fusion proteins during library construction and screening.

As used herein, the term "heteromeric receptors" refers to proteins composed of two or more subunits which together exhibit binding activity toward particular molecules. It is understood that the term includes the subunit fragments so long as assembly of the polypeptides and function of the assembled complex is retained. Heteromeric receptors include, for example, antibodies and fragments thereof such as Fab and (Fab)$_2$ portions, T cell receptors, integrins, hormone receptors and transmitter receptors.

As used herein, the term "preselected molecule" refers to a molecule which is chosen from a number of choices. The molecule can be, for example, a protein or peptide, or an organic molecule such as a drug. Benzodiazapam is a specific example of a preselected molecule.

As used herein, the term "coexpression" refers to the expression of two or more nucleic acid sequences usually expressed as separate polypeptides. For heteromeric receptors, the coexpressed polypeptides assemble to form the heteromer. Therefore, "expression elements" as used herein, refers to sequences necessary for the transcription, translation, regulation and sorting of the expressed polypeptides which mak up the heteromeric receptors. The term also includes the expression of two subunit polypeptides which are linked but are able to assemble into a heteromeric receptor. A specific example of coexpression of linked polypeptides is where Hc and Lc polypeptides are expressed with a flexible peptide or polypeptide linker joining the two subunits into a single chain. The linker is flexible enough to allow association of Hc and Lc portions into a functional Fab fragment.

The invention provides for a composition of matter comprising a plurality of procaryotic cells containing diverse combinations of first and second DNA sequences encoding first and second polypeptides which form a heteromeric receptor exhibiting binding activity toward a preselected molecule, said heteromeric receptors being expressed on the surface of filamentous bacteriophage.

DNA sequences encoding the polypeptides of heteromeric receptors are obtained by methods known to one skilled in the art. Such methods include, for example, cDNA synthesis and polymerase chain reaction (PCR). The need will determine which method or combination of methods is to be used to obtain the desired populations of sequences. Expression can be performed in any compatible vector/host system. Such systems include, for example, plasmids or phagemids in procaryotes such as E. coli, yeast systems and other eucaryotic systems such as mammalian cells, but will be described herein in context with its presently preferred embodiment, i.e. expression on the surface of filamentous bacteriophage. Filamentous bacteriophage include, for example, M13, fl and fd. Additionally, the heteromeric receptors can also be expressed in soluble or secreted form depending on the need and the vector/host system employed.

Expression of heteromeric receptors such as antibodies or functional fragments thereof on the surface of M13 can be accomplished, for example, using the vector system shown in FIG. 1. Construction of the vectors enabling one of ordinary skill to make them are explicitly set out in Example I. The complete nucleotide sequences are given in FIGS. 2A, 2B and 2C and FIGS. 3A, 3B and 3C (SEQ ID NOS: 1 and 2). This system produces randomly combined populations of heavy (Hc) and light (Lc) chain antibody fragments functionally linked to expression elements. The Hc polypeptide is produced as a fusion protein with the M13 coat protein encoded by gene VIII. The gVIII-Hc fusion protein therefore anchors the assembled Hc and Lc polypeptides on the surface of M13. The diversity of Hc and Lc combinations obtained by this system can be $5 \times 10^7$ or greater. Diversity of less than $5 \times 10^7$ can also be obtained and will be determined by the need and type of heteromeric receptor to be expressed.

Populations of Hc and Lc encoding sequences to be combined into a vector for coexpression are each cloned into separate vectors. For the vectors shown in FIG. 1, diverse populations of sequences encoding Hc polypeptides are cloned into M13IX30 (SEQ ID NO: 1). Sequences encoding Lc polypeptides are cloned into M13IX11 (SEQ ID NO: 2). The populations are inserted between the Xho I-Spe I or Stu I restriction enzyme sites in M13IX30 and between the Sac I-Xba I or Eco RV sites in M13IX11 (FIGS. 1A and B, respectively).

The populations of Hc and Lc sequences inserted into the vectors can be synthesized with appropriate restriction recognition sequences flanking opposite ends of the encoding sequences but this is not necessary. The sites allow annealing and ligation in-frame with expression elements of these sequences into a double-stranded vector restricted with the appropriate restriction enzyme. Alternatively, and a preferred embodiment, the Hc and Lc sequences can be inserted into the vector without restriction of the DNA. This method of cloning is beneficial because naturally encoded restriction enzyme sites may be present within the sequences, thus, causing destruction of the sequence when treated with a restriction enzyme. For cloning without restriction, the sequences are treated briefly with a 3' to 5' exonuclease such as T4 DNA polymerase or exonuclease III. A 5' to 3' exonuclease will also accomplish the same function. The protruding 5' termini which remains should be complementary to single-stranded overhangs within the vector which remain after restriction at the cloning site and treatment with exonuclease. The exonuclease treated inserts are annealed with the restricted vector by methods known to one skilled in the art. The exonuclease method decreases background and is easier to perform.

The vector used for Hc populations, M13IX30 (FIG. 1A; SEQ ID NO: 1) contains, in addition to expression elements, a sequence encoding the pseudo-wild type gVIII product downstream and in frame with the cloning sites. This gene encodes the wild type M13 gVIII amino acid sequence but has been changed at the nucleotide level to reduce homologous recombination with the wild type gVIII contained on the same vector. The wild type gVIII is present to ensure that at least some functional, non-fusion coat protein will be produced. The inclusion of a wild type gVIII therefore reduces the possibility of non-viable phage production and biological selection against certain peptide fusion proteins. Differential regulation of the two genes can also be used to control the relative ratio of the pseudo and wild type proteins.

Also contained downstream and in frame with the cloning sites is an amber stop codon. The stop codon is located between the inserted Hc sequences and the gVIII sequence and is in frame. As was the function of the wild type gVIII, the amber stop codon also reduces biological selection when combining vector portions to produce functional surface expression vectors. This is accomplished by using a non-suppressor (sup O) host strain because the non-suppressor strains will terminate expression after the Hc sequences but before the pseudo gVIII sequences. Therefore, the pseudo gVIII will essentially never be expressed on the phage surface under these circumstances. Instead, only soluble Hc polypeptides will be produced. Expression in a non-suppressor host strain can be advantageously utilized when one wishes to produce large populations of antibody fragments. Stop codons other than amber, such as opal and ochre, or molecular switches, such as inducible repressor elements, can also be used to unlink peptide expression from surface expression.

The vector used for Lc populations, M13IX11 (SEQ ID NO: 2), contains necessary expression elements and cloning sites for the Lc sequences, FIG. 1B. As with M13IX30, upstream and in frame with the cloning sites is a leader sequence for sorting to the phage surface. Additionally, a ribosome binding site and Lac Z promoter/operator elements are also present for transcription and translation of the DNA sequences.

Both vectors contain two pairs of Mlu I-Hind III restriction enzyme sites (FIGS. 1A and B) for joining together the Hc and Lc encoding sequences and their associated vector sequences. Mlu I and Hind III are non-compatible restriction sites. The two pairs are symmetrically orientated about the cloning site so that only the vector portions containing the sequences to be expressed are exactly combined into a single vector. The two pairs of sites are oriented identically with respect to one another on both vectors and the DNA between the two sites must be homologous enough between both vectors to allow annealing. This orientation allows cleavage of each circular vector into two portions and combination of essential components within each vector into a single circular vector where the encoded polypeptides can be coexpressed (FIG. 1C).

Any two pairs of restriction enzyme sites can be used so long as they are symmetrically orientated about the cloning site and identically orientated on both vectors. The sites within each pair, however, should be non-identical or able to be made differentially recognized as a cleavage substrate. For example, the two pairs of restriction sites contained within the vectors shown in FIG. 1 are Mlu I and Hind III. The sites are differentially cleavable by Mlu I and Hind III respectively. One skilled in the art knows how to substitute alternative pairs of restriction enzyme sites for the Mlu I-Hind III pairs described above. Also, instead of two Hind III and two Mlu I sites, a Hind III and Not I site can be paired with a Mlu I and a Sal I site, for example.

The combining step randomly brings together different Hc and Lc encoding sequences within the two diverse populations into a single vector (FIG. 1C; M13IXHL). The vector sequences donated from each independent vector, M13IX30 and M13IX11, are necessary for production of viable phage. Also, since the pseudo gVIII sequences are contained in M13IX30, coexpression of functional antibody fragments as Lc associated gVIII-Hc fusion proteins cannot be accomplished on the phage surface until the vector sequences are linked as shown in M13IXHL.

The combining step is performed by restricting each population of Hc and LC containing vectors with Mlu I and Hind III, respectively. The 3' termini of each restricted vector population is digested with a 3' to 5' exonuclease as described above for inserting sequences into the cloning sites. The vector populations are mixed, allowed to anneal and introduced into an appropriate host. A non-suppressor host (FIG. 1D) is preferably used during initial construction of the library to ensure that sequences are not selected against due to expression as fusion proteins. Phage isolated from the library constructed in a non-suppressor strain can be used to infect a suppressor strain for surface expression of antibody fragments.

A method for selecting a heteromeric receptor exhibiting binding activity toward a preselected molecule from a population of diverse heteromeric receptors, comprising: (a) operationally linking to a first vector a first population of diverse DNA sequences encoding a diverse population of first polypeptides, said first vector having two pairs of restriction sites symmetrically oriented about a cloning site; (b) operationally linking to a second vector a second population of diverse DNA sequences encoding a diverse population of second polypeptides, said second vector having two pairs of restriction sites symmetrically oriented about a cloning site in an identical orientation to that of the first vector: (c) combining the vector products of step (a) and (b) under conditions which allow only the operational combination of vector sequences containing said first and second DNA sequences; (d) introducing said population of combined vectors into a compatible host under conditions sufficient for expressing said population of first and second DNA sequences; and (e) determining the heteromeric receptors which bind to said preselected molecule. The invention also provides for determining the nucleic acid sequences encoding such polypeptides as well.

Surface expression of the antibody library is performed in an amber suppressor strain. As described above, the amber stop codon between the Hc sequence and the gVIII sequence unlinks the two components in a non-suppressor strain. Isolating the phage produced from the non-suppressor strain and infecting a suppressor strain will link the Hc sequences to the gVIII sequence during expression (FIG. 1E). Culturing the suppressor strain after infection allows the coexpression on the surface of M13 of all antibody species within the library as gVIII fusion proteins (gVIII-Fab fusion proteins). Alternatively, the DNA can be isolated from the non-suppressor strain and then introduced into a suppressor strain to accomplish the same effect.

The level of expression of gVIII-Fab fusion proteins can additionally be controlled at the transcriptional level. Both polypeptides of the gVIII-Fab fusion proteins are under the inducible control of the Lac Z promoter/operator system. Other inducible promoters can work as well and are known by one skilled in the art. For high levels of surface expression, the suppressor library is cultured in an inducer of the Lac Z promoter such as isopropylthio-β-galactoside (IPTG). Inducible control is beneficial because biological selection against non-functional gVIII-Fab fusion proteins can be minimized by culturing the library under non-expressing conditions. Expression can then be induced only at the time of screening to ensure that the entire population of antibodies within the library are accurately represented on the phage surface. Also, this can be used to control the valency of the antibody on the phage surface.

The surface expression library is screened for specific Fab fragments which bind preselected molecules by standard affinity isolation procedures. Such methods include, for example, panning, affinity chromatography and solid phase blotting procedures. Panning as described by Parmley and Smith, Gene 73:305–318 (1988), which is incorporated herein by reference, is preferred because high titers of phage can be screened easily, quickly and in small volumes. Furthermore, this procedure can select minor Fab fragments species within the population, which otherwise would have been undetectable, and amplified to substantially homogenous populations. The selected Fab fragments can be characterized by sequencing the nucleic acids encoding the polypeptides after amplification of the phage population.

The following examples are intended to illustrate but not limit the invention.

EXAMPLE I

Construction, Expression and Screening of Antibody Fragments on the Surface of M13

This example shows the synthesis of a diverse population of heavy (Hc) and light (Lc) chain antibody fragments and their expression on the surface of M13 as gene VIII-Fab fusion proteins. The expressed antibodies derive from the random mixing and coexpression of a Hc and Lc pair. Also demonstrated is the isolation and characterization of the expressed Fab fragments which bind benzodiazapam (BDP) and their corresponding nucleotide sequence.

Isolation of mRNA and PCR Anplification of Antibody Fragments

The surface expression library is constructed from mRNA isolated from a mouse that had been immunized with KLH-coupled benzodiazapam (BDP). BDP was coupled to keyhole limpet hemocyanin (KLH) using the techniques described in *Antibodies: A Laboratory Manual*, Harlow and Lane, eds., Cold Spring Harbor, N.Y. (1988), which is incorporated herein by reference. Briefly, 10.0 milligrams (mg) of keyhole limpet hemocyanin and 0.5 mg of BDP with a glutaryl spacer arm N-hydroxysuccinimide linker appendages. Coupling was performed as in Jonda et al., *Science*, 241:1188 (1988), which is incorporated herein by reference. The KLH-BDP conjugate was removed by gel filtration chromatography through Sephadex G-25.

The KLH-BDP conjugate was prepared for injection into mice by adding 100 $\mu$g of the conjugate to 250 $\mu$l of phosphate buffered saline (PBS). An equal volume of complete Freund's adjuvant was added and emulsified the entire solution for 5 minutes. Mice were injected with 300 $\mu$l of the emulsion. Injections were given subcutaneously at several sites using a 21 gauge needle. A second immunization with BDP was given two weeks later. This injection was prepared as follows: 50 $\mu$g of BDP was diluted in 250 $\mu$l of PBS and an equal volume of alum was mixed with the solution. The mice were injected intraperitoneally with 500 $\mu$l of the solution using a 23 gauge needle. One month later the mice were given a final injection of 50 $\mu$g of the conjugate diluted to 200 $\mu$l in PBS. This injection was given intravenously in the lateral tail vein using a 30 gauge needle. Five days after this final injection the mice were sacrificed and total cellular RNA was isolated from their spleens.

Total RNA was isolated from the spleen of a single mouse immunized as described above by the method of Chomczynski and Sacchi, *Anal. Biochem.*, 162:156–159 (1987), which is incorporated herein by reference. Briefly, immediately after removing the spleen from the immunized mouse, the tissue was homogenized in 10 ml of a denaturing solution containing 4.0 H guanine isothiocyanate, 0.25 M sodium citrate at pH 7.0, and 0.1 M 2-mercaptoethanol using a glass homogenizer. One ml of sodium acetate at a concentration of 2 M at pH 4.0 was mixed with the homogenized spleen. One ml of saturated phenol was also mixed with the denaturing solution containing the homogenized spleen. Two ml of a chloroform:isoamyl alcohol (24:1 v/v) mixture was added to this homogenate. The homogenate was mixed vigorously for ten seconds and maintained on ice for 15 minutes. The homogenate was then transferred to a thick-walled 50 ml polypropylene centrifuge tube (Fisher Scientific Company, Pittsburgh, Pa.). The solution was centrifuged at 10,000×g for 20 minutes at 4° C. The upper RNA-containing aqueous layer was transferred to a fresh 50 ml polypropylene centrifuge tube and mixed with an equal volume of isopropyl alcohol. This solution was maintained at −20° C. for at least one hour to precipitate the RNA. The solution containing the precipitated RNA was centrifuged at 10,000×g for twenty minutes at 4° C. The pelleted total cellular RNA was collected and dissolved in 3 ml of the denaturing solution described above. Three mls of isopropyl alcohol was added to the resuspended total cellular RNA and vigorously mixed. This solution was maintained at −20° C. for at least 1 hour to precipitate the RNA. The solution containing the precipitated RNA was centrifuged at 10,000×g for ten minutes at 4° C. The pelleted RNA was washed once with a solution containing 75% ethanol. The pelleted RNA was dried under vacuum for 15 minutes and then resuspended in dimethyl pyrocarbonate (DEPC) treated (DEPC-H$_2$O) H$_2$O.

Poly A$^{30}$ RNA for use in first strand cDNA synthesis was prepared from the above isolated total RNA using a spin-column kit (Pharmacia, Piscataway, N.J.) as recommended by the manufacturer. The basic methodology has been described by Aviv and Leder, *Proc. Natl. Acad. Sci., USA*, 69:1408–1412 (1972), which is incorporated herein by reference. Briefly, one half of the total RNA isolated from a single immunized mouse spleen prepared as described above was resuspended in one ml of DEPC-treated dH$_2$O and maintained at 65° C. for five minutes. One ml of 2×high salt loading buffer (100 mM Tris-HCL at pH 7.5, 1 M sodium chloride, 2.0 mM disodium ethylene diamine tetraacetic acid (EDTA) at pH 8.0, and 0.2% sodium dodecyl sulfate (SDS)) was added to the resuspended RNA and the mixture was allowed to cool to room temperature. The mixture was then applied to an oligo-dT (Collaborative Research Type 2 or Type 3 Bedford, Mass.) column that was previously prepared by washing the oligo-dT with a solution containing 0.1 M sodium hydroxide and 5 mM EDTA and then equilibrating the column with DEPC-treated dH$_2$O. The eluate was collected in a sterile polypropylene tube and reapplied to the same column after heating the eluate for 5 minutes at 65° C. The oligo dT column was then washed with 2 ml of high salt loading buffer consisting of 50 mM Tris-HCL at pH 7.5, 500 mM sodium chloride, 1 mM EDTA at pH 8.0 and 0.1% SDS. The oligo dT column was then washed with 2 ml of 1×medium salt buffer (50 mM Tris-HCL at pH 7.5, 100 mM sodium chloride, 1 mM EDTA at pH 8.0 and 0.1% SDS). The mRNA was eluted with 1 ml of buffer consisting of 10 mM Tris-HCL at pH 7.5, 1 mM EDTA at pH 8.0 and 0.05% SDS. The messenger RNA was purified by extracting this solution with phenol/chloroform followed by a single extraction with 100% chloroform, ethanol precipitated and resuspended in DEPC treated dh$_2$O.

In preparation for PCR amplification, mRNA was used as a template for cDNA synthesis. In a typical 250 $\mu$l reverse transcription reaction mixture, 5–10 $\mu$g of spleen mRNA in water was first annealed with 500 ng (0.5 pmol) of either the 3' V$_N$ primer (primer 12, Table I) or the 3' V$_L$ primer (primer 9, Table II) at 65° C. for 5 minutes. Subsequently, the mixture was adjusted to contain 0.8 mM dATP, 0.8 mM dCTP, 0.8 mM dGTP, 0.8 mM dTTP, 100 mM Tris-HCL (pH 8.6), 10 mM MgCl$_2$, 40 mM KCl, and 20 mM 2-ME. Moloney-Murin Leukemia Virus (Bethesda Research Laboratories (BRL), Gaithersburg, Md.) Reverse transcriptase, 26 units, was added and the solution was incubated for 1 hour at 40° C. The resultant first strand cDNA was phenol extracted, ethanol precipitated and then used in the polymerase chain reaction (PCR) procedures described below for amplification of heavy and light chain sequences.

Primers used for amplification of heavy chain Fd fragments for construction of the M13IX30 library is shown in Table I. Amplification was performed in eight separate reactions, as described by Saiki et al., *Science*, 239:487–491 (1988), which is incorporated herein by reference, each reaction containing one of the 5' primers (primers 2 to 9; SEQ ID NOS: 7 through 14, respectively) and one of the 3' primers (primer 12; SEQ ID NO: 17) listed in Table I. The remaining 5' primers, used for amplification in a single reaction, are either a degenerate primer (primer 1; SEQ ID NO: 6) or a primer that incorporates inosine at four degenerate positions (primer 10; SEQ ID NO: 15). The remaining 3' primer (primer 11; SEQ ID NO: 16) was used to construct Fv fragments. The underlined portion of the 5' primers incorporates an Xho I site and that of the 3' primer an Spe I restriction site for cloning the amplified fragments into the M13IX30 vector in a predetermined reading frame for expression.

TABLE I

HEAVY CHAIN PRIMERS

```
            CC G  G         T
1)  5'-AGGT   A CT CTCGAGTC GG-3'
            GA A  T         A 2)  5'-AGGTCCAGCTGCTCGAGTCTGG-3'
3)  5'-AGGTCCAGCTGCTCGAGTCAGG-3'
4)  5'-AGGTCCAGCTTCTCGAGTCTGG-3'
5)  5'-AGGTCCAGCTTCTCGAGTCAGG-3'
6)  5'-AGGTCCAACTGCTCGAGTCTGG-3'
7)  5'-AGGTCCAACTGCTCGAGTCAGG-3'
8)  5'-AGGTCCAACTTCTCGAGTCTGG-3'
9)  5'-AGGTCCAACTTCTCGAGTCAGG-3'

T
10) 5'-AGGTIIAICTICTCGAGTC GG-3'
                         A 11) 5'-CTATTAACTACTAACGGTAACAGTGGTGCCTTGCCCCA-3'
12) 5'-AGGCTTACTAGTACAATCCCTGGGCACAAT-3'
```

Primers used for amplification of mouse kappa light chain sequences for construction of the M13IX11 library are shown in Table II. These primers were chosen to contain restriction sites which were compatible with vector and not present in the conserved sequences of the mouse light chain mRNA. Amplification was performed as described above in five separate reactions, each containing one of the 5' primers (primers 3 to 7; SEQ ID NOS: 20 through 24, respectively) and one of the 3' primers (primer 9; SEQ ID NO: 26) listed in, Table II. The remaining 3' primer (primer 8; SEQ ID NO: 25) was used to construct Fv fragments. The underlined portion of the 5' primers depicts a Sac I restriction site and that of the 3' primers an Xba I restriction site for cloning of the amplified fragments into the M13IX11 vector in a predetermined reading frame for expression.

TABLE II

LIGHT CHAIN PRIMERS

```
1)  5'-CCAGTTCCGAGCTCGTTGTGACTCAGGAATCT-3'
2)  5'-CCAGTTCCGAGCTCGTGTTGACGCAGCCGCCC-3'
3)  5'-CCAGTTCCGAGCTCGTGCTCACCCAGTCTCCA-3'
4)  5'-CCAGTTCCGAGCTCCAGATGACCCAGTCTCCA-3'
5)  5'-CCAGATGTGAGCTCGTGATGACCCAGACTCCA-3'
6)  5'-CCAGATGTGAGCTCGTCATGACCCAGTCTCCA-3'
7)  5'-CCAGTTCCGAGCTCGTGATGACACAGTCTCCA-3'
8)  5'-GCAGCATTCTAGAGTTTCAGCTCCAGCTTGCC-3'
9)  5'-GCGCCGTCTAGAATTAACACTCATTCCTGTTGAA-3'
```

PCR amplification for heavy and light chain fragments was performed in a 100 μl reaction mixture containing the above described products of the reverse transcription reaction (≈5 μg of the cDNA-RNA hybrid), 300 nmol of 3' V$_N$ primer (primer 12, Table I; SEQ ID NO: 17), and one of the 5' V$_N$ primers (primers 2–9, Table I; SEQ ID NOS: 7 through 14, respectively) for heavy chain amplification, or, 300 nmol of 3' V$_L$ primer (primer 9, Table II; SEQ ID NO: 26), and one of the 5' V$_L$ primers (primers 3–7, Table II: SEQ ID NOS: 20 through 24, respectively) for each light chain amplification, a mixture of dNTPs at 200 mM, 50 mM KCl, 10 mM Tris-HCl (pH 8.3), 15 mM MgCl$_2$, 0.1% gelatin, and 2 units of Thermus aquaticus DNA polymerase. The reaction mixture was overlaid with mineral oil and subjected to 40 cycles of amplification. Each amplification cycle involved denaturation at 92° C. for 1 minute, annealing at 52° C. for 2 minutes, and elongation at 72° C. for 1.5 minutes. The amplified samples were extracted twice with phenol/CHCl$_3$ and once with CHCl$_3$, ethanol-precipitated, and stored at −70° C. in 10 mM Tris-HCl, pH 7.5 1 mM EDTA. The resultant products were used in constructing the M13IX30 and M13IX11 libraries (see below).

Vector Construction

Two M13-based vectors, M13IX30 (SEQ ID NO: 1) and M13IX11 (SEQ ID NO: 2), were constructed for the cloning and propagation of Hc and Lc populations of antibody fragments, respectively. The vectors were constructed to facilitate the random joining and subsequent surface expression of antibody fragment populations.

M13IX30 (SEQ ID NO: 1), or the Hc vector, was constructed to harbor diverse populations of Hc antibody fragments. M13mp19 (Pharmacia, Piscataway, N.J.) was the starting vector. This vector was modified to contain, in addition to the encoded wild type M13 gen VIII: (1) a pseudo-wild type gene VIII sequence with an amber stop codon between it and the restriction sites for cloning oligonucleotides; (2) Stu I restriction site for insertion of sequences by hybridization and, Spe I and Xho I restriction sites in-frame with the pseudo-wild type gene VIII for cloning Hc sequences; (3) sequences necessary for expression, such as a promoter, signal sequence and translation initiation signals; (4) two pairs of Hind III-Mlu I sites for random joining of Hc and Lc vector portions, and (5) various other mutations to remove redundant restriction sites and the amino terminal portion of Lac Z.

Construction of M13IX30 was performed in four steps. In the first step, an M13-based vector containing the pseudo gVIII and various other mutations was constructed, M13IX01F. The second step involved the construction of a small cloning site in a separate M13mp18 vector to yield M13IX03. This vector was then expanded to contain expression sequences and restriction sites for Hc sequences to form M13IX04B. The fourth and final step involved the incorporation of the newly constructed sequences in M13IX04B into M13IX01F to yield M13IX30.

Construction of M13IX01F first involved the generation of a pseudo wild-type gVIII sequence for surface expression of antibody fragments. The pseudo-wild type gene encodes the identical amino acid sequence as that of the wild type gene; however, the nucleotide sequence has been altered so that only 63% identity exists between this gene and the encoded wild type gene VIII. Modification of the gene VIII nucleotide sequence used for surface expression reduces the possibility of homologous recombination with the wild type gene VIII contained on the same vector. Additionally, the wild type M13 gene VIII was retained in the vector system to ensure that at least some functional, non-fusion coat protein would be produced. The inclusion of wild type gene VIII facilitates the growth of phage under conditions where there is surface expression of the polypeptides and therefore reduces the possibility of non-viable phage production from the fusion genes.

The pseudo-wild type gene VIII was constructed by chemically synthesizing a series of oligonucleotides which encode both strands of the gene. The oligonucleotides are presented in Table III.

TABLE III

Pseudo-Wild Type Gene VIII Oligonucleotide Series

Sequence (5' to 3')

Top Strand Oligonucleotides

| | |
|---|---|
| VIII 03 | GATCC TAG GCT GAA GGC GAT GAC CCT GCT AAG GCT GC |
| VIII 04 | A TTC AAT AGT TTA CAG GCA AGT GCT ACT GAG TAC A |
| VIII 05 | TT GGC TAC GCT TGG GCT ATG GTA GTA GTT ATA GTT |
| VIII 06 | GGT GCT ACC ATA GGG ATT AAA TTA TTC AAA AAG TT |
| VIII 07 | T ACG AGC AAG GCT TCT TA |

Bottom Strand Oligonucleotides

| | |
|---|---|
| VIII 08 | AGC TTA AGA AGC CTT GCT CGT AAA CTT TTT GAA TAA TTT |
| VIII 09 | AAT CCC TAT GGT AGC ACC AAC TAT AAC TAC TAC CAT |
| VIII 10 | AGC CCA AGC GTA GCC AAT GTA CTC AGT AGC ACT TG |
| VIII 11 | C CTG TAA ACT ATT GAA TGC AGC CTT AGC AGG GTC |
| VIII 12 | ATC GCC TTC AGC CTA G |

Except for the terminal oligonucleotides VIII 03 (SEQ ID NO: 27) and VIII 08 (SEQ ID NO: 32), the above oligonucleotides (oligonucleotides VIII 04–07 (SEQ ID NOS: 28 through 31, respectively) and VIII 09–12 (SEQ ID NOS: 33 through 36, respectively)) were mixed at 200 ng each in 10 μl final volume, phosphorylated with T4 polynucleotide Kinase (Pharmacia) and 1 mM ATP at 37° C. for 1 hour, heated to 70° C. for 5 minutes, and annealed into double-stranded form by heating to 65° C. for 3 minutes, followed by cooling to room temperature over a period of 30 minutes. The reactions were treated with 1.0 U of T4 DNA ligase (BRL) and 1 mM ATP at room temperature for 1 hour, followed by heating to 70° C. for 5 minutes. Terminal oligonucleotides were then annealed to the ligated oligonucleotides. The annealed and ligated oligonucleotides yielded a double-stranded DNA flanked by a Bam HI site at its 5' end and by a Hind III site at its 3' end. A translational stop codon (amber) immediately follows the Bam HI site. The gene VIII sequence begins with the codon GAA (Glu) two codons 3' to the stop codon. The double-stranded insert was cloned in frame with the Eco RI and Sac I sites within the M13 polylinker. To do so, M13mp19 was digested with Bam HI (New England Biolabs, Beverley, Mass.) and Hind III (New England Biolabs) and combined at a molar ratio of 1:10 with the double-stranded insert. The ligations were performed at room temperature overnight in 1×ligase buffer (50 mM Tris-HCl, pH 7.8, 10 mM $MgCl_2$, 20 mM DTT, 1 mM ATP, 50 μg/ml BSA) containing 1.0 U of T4 DNA ligase (New England Biolabs). The ligation mixture was transformed into a host and screened for positive clones using standard procedures in the art.

Several mutations were generated within the construct to yield functional M13IX01F. The mutations were generated using the method of Kunkel et al., Meth. Enzymol. 154:367–382 (1987), which is incorporated herein by reference, for site-directed mutagenesis. The reagents, strains and protocols were obtained from a Bio Rad Mutagenesis kit (Bio Rad, Richmond, Calif.) and mutagenesis was performed as recommended by the manufacturer.

Two Fok I sites were removed from the vector as well as the Hind III site at the end of the pseudo gene VIII sequence using the mutant oligonucleotides 5'-CATTTTTGCAGATGGCTTAGA-3' (SEQ ID NO: 37) and 5'-TAGCATTAACGTCCAATA-3' (SEQ ID NO: 38). New Hind III and Mlu I sites were also introduced at position 3919 and 3951 of M13IX01F. The oligonucleotides used for this mutagenesis had the sequences 5'-ATATATTTTAGTAAGCTTCATCTTCT-3' (SEQ ID NO: 39), and 5'-GACAAAGAACGCGTGAAAACTTT-3' (SEQ ID NO: 40), respectively. The amino terminal portion of Lac Z was deleted by oligonucleotide-directed mutagenesis using the mutant oligonucleotide 5'-GCGGGCCTCTTCGCTATTGCTTAAGAAGCCTTGC-T-3' (SEQ ID NO: 41). In constructing the above mutations, all changes made in a M13 coding region were performed such that the amino acid sequence remained unaltered. The resultant vector, M13IX01F, was used in the final step to construct M13IX30 (see below).

In the second step, M13mp18 was mutated to remove the 5' end of Lac Z up to the Lac i binding site and including the Lac Z ribosome binding site and start codon. Additionally, the polylinker was removed and a Mlu I site was introduced in the coding region of Lac Z. A single oligonucleotide was used for these mutagenesis and had the sequence 5'-AAACGACGGCCAGTGCCAAGTGACGCGTGTGA-AATTGTTATCC-3' (SEQ ID NO: 42). Restriction enzyme sites for Hind III and Eco RI were introduced downstream of the Mlu I site using the oligonucleotide 5'-GGCGAAAGGGAATTCTGCAAGGCGATTAAGCTT-GGGTAACGCC-3' (SEQ ID NO. 43). These modifications of M13mp18 yielded the precursor vector M13IX03.

The expression sequences and cloning sites were introduced into M13IX03 by chemically synthesizing a series of oligonucleotides which encode both strands of the desired sequence. The oligonucleotides are presented in Table IV and correspond to oligonucleotides 084, 027, 028, 029, 085, 031, 032 and 033 as SEQ ID NOS:44–51, respectively.

TABLE IV

M13IX30 Oligonucleotide Series

Sequence (5' to 3')

Top Strand Oligonucleotides

| | |
|---|---|
| 084 | GGCGTTACCCAAGCTTTGTACATGGAGAAAATAAAG |
| 027 | TGAAACAAAGCACTATTGCACTGGCACTCTTACCGTTACCGT |
| 028 | TACTGTTTACCCCTGTGACAAAAGCCCCCCAGGTCCAGCTGC |
| 029 | TCGAGTCAGGCCTATTGTGCCCAGGGATTGTACTAGTGGATCCG |

Bottom Oligonucleotides

| | |
|---|---|
| 085 | TGGCGAAAGGGAATTCGGATCCACTAGTACAATCCCTG |
| 031 | GGCACAATAGGCCTGACTCGAGCAGCTGGACCAGGGCGGCTT |
| 032 | TTGTCACAGGGGTAAACAGTAACGGTAACGGTAAGTGTGCCA |
| 033 | GTGCAATAGTGCTTTGTTTCACTTTATTTTCTCCATGTACAA |

The above oligonucleotides of Table IV, except for the terminal oligonucleotides 084 (SEQ ID NO: 44) and 085 (SEQ ID NO: 48), were mixed, phosphorylated, annealed and ligated to form a double-stranded insert as described in Example I. However, instead of cloning directly into the intermediate vector the insert was first amplified by PCR. The terminal oligonucleotides were used as primers for PCR. Oligonucleotide 084 (SEQ ID NO: 44) contains a Hind III site, 10 nucleotides internal to its 5' end and oligonucleotide 085 (SEQ ID NO: 48) has an Eco RI site at its 5' end. Following amplification, the products were restricted with Hind III and Eco RI and ligated, as described in Example I, into the polylinker of M13mp18 digested with the same two enzymes. The resultant double stranded insert contained a ribosome binding site, a translation initiation codon followed by a leader sequence and three restriction enzyme sites for cloning random oligonucleotides (Xho I, Stu I, Spe I). The intermediate vector was named M13IX04.

During cloning of the double-stranded insert, it was found that one of the GCC codons in oligonucleotides 028 and its complement in 031 was deleted. Since this deletion did not affect function, the final construct is missing one of the two GCC codons. Additionally, oligonucleotide 032 (SEQ ID NO: 50) contained a GTG codon where a GAG codon was needed. Mutagenesis was performed using the oligonucleotide 5'-TAACGGTAAGAGTGCCAGTGC-3' (SEQ ID NO: 52) to convert the codon to the desired sequence. The resultant vector is named M13IX04B.

Figure 2A:
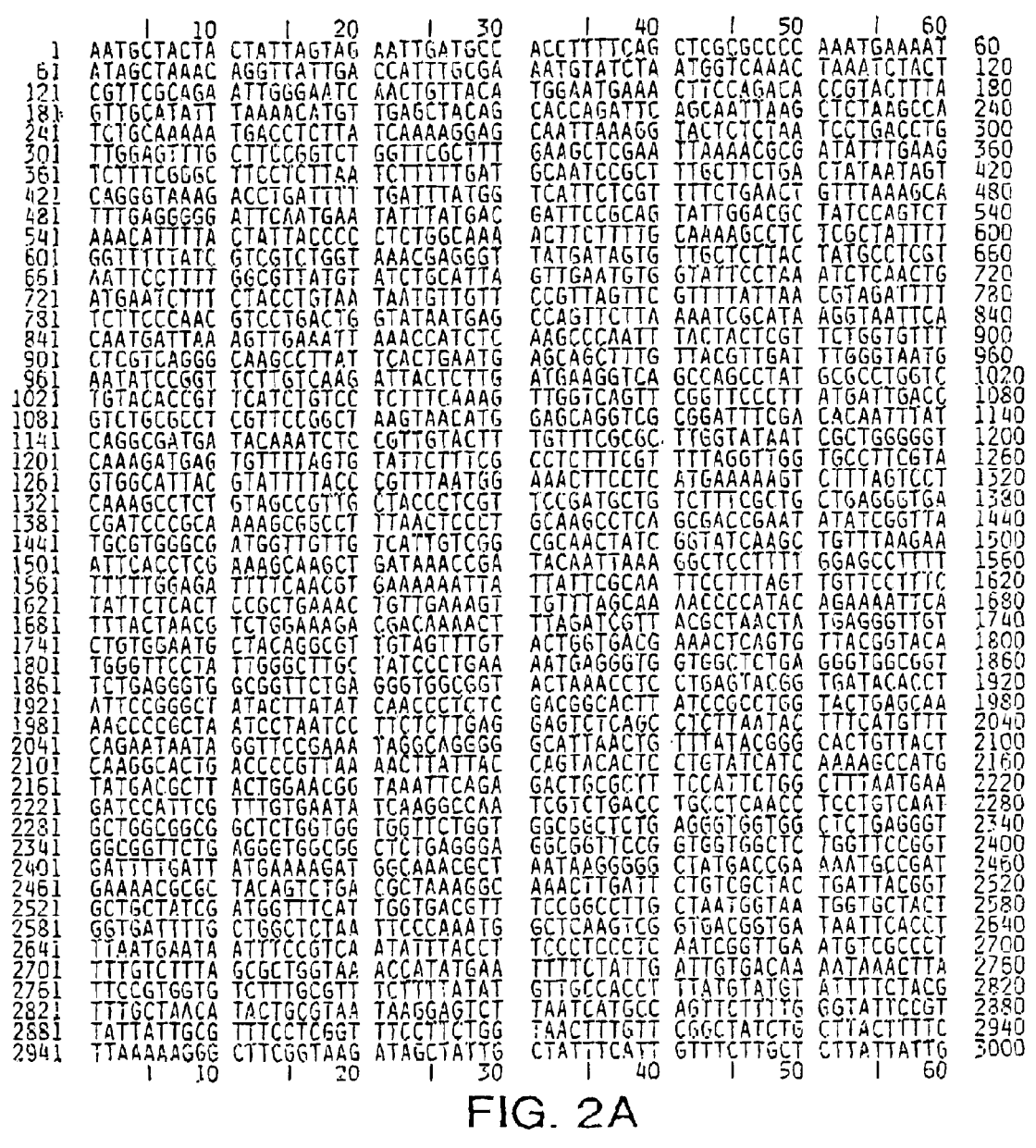

The third step in constructing M13IX30 involved inserting the expression and cloning sequences from M13IX04B upstream of the pseudo wild-type gVIII in M13IX01F. This was accomplished by digesting M13IX04B with Dra III and Bam HI and gel isolating the 700 base pair insert containing the sequences of interest. M13IX01F was likewise digested with Dra III and Bam HI. The insert was combined with the double digested vector at a molar ratio of 1:1 and ligated as described in Example I. The sequence of the final construct M13IX30, is shown in FIGS. 2A, 2B and 2C (SEQ ID NO: 1). FIG. 1A also shows M13IX30 where each of the elements necessary for surface expression of Hc fragments is marked. It should be noted during modification of the vectors, certain sequences differed from the published sequence of M13mp18. The new sequences are incorporated into the sequences recorded herein.

M13IX11 (SEQ ID NO: 2), or the Lc vector, was constructed to harbor diverse populations of Lc antibody fragments. This vector was also constructed from M13mp19 and contains: (1) sequences necessary for expression, such as a promoter, signal sequence and translation initiation signals; (2) Eco RV restriction site for insertion of sequences by hybridization and Sac I and Xba I restriction sites for cloning of Lc sequences; (3) two pairs of Hind III-Mlu I sites for random joining of Hc and Lc vector portions, and (4) various other mutation to remove redundant restriction sites.

The expression, translation initiation signals, cloning sites, and one of the Mlu I sites were constructed by annealing of overlapping oligonucleotides as described above to produce a double-stranded insert containing a 5' Eco RI site and a 3' Hind III site. The overlapping oligonucleotides are shown in Table V and correspond to oligonucleotides 082, 015, 016, 017, 018, 019, 083, 021, 022 and 023 as SEQ ID NOS:53–62, respectively and were ligated as a double-stranded insert between the Eco RI and Hind III sites of M13mp18 as described for the expression sequences inserted into M13IX03. The ribosome binding site (AGGAGAC) is located in oligonucleotide 015 and the translation initiation codon (ATG) is the second to fourth nucleotides of oligonucleotide 016 (SEQ ID NO: 55).

TABLE V

Oligonucleotide Series for Construction of Translation Signals in M13IX11

| Oligonucleotide | Sequence (5' to 3') |
|---|---|
| 082 | CACC TTCATG AATTC GGC AAG GAGACA GTCAT |
| 015 | AATT C GCC AAG GAG ACA GTC AT |
| 016 | AATG AAA TAC CTA TTG CCT ACC GCA GCC GCT CGA TTG TT |
| 017 | ATTA CTC GCT GCC CAA CCA GCC ATG GCC GAG CTC GTG AT |
| 018 | GACC CAG ACT CCA GATATC CAA CAG GAA TGA GTG TTA AT |
| 019 | TCT AGA ACG CGT C |
| 083 | TTCAGGTTGAAGC TTA CGC GTT CTA GAA TTA ACA CTC ATT CCTGT |
| 021 | TG GAT ATC TGG AGT CTG GGT CAT CAC GAG CTC GGC CAT G |
| 022 | GC TGG TTG GGC AGC GAG TAA TAA CAA TCC AGC GGC TGC C |
| 023 | GT AGG CAA TAG GTA TTT CAT TAT GAC TGT CCT TGG CG |

Oligonucleotide 017 (SEQ ID NO: 56) contained a Sac I restriction site 67 nucleotides downstream from the ATG codon. The naturally occurring Eco RI site was removed and new Eco RI and Hind III sites were introduced downstream from the Sac I. Oligonucleotides 5'-TGACTGTCTCCTTGGCGTGTGAAATTGTTA-3' (SEQ ID NO: 63) and 5'-TAACACTCATTCCGGATGGAATTCTGGAGTCTGGGT-3' (SEQ ID NO: 64) were used to generate each of the mutations, respectively. The Lac Z ribosome binding site was removed when the original Eco RI site in M13mp19 was mutated. Additionally, when the new Eco RI and Hind III sites were generated, a spontaneous 100 bp deletion was found just 3' to these sites. Since the deletion does not affect the function, it was retained in the final vector.

In addition to the above mutations, a variety of other modifications were made to incorporate or remove certain sequences. The Hind III site used to ligate the double-stranded insert was removed with the oligonucleotide 5'-GCCAGTGCCAAGTGACGCGTTCTA-3' (SEQ ID NO: 65). Second Hind III and Mlu I sites were introduced at positions 3922 and 3952, respectively, using the oligonucleotides 5'-ATATATTTTAGTAAGCTTCATCTTCT-3' (SEQ ID NO: 66) for the Hind III mutagenesis and 5'-GACAAAGAACGCGTGAAAACTTT-3' (SEQ ID NO: 67) for the Mlu I mutagenesis. Again, mutations within the coding region did not alter the amino acid sequence.

The sequence of the resultant vector, M13IX11, is shown in FIGS. 3A, 3B and 3C (SEQ ID NO: 2). FIG. 1B also shows M13IX11 where each of the elements necessary for producing a surface expression library between Lc fragments is marked.

Library Construction

Each population of Hc and Lc sequences synthesized by PCR above are separately cloned into M13IX30 and M13IX11, respectively, to create Hc and Lc libraries.

The Hc and Lc products (5 µg) are mixed, ethanol precipitated and resuspended in 20 µl of NaOAc buffer (33 mM Tris acetate, pH 7.9, 10 mM Mg-acetate, 66 mM K-acetate, 0.5 mM DTT). Five units of T4 DNA polymerase is added and the reactions incubated at 30° C. for 5 minutes to remove 3' termini by exonuclease digestion. Reactions are stopped by heating at 70° C. for 5 minutes. M13IX30 is digested with Stu I and M13IX11 is digested with Eco RV. Both vectors are treated with T4 DNA polymerase as described above and combined with the appropriate PCR products at a 1:1 molar ratio at 10 ng/µl to anneal in the above buffer at room temperature overnight. DNA from each annealing is electroporated into MK30-3 (Boehringer, Indianapolis, Ind.), as described below, to generate the Hc and Lc libraries.

E. coli MK30-3 is electroporated as described by Smith et al., Focus 12:38–40 (1990) which is incorporated herein by reference. The cells are prepared by inoculating a fresh colony of MK30-3 into 5 mls of SOB without magnesium (20 g bacto-tryptone, 5 g bacto-yeast extract, 0.584 g NaCl, 0.186 g KCl, $dH_2O$ to 1,000 mls) and grown with vigorous aeration overnight at 37° C. SOB without magnesium (500 ml) is inoculated at 1:1000 with the overnight culture and grown with vigorous aeration at 37° C. until the $OD_{550}$ is 0.8 (about 2 to 3 h). The cells are harvested by centrifugation at 5,000 rpm (2,600×g) in a GS3 rotor (Sorvall, Newtown, Conn.) at 4° C. for 10 minutes, resuspended in 500 ml of ice-cold 10% (v/v) sterile glycerol, centrifuged and resuspended a second time in the same manner. After a third centrifugation, the cells are resuspended in 10% sterile glycerol at a final volume of about 2 ml, such that the $OD_{550}$ of the suspension was 200 to 300. Usually, resuspension is achieved in the 10% glycerol that remained in the bottle after pouring off the supernate. Cells are frozen in 40 µl aliquots in microcentrifuge tubes using a dry ice-ethanol bath and stored frozen at −70° C.

Frozen cells are electroporated by thawing slowly on ice before use and mixing with about 10 pg to 500 ng of vector per 40 µl of cell suspension. A 40 µl aliquot is placed in an 0.1 cm electroporation chamber (Bio-Rad, Richmond, Calif.) and pulsed once at 0° C. using 4 kΩ parallel resistor 25 µF, 1.88 KV, which gives a puls length (τ) of −4 ms. A 10 µl aliquot of the pulsed cells are diluted into 1 ml SOC (98 mls SOB plus 1 ml of 2 M $MgCl_2$ and 1 ml of 2 M glucose) in a 12-×75-mm culture tube, and the culture is shaken at 37° C. for 1 hour prior to culturing in selective media, (see below).

Each of the libraries are cultured using methods known to one skilled in the art. Such methods can be found in Sanbrook et al., Molecular Cloning: A Laboratory Manuel, Cold Spring Harbor Laboratory, Cold Spring Harbor, 1989, and in Ausubel et al., Current Protocols in Molecular Biology, John Wiley and Sons, New York, 1989, both of which are incorporated herein by reference. Briefly, the above 1 ml library cultures are grown up by diluting 50-fold into 2XYT media (16 g tryptone, 10 g yeast extract, 5 g NaCl) and culturing at 37° C. for 5–8 hours. The bacteria are pelleted by centrifugation at 10,000×g. The supernatant containing phage is transferred to a sterile tube and stored at 4° C.

Double strand vector DNA containing Hc and Lc antibody fragments are isolated from the cell pellet of each library. Briefly, the pellet is washed in TE (10 mM Tris, pH 8.0, 1 mM EDTA) and recollected by centrifugation at 7,000 rpm for 5' in a Sorval centrifuge (Newtown, Conn.). Pellets are resuspended in 6 mls of 10% Sucrose, 50 mM Tris, pH 8.0. 3.0 ml of 10 mg/µl lysozyme is added and incubated on ice for 20 minutes. 12 mls of 0.2 M NaOH, 1% SDS is added followed by 10 minutes on ice. The suspensions are then incubated on ice for 20 minutes after addition of 7.5 mls of 3 M NaOAc, pH 4.6. The samples are centrifuged at 15,000 rpm for 15 minutes at 4° C., RNased and extracted with phenol/chloroform, followed by ethanol precipitation. The pellets are resuspended, weighed and an equal weight of $CsCl_2$ is dissolved into each tube until a density of 1.60 g/ml is achieved. EtBr is added to 600 µg/ml and the double-stranded DNA is isolated by equilibrium centrifugation in a TV-1665 rotor (Sorval) at 50,000 rpm for 6 hours. These DNAs from each right and left half sublibrary are used to generate forty libraries in which the right and left halves of the randomized oligonucleotides have been randomly joined together.

The surface expression library is formed by the random joining of the Hc containing portion of M13IX30 with the Lc containing portion of M13IX11. The DNAs isolated from each library was digested separately with an excess amount of restriction enzyme. The Lc population (5 µg) is digested with Hind III. The Hc (5 µg) population is digested with Mlu I. The reactions are stopped by phenol/chloroform extraction followed by ethanol precipitation. The pellets are washed in 70% ethanol and resuspended in 20 µl of NaOAc buffer. Five units of T4 DNA polymerase (Pharmacia) is added and the reactions incubated at 30° C. for 5 minutes. Reactions are stopped by heating at 70° C. for 5 minutes. The Hc and Lc DNAs are mixed to a final concentration of 10 ng each vector/µl and allowed to anneal at room temperature overnight. The mixture is electroporated into MK30-3 cells as described above.

Screening of Surface Expression Libraries

Purified phage are prepared from 50 ml liquid cultures of XL1 Blue™ cells (Stratagene, La Jolla, Calif.) which had been infected at a m.o.i. of 10 from the phage stocks stored at 4° C. The cultures are induced with 2 mM IPTG. Supernatants are cleared by two centrifugations, and the phage are precipitated by adding 1/7.5 volumes of PEG solution (25% PEG-8000, 2.5 M NaCl), followed by incubation at 4° C. overnight. The precipitate is recovered by centrifugation for 90 minutes at 10,000×g. Phage pellets are resuspended in 25 ml of 0.01 M Tris-HCl, pH 7.6, 1.0 mM EDTA, and 0.1% Sarkosyl and then shaken slowly at room temperature for 30 minutes. The solutions are adjusted to 0.5 M NaCl and to a final concentration of 5% polyethylene glycol. After 2 hours at 4° C., the precipitates containing the phage are recovered by centrifugation for 1 hour at 15,000× g. The precipitates are resuspended in 10 ml of NET buffer (0.1 M NaCl, 1.0 mM EDTA, and 0.01 M Tris-HCl, pH 7.6), mixed well, and the phage repelleted by centrifugation at 170,000×g for 3 hours. The phage pellets are resuspended overnight in 2 ml of NET buffer and subjected to cesium chloride centrifugation for 18 hours at 110,000×g (3.86 g of cesium chloride in 10 ml of buffer). Phage bands are collected, diluted 7-hold with NET buffer, recentrifuged at 170,000×g for 3 hours, resuspended, and stored at 4° C. in 0.3 ml of NET buffer containing 0.1 mM sodium azide.

The BDP used for panning on streptavidin coated dishes is first biotinylated and then absorbed against UV-inactivated blocking phage (see below). The biotinylating reagents are dissolved in dimethylformamide at a ratio of 2.4 mg solid NHS-SS-Biotin (sulfosuccinimidyl 2-(biotinamido)ethyl-1,3' -dithiopropionate; Pierce, Rockford, Ill.) to 1 ml solvent and used as recommended by the manufacturer. Small-scale reactions are accomplished by mixing 1 µl dissolved reagent with 43 µl of 1 mg/ml BDP diluted in sterile bicarbonate buffer (0.1 M NaHCO$_3$, pH 8.6). After 2 hours at 25° C., residual biotinylating reagent is reacted with 500 µl 1 M ethanolamine (pH adjusted to 9 with HCl) for an additional 2 hours. The entire sample is diluted with 1 ml TBS containing 1 mg/ml BSA, concentrated to about 50 µl on a Centricon 30 ultra-filter (Amicon), and washed on the same filter three times with 2 ml TBS and once with 1 ml TBS containing 0.02% NaN$_3$ and 7×10$^{12}$ UV-inactivated blocking phage (see below); the final retentate (60–80 µl ) is stored at 4° C. BDP biotinylated with the NHS-SS-Biotin reagent is linked to biotin via a disulfide-containing chain.

UV-irradiated M13 phage are used for blocking any biotinylated BDP which fortuitously binds filamentous phage in general. M13mp8 (Messing and Vieira, Gene 19: 262–276 (1982), which is incorporated herein by reference) is chosen because it carries two amber mutations, which ensure that the few phage surviving irradiation will not grow in the sup O strains used to titer the surface expression library. A 5 ml sample containing 5×10$^{13}$ M13mp8 phage, purified as described above, is placed in a small petri plate and irradiated with a germicidal lamp at a distance of two feet for 7 minutes (flux 150 µW/cm$^2$). NaN$_3$ is added to 0.02% and phage particles concentrated to 10$^{14}$ particles/ml on a Centricon 30-kDa ultrafilter (Amicon).

For panning, polystyrene petri plates (60×15 mm) are incubated with 1 ml of 1 mg/ml of streptavidin (BRL) in 0.1 M NaHCO$_3$ pH 8.6–0.02% NaN$_3$ in a small, air-tight plastic box overnight in a cold room. The next day streptavidin is removed and replaced with at least 10 ml blocking solution (29 mg/ml of BSA; 3 µg/ml of streptavidin; 0.1 M NaHCO$_3$ pH 8.6–0.02% NaN$_3$) and incubated at least 1 hour at room temperature. The blocking solution is removed and plates are washed rapidly three times with Tris buffered saline containing 0.5% Tween 20 (TBS-0.5% Tween 20).

Selection of phage expressing antibody fragments which bind BDP is performed with 5 µl (2.7 µg BDP) of blocked biotinylated BDP reacted with a 50 µl portion of the library. Each mixture is incubated overnight at 4° C., diluted with 1 ml TBS-0.5% Tween 20, and transferred to a streptavidin-coated petri plate prepared as described above. After rocking 10 minutes at room temperature, unbound phage are removed and plates washed ten times with TBS-0.5% Tween 20 over a period of 30–90 minutes. Bound phage are eluted from plates with 800 µl sterile elution buffer (1 mg/ml BSA, 0.1 M HCl, pH adjusted to 2.2 with glycerol) for 15 minutes and eluates neutralized with 48 µl 2 M Tris (pH unadjusted). A 20 µl portion of each eluate is titered on MK30-3 concentrated cells with dilutions of input phage.

A second round of panning is performed by treating 750 µl of first eluate from the library with 5 mM DTT for 10 minutes to break disulfide bonds linking biotin groups to residual biotinylated binding proteins. The treated eluate is concentrated on a Centricon 30 ultrafilter (Amicon), washed three times with TBS-0.5% Tween 20, and concentrated to a final volume of about 50 µl. Final retentate is transferred to a tube containing 5.0 µl (2.7 µg BDP) blocked biotinylated BDP and incubated overnight. The solution is diluted with 1 ml TBS-0.5% Tween 20, panned, and eluted as described above on fresh streptavidin-coated petri plates. The entire second eluate (800 µl) is neutralized with 48 µl 2 M Tris, and 20 µl is titered simultaneously with the first eluate and dilutions of the input phage. If necessary, further rounds of panning can be performed to obtain homogeneous populations of phage. Additionally, phage can be plaque purified if reagents are available for detection.

Template Preparation and Sequencing

Templates are prepared for sequencing by inoculating a 1 ml culture of 2XYT containing a 1:100 dilution of an overnight culture of XL1 with an individual plaque from the purified population. The plaques are picked using a sterile toothpick. The culture is incubated at 37° C. for 5–6 hours with shaking and then transferred to a 1.5 ml microfuge tube. 200 µl of PEG solution is added, followed by vortexing and placed on ice for 10 minutes. The phage precipitate is recovered by centrifugation in a microfuge at 12,000×g for 5 minutes. The supernatant is discarded and the pellet is resuspended in 230 µl of TE (10 mM Tris-HCl, pH 7.5, 1 mM EDTA) by gently pipeting with a yellow pipet tip. Phenol (200 µl ) is added, followed by a brief vortex and microfuged to separate the phases. The aqueous phase is transferred to a separate tube and extracted with 200 µl of phenol/chloroform (1:1) as described above for the phenol extraction. A 0.1 volume of 3 M NaOAc is added, followed by addition of 2.5 volumes of ethanol and precipated at −20° C. for 20 minutes. The precipitated templates are recovered by centrifugation in a microfuge at 12,000×g for 8 minutes. The pellet is washed in 70% ethanol, dried and resuspended in 25 µl TE. Sequencing was performed using a Sequenase™ sequencing kit following the protocol supplied by the manufacturer (U.S. Biochemical, Cleveland, Ohio).

EXAMPLE II

Cloning of Heavy and Light Chain Sequences Without Restriction Enzyme Digestion

This example shows the simultaneous incorporation of antibody heavy and light chain fragment encoding sequences into a M13IXHL-type vector without use of restriction endonucleases.

For the simultaneous incorporation of heavy and light chain encoding sequences into a single coexpression vector, a M13IXHL vector was produced that contained heavy and light chain encoding sequences for a mouse monoclonal antibody (DAN-18H4; Biosite, San Diego, Calif.). The inserted antibody fragment sequences are used as complementary sequences for the hybridization and incorporation of Hc and Lc sequences by site-directed mutagenesis. The genes encoding the heavy and light chain polypeptides were inserted into M13IX30 (SEQ ID NO: 1) and M13IX11 (SEQ ID NO: 2), respectively, and combined into a single surface expression vector as described in Example I. The resultant M13IXHL-type vector is termed M13IX50.

The combinations were performed under conditions that facilitate the formation of one Hc and one Lc vector half into a single circularized vector. Briefly, the overhangs generated between the pairs of restriction sites after restriction with Mlu I or Hind III and exonuclease digestion are unequal (i.e., 64 nucleotides compared to 32 nucleotides). These unequal lengths result in differential hybridization temperatures for specific annealing of the complementary ends from each vector. The specific hybridization of each end of each vector half was accomplished by first annealing at 65° C. in a small volume (about 100 μg/μl) to form a dimer of one Hc vector half and one Lc vector half. The dimers were circularized by diluting the mixture (to about 20 μg/μl ) and lowering the temperature to about 25–37° C. to allow annealing. T4 ligase was present to covalently close the circular vectors.

M13IX50 was modified such that it did not produce a functional polypeptide for the DAN monoclonal antibody. To do this, about eight amino acids were changed within the variable region of each chain by mutagenesis. The Lc variable region was mutagenized using the oligonucleotide 5'-CTGAACCTGTCTGGGACCACAGTTGATGCTATAG-GATCAGATCTAGAATTCATTTAGAGACTGGCCTGGC-TTCTGC-3' (SEQ ID NO: 68). The Hc sequence was mutagenized with the oligonucleotide 5'-TCGACCGTTGGTAGGAATAATGCAATTAATGGAG-TAGCTCTAAATTCAGAATTCATCTACACCCAGTGCA-TCCAGTAGCT-3' (SEQ ID NO: 69). An additional mutation was also introduced into M13IX50 to yield the final form of the vector. During construction of an intermediate to X13IX50 (M13IX04 described in Example I), a six nucleotide sequence was duplicated in oligonucleotide 027 and its complement 032. This sequence, 5'TTACCG-3' was deleted by mutagenesis using the oligonucleotide 5'-GGTAAACAGTAACGGTAAGAGTGCCAG-3' (SEQ ID NO: 70). The resultant vector was designated M13IX53.

M13IX53 can be produced as a single stranded form and contains all the functional elements of the previously described M13IXHL vector except that it does not express functional antibody heteromers. The single-stranded vector can be hybridized to populations of single-stranded Hc and Lc encoding sequences for their incorporation into the vector by mutagenesis. Populations of single-stranded Hc and Lc encoding sequences can be produced by one skilled in the art from the PCR products described in Example I or by other methods known to one skilled in the art using the primers and teachings described therein. The resultant vectors with Hc and Lc encoding sequences randomly incorporated are propagated and screened for desired binding specificities as described in Example I.

Other vectors similar to M13IX53 and the vectors it's derived from, M13IX11 and M13IX30, have also been produced for the incorporation of Hc and Lc encoding sequences without restriction. In contrast to M13IX53, these vectors contain human antibody sequences for the efficient hybridization and incorporation of populations of human Hc and Lc sequences. These vectors are briefly described below. The starting vectors were either the Hc vector (M13IX30) or the Lc vector (M13IX11) previously described.

M13IX32 was generated from M13IX30 by removing the six nucleotide redundant sequence 5'-TTACCG-3' described above and mutation of the leader sequence to increase secretion of the product. The oligonucleotide used to remove the redundant sequence is the same as that given above. The mutation in the leader sequence was generated using the oligonucleotide 5'GGGCTTTTCCACAGGGGT-3' (SEQ ID NO: 76 ). This mutagenesis resulted in the A residue at position 6353 of M13IX30 being changed to a G residue.

A decapeptide tag for affinity purification of antibody fragments was incorporated in the proper reading frame at the carboxy-terminal end of the Hc expression site in M13IX32. The oligonucleotide used for this mutagenesis was 5'-CGCCTTCAGCCTAAGAAGCGTAGTCCG-GAACGTCGTACGGGTAGGATCCACTAG-3' (SEQ ID NO: 71). The resultant vector was designated M13IX33. Modifications to this or other vectors are envisioned which include various features known to one skilled in the art. For example, a peptidase cleavage site can be incorporated following the decapeptide tag which allows the antibody to be cleaved from the gene VIII portion of the fusion protein.

Figure 4A:
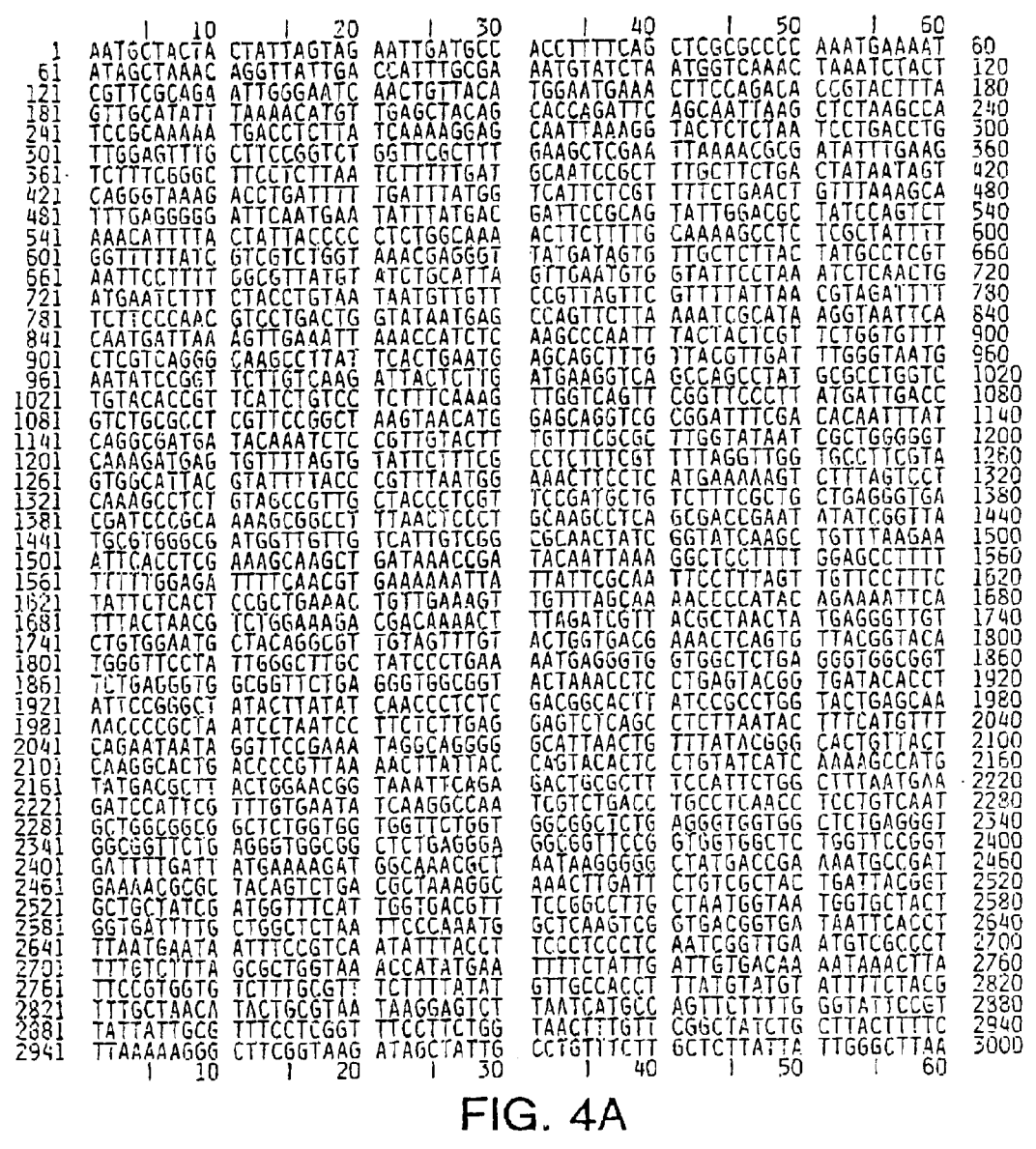
Figure 4B:
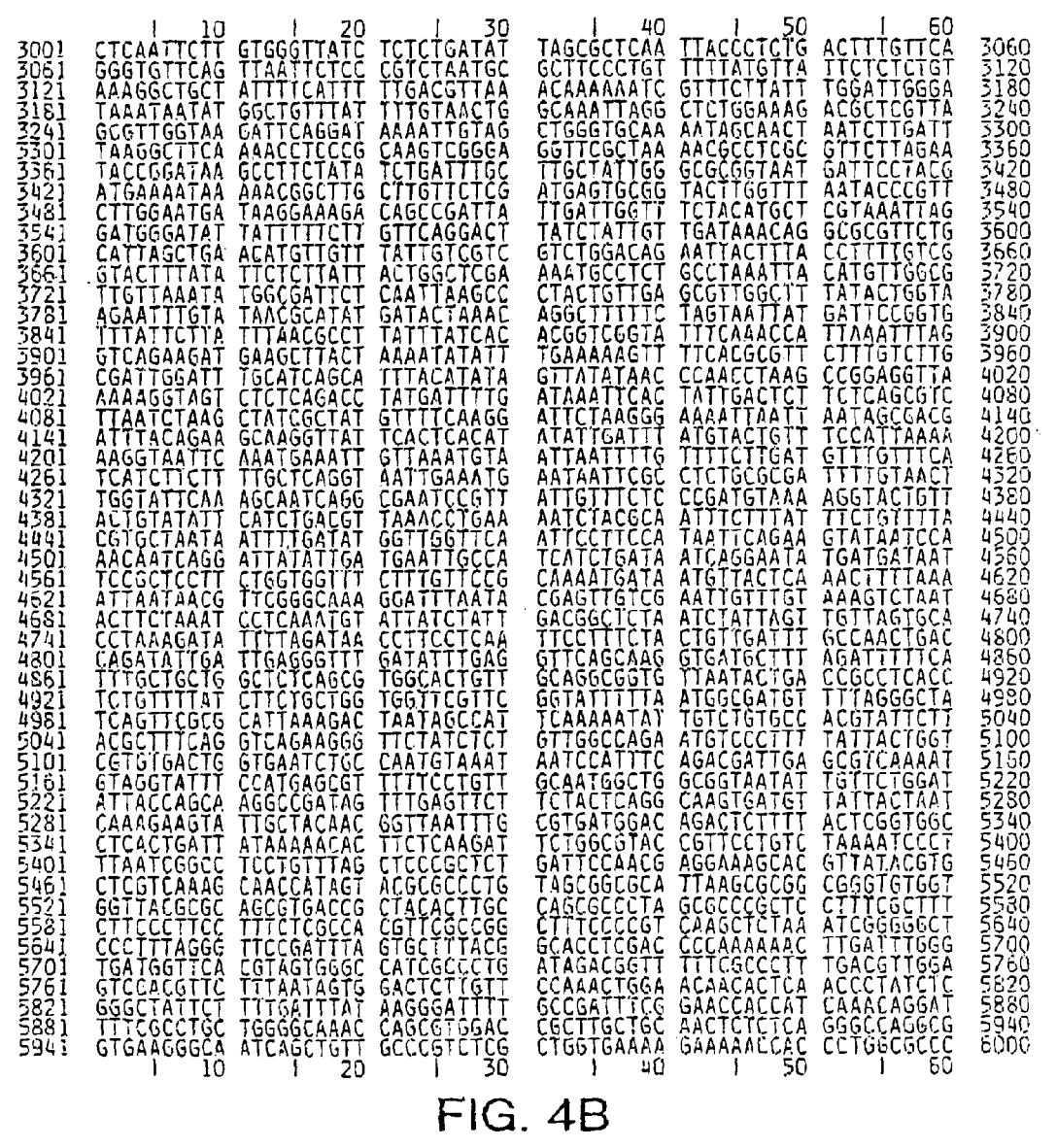

M13IX34 (SEQ ID NO: 3) was created from M13IX33 by cloning in the gene encoding a human IgG1 heavy chain. The reading frame of the variable region was changed and a stop codon was introduced to ensure that a functional polypeptide would not be produced. The oligonucleotide used for the mutagenesis of the variable region was 5'-CACCGGTTCGGGGAATTAGTCTTGACCAGGCAG-CCCAGGGC-3' (SEQ ID NO: 72). The complete nucleotide sequence of this vector is shown in FIGS. 4A, 4B and 4C (SEQ ID NO: 3).

Several vectors of the M13IX11 series were also generated to contain similar modifications as that described for the vectors M13IX53 and M13IX34. The promoter region in M13IX11 was mutated to conform to the 35 consensus sequence to generate M13IX12. The oligonucleotide used for this mutgenesis was 5'-ATTCCACACATTATACGAGCCCGGAAGCATAAAG-TGCAAGCCTGGGGTGCC-3' (SEQ ID NO: 73). A human kappa light chain sequence was cloned into M13IX12 and the variable region subsequently deleted to generate M13IX13 (SEQ ID NO: 4). The complete nucleotide sequence of this vector is shown in FIGS. 5A, 5B and 5C (SEQ ID NO: 4). A similar vector, designated M13IX14, was also generated in which the human lambda light chain was inserted into M13IX12 followed by deletion of the variable region. The oligonucleotides used for the variable region deletion of M13IX13 and M13IX14 were 5'-CTGCTCATCAGATGGCGGGAAGAGCTCGGCCAT-GGCTGGTTG-3' (SEQ ID NO: 74) and 5'-GAACAGAGTGACCGAGGGGGCGAGCTCGGCCA-TGGCTGGTTG-3' (SEQ ID NO: 75), respectively.

The Hc and Lc vectors or modified forms thereof can be combined using the methods described in Example I to produce a single vector similar to M13IX53 that allows the efficient incorporation of human Hc and Lc encoding sequences by mutagenesis. An example of such a vector is the combination of M13IX13 with M13IX34. The complete nucleotide sequence of this vector, M13IX60, is shown in FIGS. 6A, 6B and 6C (SEQ ID NO: 5).

Additional modifications to any of the previously described vectors can also be performed to generate vectors which allow the efficient incorporation and surface expression of Hc and Lc sequences. For example, to alleviate the use of uracil selection against wild-type template during mutagenesis procedures, the variable region locations within the vectors can be substituted by a set of palindromic restriction enzyme sites (i.e., two similar sites in opposite orientation). The palindromic sites will loop out and hybridize together during the mutagenesis and thus form a double-stranded substrate for restriction endonuclease digestion. Cleavage of the site results in the destruction of the wild-type template. The variable region of the inserted Hc or Lc sequences will not be affected since they will be in single stranded form.

Following the methods of Example I, single-stranded Hc or Lc populations can be produced by a variety of methods known to one skilled in the art. For example, the PCR primers described in Example I can be used in asymmetric PCR to generate such populations. Gelfand et al., "PCR Protocols: A Guide to Methods and Applications", Ed by M. A. Innis (1990), which is incorporated herein by reference. Asymmetric PCR is a PCR method that differentially amplifies only a single strand of the double stranded template. Such differential amplification is accomplished by decreasing the primer amount for the undesirable strand about 10-fold compared to that for the desirable strand. Alternatively, single-stranded populations can be produced from double-stranded PCR products generated as described in Example I except that the primer(s) used to generate the undesirable strand of the double-stranded products is first phosphorylated at its 5' end with a kinase. The resultant products can then be treated with a 5' to 3' exonuclease, such as lambda exonuclease (BRL, Bethesda, Md.) to digest away the unwanted strand.

Single-stranded Hc and Lc populations generated by the methods described above or by others known to one skilled in the art are hybridized to complementary sequences encoded in the previously described vectors. The population of the sequences are subsequently incorporated into a double-stranded form of the vector by polymerase extension of the hybridized templates. Propagation and surface expression of the randomly combined Hc and Lc sequences are performed as described in Example I.

Although the invention has been described with reference to the presently preferred embodiment, it should be understood that various modifications can be made without departing from the spirit of the invention. Accordingly, the invention is limited only by the

I claim:

1. A composition of matter comprising a plurality of procaryotic cells containing diverse combinations of first and second DNA sequences encoding first and second polypeptides which form heteromeric receptors functional in the absence of its membrane attachment domain, said first and second DNA sequences contained in vectors, one or both of said polypeptides being expressed as a fusion protein with the protein product of gene VIII of a filamentous bacteriophage.

2. The composition of claim 1, wherein said plurality of cells are E. coli.

3. The composition of claim 1, wherein said heteromeric receptors are selected from the group consisting of antibodies, T cell receptors, integrins, hormone receptors and transmitter receptors.

4. The composition of claim 1, wherein said first and second DNA sequences encode functional portions of heteromeric receptors.

5. The composition of claim 4, wherein said first and second DNA sequences encode functional portions of the variable heavy and variable light chains of an antibody.

6. The composition of claim 1, wherein said cells produce filamentous bacteriophage.

7. The composition of claim 6, wherein said filamentous bacteriophage are selected from the group consisting of M13, fd and fl.

8. A cloning system for the coexpression of two or more DNA sequences encoding polypeptides which form a heteromeric receptor functional in the absence of a heteromeric receptor membrane attachment domain, comprising a set of first vectors having a diverse population of first DNA sequences and a set of second vectors having a diverse population of second DNA sequences, said first and second vectors having two pairs of restriction sites symmetrically oriented about a cloning site for containing said first and second populations of DNA sequences, said two pairs of restriction sites in an opposite orientation with respect to the cloning site on each vector, sequences between said first pair of restriction sites in said two vectors being homologous enough to allow annealing, and sequences between said second pair of restriction sites in said two vectors being homologous enough to allow annealing, so as to allow only the operational combination of vector sequences containing said first and second DNA sequences.

9. The cloning system of claim 8, wherein said first and second vectors are circular.

10. The cloning system of claim 8, wherein said heteromeric receptors are selected from the group consisting of antibodies, T cell receptors, integrins, hormone receptors and transmitter receptors.

11. The cloning system of claim 8, wherein said first and second DNA sequences encode functional portions of heteromeric receptors.

12. The cloning system of claim 11, wherein said first and second DNA sequences encode functional portions of the variable heavy and variable light chains of an antibody.

13. The cloning system of claim 8, wherein said coexpression of two or more DNA sequences encoding polypeptides which form a heteromeric receptor is on the surface of cell.

14. The cloning system of claim 8, wherein said first and second vectors are filamentous bacteriophage vectors.

15. The cloning system of claim 14 wherein said filamentous bacteriophage are selected from the group consisting of M13, fd and fl.

16. The cloning system of claim 15, wherein at least one of the DNA sequences encodes a fusion protein with the protein product of gene VIII.

17. The cloning system of claim 8, wherein said two pairs of restriction sites are Hind III-Mlu I and Hind III-Mlu I.

18. A plurality of expression vectors, each vector containing a first and second DNA sequence encoding a first and second polypeptide of a heteromeric receptor, which form a plurality of heteromeric receptors functional in the absence of a heteromeric receptor membrane attachment domain, one or more of said receptors exhibiting binding activity toward a preselected molecule, said first or second DNA sequence being operatively linked to gene VIII of a filamentous bacteriophage.

19. The expression vectors of claim 18, wherein said expression vectors are circular.

20. The expression vectors of claim 18, wherein said heteromeric receptors are selected from the group consisting of antibodies, T cell receptors, integrins, hormone receptors and transmitter receptors.

21. The expression vectors of claim 18, wherein said first and second DNA sequences encode functional portions of heterameric receptors.

22. The expression vectors of claim 21, wherein said first and second DNA sequences encode functional portions of the variable heavy and variable light chains of an antibody.

23. The expression vectors of claim 18, wherein said expression vectors are filamentous bacteriophage vectors.

24. The expression vectors of claim 18, wherein said filamentous bacteriophage are selected from the group consisting of M13, fd and fl.

25. A vector comprising two copies of a gene encoding a filamentous bacteriophage coat protein, one copy of said gene being operationally linked to a DNA sequence encoding a polypeptide of a heteromeric receptor functional in the absence of a heteromeric receptor membrane attachment domain, said DNA sequence being expressed as a polypeptide of a fusion protein comprising said heteromeric receptor on the surface of said filamentous bacteriophage or as a soluble polypeptide.

26. The vector of claim 25, wherein said two copies of said gene encode substantially the same amino acid sequence but have different nucleotide sequences.

27. The vector of claim 25, wherein said one copy of said gene is expressed on the surface of said filamentous bacteriophage.

28. The vector of claim 25, wherein said bacteriophage coat protein is M13 gene VIII.

29. The vector of claim 25, wherein said vector has substantially the same sequence as that shown in FIG. 2 (SEQ ID NO: 1).

30. A vector comprising sequences necessary for the coexpression of two or more inserted DNA sequences encoding polypeptides which form heteromeric receptors and two copies of a gene encoding a filamentous bacteriophage coat protein, one copy of said gene being operationally linked to one of said two or more inserted DNA sequences, said DNA sequence being expressed as a polypeptide of a fusion protein comprising said heteromeric receptor on the surface of said filamentous bacteriophage or as a soluble polypeptide.

31. The expression vectors of claim 26, wherein said expression vectors are filamentous bacteriophage vectors.

32. The vector of claim 30, wherein said one copy of said gene is expressed on the surface of said filamentous bacteriophage.

33. The vector of claim 30, wherein said bacteriophage coat protein is M13 gene VIII.

34. The vector of claim 30, wherein said vector has substantially the same sequence as that shown in FIG. 6 (SEQ ID NO: 5).

* * * * *

SEQUENCE LISTING (1) GENERAL INFORMATION:

(iii) NUMBER OF SEQUENCES: 76

(2) INFORMATION FOR SEQ ID NO:1:

(i) SEQUENCE CHARACTERISTICS:
      (A) LENGTH: 7445 base pairs
      (B) TYPE: nucleic acid
      (C) STRANDEDNESS: both
      (D) TOPOLOGY: circular (xi) SEQUENCE DESCRIPTION: SEQ ID NO:1:

```
AATGCTACTA CTATTAGTAG AATTGATGCC ACCTTTTCAG CTCGCGCCCC AAATGAAAAT      60

ATAGCTAAAC AGGTTATTGA CCATTTGCGA AATGTATCTA ATGGTCAAAC TAAATCTACT     120

CGTTCGCAGA ATTGGGAATC AACTGTTACA TGGAATGAAA CTTCCAGACA CCGTACTTTA     180

GTTGCATATT TAAAACATGT TGAGCTACAG CACCAGATTC AGCAATTAAG CTCTAAGCCA     240

TCTGCAAAAA TGACCTCTTA TCAAAAGGAG CAATTAAAGG TACTCTCTAA TCCTGACCTG     300

TTGGAGTTTG CTTCCGGTCT GGTTCGCTTT GAAGCTCGAA TTAAAACGCG ATATTTGAAG     360

TCTTTCGGGC TTCCTCTTAA TCTTTTTGAT GCAATCCGCT TTGCTTCTGA CTATAATAGT     420

CAGGGTAAAG ACCTGATTTT TGATTTATGG TCATTCTCGT TTTCTGAACT GTTTAAAGCA     480

TTTGAGGGGG ATTCAATGAA TATTTATGAC GATTCCGCAG TATTGGACGC TATCCAGTCT     540

AAACATTTTA CTATTACCCC CTCTGGCAAA ACTTCTTTTG CAAAAGCCTC TCGCTATTTT     600

GGTTTTTATC GTCGTCTGGT AAACGAGGGT TATGATAGTG TTGCTCTTAC TATGCCTCGT     660

AATTCCTTTT GGCGTTATGT ATCTGCATTA GTTGAATGTG GTATTCCTAA ATCTCAACTG     720

ATGAATCTTT CTACCTGTAA TAATGTTGTT CCGTTAGTTC GTTTTATTAA CGTAGATTTT     780

TCTTCCCAAC GTCCTGACTG GTATAATGAG CCAGTTCTTA AAATCGCATA AGGTAATTCA     840

CAATGATTAA AGTTGAAATT AAACCATCTC AAGCCCAATT TACTACTCGT TCTGGTGTTT     900

CTCGTCAGGG CAAGCCTTAT TCACTGAATG AGCAGCTTTG TTACGTTGAT TTGGGTAATG     960

AATATCCGGT TCTTGTCAAG ATTACTCTTG ATGAAGGTCA GCCAGCCTAT GCGCCTGGTC    1020

TGTACACCGT TCATCTGTCC TCTTTCAAAG TTGGTCAGTT CGGTTCCCTT ATGATTGACC    1080

GTCTGCGCCT CGTTCCGGCT AAGTAACATG GAGCAGGTCG CGGATTTCGA CACAATTTAT    1140

CAGGCGATGA TACAAATCTC CGTTGTACTT TGTTTCGCGC TTGGTATAAT CGCTGGGGGT    1200
```

```
CAAAGATGAG TGTTTTAGTG TATTCTTTCG CCTCTTTCGT TTTAGGTTGG TGCCTTCGTA    1260

GTGGCATTAC GTATTTTACC CGTTTAATGG AAACTTCCTC ATGAAAAAGT CTTTAGTCCT    1320

CAAAGCCTCT GTAGCCGTTG CTACCCTCGT TCCGATGCTG TCTTTCGCTG CTGAGGGTGA    1380

CGATCCCGCA AAAGCGGCCT TTAACTCCCT GCAAGCCTCA GCGACCGAAT ATATCGGTTA    1440

TGCGTGGGCG ATGGTTGTTG TCATTGTCGG CGCAACTATC GGTATCAAGC TGTTTAAGAA    1500

ATTCACCTCG AAAGCAAGCT GATAAACCGA TACAATTAAA GGCTCCTTTT GGAGCCTTTT    1560

TTTTTGGAGA TTTTCAACGT GAAAAAATTA TTATTCGCAA TTCCTTTAGT TGTTCCTTTC    1620

TATTCTCACT CCGCTGAAAC TGTTGAAAGT TGTTTAGCAA ACCCCATAC AGAAAATTCA     1680

TTTACTAACG TCTGGAAAGA CGACAAAACT TTAGATCGTT ACGCTAACTA TGAGGGTTGT    1740

CTGTGGAATG CTACAGGCGT TGTAGTTTGT ACTGGTGACG AAACTCAGTG TTACGGTACA    1800

TGGGTTCCTA TTGGGCTTGC TATCCCTGAA AATGAGGGTG GTGGCTCTGA GGGTGGCGGT    1860

TCTGAGGGTG GCGGTTCTGA GGGTGGCGGT ACTAAACCTC CTGAGTACGG TGATACACCT    1920

ATTCCGGGCT ATACTTATAT CAACCCTCTC GACGGCACTT ATCCGCCTGG TACTGAGCAA    1980

AACCCCGCTA ATCCTAATCC TTCTCTTGAG GAGTCTCAGC CTCTTAATAC TTTCATGTTT    2040

CAGAATAATA GGTTCCGAAA TAGGCAGGGG GCATTAACTG TTTATACGGG CACTGTTACT    2100

CAAGGCACTG ACCCCGTTAA AACTTATTAC CAGTACACTC CTGTATCATC AAAAGCCATG    2160

TATGACGCTT ACTGGAACGG TAAATTCAGA GACTGCGCTT CCATTCTGG CTTTAATGAA     2220

GATCCATTCG TTTGTGAATA TCAAGGCCAA TCGTCTGACC TGCCTCAACC TCCTGTCAAT    2280

GCTGGCGGCG GCTCTGGTGG TGGTTCTGGT GGCGGCTCTG AGGGTGGTGG CTCTGAGGGT    2340

GGCGGTTCTG AGGGTGGCGG CTCTGAGGGA GGCGGTTCCG GTGGTGGCTC TGGTTCCGGT    2400

GATTTTGATT ATGAAAAGAT GGCAAACGCT AATAAGGGGG CTATGACCGA AAATGCCGAT    2460

GAAAACGCGC TACAGTCTGA CGCTAAAGGC AAACTTGATT CTGTCGCTAC TGATTACGGT    2520

GCTGCTATCG ATGGTTTCAT TGGTGACGTT TCCGGCCTTG CTAATGGTAA TGGTGCTACT    2580

GGTGATTTTG CTGGCTCTAA TTCCCAAATG GCTCAAGTCG GTGACGGTGA TAATTCACCT    2640

TTAATGAATA ATTTCCGTCA ATATTTACCT TCCCTCCCTC AATCGGTTGA ATGTCGCCCT    2700

TTTGTCTTTA GCGCTGGTAA ACCATATGAA TTTTCTATTG ATTGTGACAA AATAAACTTA    2760

TTCCGTGGTG TCTTTGCGTT TCTTTTATAT GTTGCCACCT TTATGTATGT ATTTTCTACG    2820

TTTGCTAACA TACTGCGTAA TAAGGAGTCT TAATCATGCC AGTTCTTTTG GGTATTCCGT    2880

TATTATTGCG TTTCCTCGGT TTCCTTCTGG TAACTTTGTT CGGCTATCTG CTTACTTTTC    2940

TTAAAAAGGG CTTCGGTAAG ATAGCTATTG CTATTTCATT GTTTCTTGCT CTTATTATTG    3000

GGCTTAACTC AATTCTTGTG GGTTATCTCT CTGATATTAG CGCTCAATTA CCCTCTGACT    3060

TTGTTCAGGG TGTTCAGTTA ATTCTCCCGT CTAATGCGCT TCCCTGTTTT TATGTTATTC    3120

TCTCTGTAAA GGCTGCTATT TTCATTTTTG ACGTTAAACA AAAAATCGTT TCTTATTTGG    3180

ATTGGGATAA ATAATATGGC TGTTTATTTT GTAACTGGCA AATTAGGCTC TGGAAAGACG    3240

CTCGTTAGCG TTGGTAAGAT TCAGGATAAA ATTGTAGCTG GTGCAAAAT AGCAACTAAT     3300

CTTGATTTAA GGCTTCAAAA CCTCCCGCAA GTCGGGAGGT TCGCTAAAAC GCCTCGCGTT    3360

CTTAGAATAC CGGATAAGCC TTCTATATCT GATTTGCTTG CTATTGGGCG CGGTAATGAT    3420

TCCTACGATG AAAATAAAAA CGGCTTGCTT GTTCTCGATG AGTGCGGTAC TTGGTTTAAT    3480

ACCCGTTCTT GGAATGATAA GGAAAGACAG CCGATTATTG ATTGGTTTCT ACATGCTCGT    3540
```

```
AAATTAGGAT GGGATATTAT TTTTCTTGTT CAGGACTTAT CTATTGTTGA TAAACAGGCG   3600

CGTTCTGCAT TAGCTGAACA TGTTGTTTAT TGTCGTCGTC TGGACAGAAT TACTTTACCT   3660

TTTGTCGGTA CTTTATATTC TCTTATTACT GGCTCGAAAA TGCCTCTGCC TAAATTACAT   3720

GTTGGCGTTG TTAAATATGG CGATTCTCAA TTAAGCCCTA CTGTTGAGCG TTGGCTTTAT   3780

ACTGGTAAGA ATTTGTATAA CGCATATGAT ACTAAACAGG CTTTTTCTAG TAATTATGAT   3840

TCCGGTGTTT ATTCTTATTT AACGCCTTAT TTATCACACG GTCGGTATTT CAAACCATTA   3900

AATTTAGGTC AGAAGATGAA GCTTACTAAA ATATATTTGA AAAAGTTTTC ACGCGTTCTT   3960

TGTCTTGCGA TTGGATTTGC ATCAGCATTT ACATATAGTT ATATAACCCA ACCTAAGCCG   4020

GAGGTTAAAA AGGTAGTCTC TCAGACCTAT GATTTTGATA AATTCACTAT TGACTCTTCT   4080

CAGCGTCTTA ATCTAAGCTA TCGCTATGTT TTCAAGGATT CTAAGGGAAA ATTAATTAAT   4140

AGCGACGATT TACAGAAGCA AGGTTATTCA CTCACATATA TTGATTTATG TACTGTTTCC   4200

ATTAAAAAAG GTAATTCAAA TGAAATTGTT AAATGTAATT AATTTTGTTT TCTTGATGTT   4260

TGTTTCATCA TCTTCTTTTG CTCAGGTAAT TGAAATGAAT AATTCGCCTC TGCGCGATTT   4320

TGTAACTTGG TATTCAAAGC AATCAGGCGA ATCCGTTATT GTTTCTCCCG ATGTAAAAGG   4380

TACTGTTACT GTATATTCAT CTGACGTTAA ACCTGAAAAT CTACGCAATT TCTTTATTTC   4440

TGTTTTACGT GCTAATAATT TTGATATGGT TGGTTCAATT CCTTCCATAA TTCAGAAGTA   4500

TAATCCAAAC AATCAGGATT ATATTGATGA ATTGCCATCA TCTGATAATC AGGAATATGA   4560

TGATAATTCC GCTCCTTCTG GTGGTTTCTT TGTTCCGCAA AATGATAATG TTACTCAAAC   4620

TTTTAAAATT AATAACGTTC GGGCAAAGGA TTTAATACGA GTTGTCGAAT TGTTTGTAAA   4680

GTCTAATACT TCTAAATCCT CAAATGTATT ATCTATTGAC GGCTCTAATC TATTAGTTGT   4740

TAGTGCACCT AAAGATATTT TAGATAACCT TCCTCAATTC CTTTCTACTG TTGATTTGCC   4800

AACTGACCAG ATATTGATTG AGGGTTTGAT ATTTGAGGTT CAGCAAGGTG ATGCTTTAGA   4860

TTTTTCATTT GCTGCTGGCT CTCAGCGTGG CACTGTTGCA GGCGGTGTTA ATACTGACCG   4920

CCTCACCTCT GTTTTATCTT CTGCTGGTGG TTCGTTCGGT ATTTTTAATG GCGATGTTTT   4980

AGGGCTATCA GTTCGCGCAT TAAAGACTAA TAGCCATTCA AAAATATTGT CTGTGCCACG   5040

TATTCTTACG CTTTCAGGTC AGAAGGGTTC TATCTCTGTT GGCCAGAATG TCCCTTTTAT   5100

TACTGGTCGT GTGACTGGTG AATCTGCCAA TGTAAATAAT CCATTTCAGA CGATTGAGCG   5160

TCAAAATGTA GGTATTTCCA TGAGCGTTTT TCCTGTTGCA ATGGCTGGCG GTAATATTGT   5220

TCTGGATATT ACCAGCAAGG CCGATAGTTT GAGTTCTTCT ACTCAGGCAA GTGATGTTAT   5280

TACTAATCAA AGAAGTATTG CTACAACGGT TAATTTGCGT GATGGACAGA CTCTTTTACT   5340

CGGTGGCCTC ACTGATTATA AAAACACTTC TCAAGATTCT GGCGTACCGT TCCTGTCTAA   5400

AATCCCTTTA ATCGGCCTCC TGTTTAGCTC CCGCTCTGAT TCCAACGAGG AAAGCACGTT   5460

ATACGTGCTC GTCAAAGCAA CCATAGTACG CGCCCTGTAG CGGCGCATTA AGCGCGGCGG   5520

GTGTGGTGGT TACGCGCAGC GTGACCGCTA CACTTGCCAG CGCCCTAGCG CCCGCTCCTT   5580

TCGCTTTCTT CCCTTCCTTT CTCGCCACGT TCGCCGGCTT TCCCCGTCAA GCTCTAAATC   5640

GGGGGCTCCC TTTAGGGTTC CGATTTAGTG CTTTACGGCA CCTCGACCCC AAAAAACTTG   5700

ATTTGGGTGA TGGTTCACGT AGTGGGCCAT CGCCCTGATA GACGGTTTTT CGCCCTTTGA   5760

CGTTGGAGTC CACGTTCTTT AATAGTGGAC TCTTGTTCCA AACTGGAACA ACACTCAACC   5820

CTATCTCGGG CTATTCTTTT GATTTATAAG GGATTTTGCC GATTTCGGAA CCACCATCAA   5880

ACAGGATTTT CGCCTGCTGG GGCAAACCAG CGTGGACCGC TTGCTGCAAC TCTCTCAGGG   5940
```

-continued

```
CCAGGCGGTG AAGGGCAATC AGCTGTTGCC CGTCTCGCTG GTGAAAAGAA AAACCACCCT      6000

GGCGCCCAAT ACGCAAACCG CCTCTCCCCG CGCGTTGGCC GATTCATTAA TGCAGCTGGC      6060

ACGACAGGTT TCCCGACTGG AAAGCGGGCA GTGAGCGCAA CGCAATTAAT GTGAGTTAGC      6120

TCACTCATTA GGCACCCCAG GCTTTACACT TTATGCTTCC GGCTCGTATG TTGTGTGGAA      6180

TTGTGAGCGG ATAACAATTT CACACGCGTC ACTTGGCACT GGCCGTCGTT TTACAACGTC      6240

GTGACTGGGA AAACCCTGGC GTTACCCAAG CTTTGTACAT GGAGAAAATA AAGTGAAACA      6300

AAGCACTATT GCACTGGCAC TCTTACCGTT ACCGTTACTG TTTACCCCTG TGACAAAAGC      6360

CGCCCAGGTC CAGCTGCTCG AGTCAGGCCT ATTGTGCCCA GGGGATTGTA CTAGTGGATC      6420

CTAGGCTGAA GGCGATGACC CTGCTAAGGC TGCATTCAAT AGTTTACAGG CAAGTGCTAC      6480

TGAGTACATT GGCTACGCTT GGGCTATGGT AGTAGTTATA GTTGGTGCTA CCATAGGGAT      6540

TAAATTATTC AAAAGTTTA CGAGCAAGGC TTCTTAAGCA ATAGCGAAGA GGCCCGCACC       6600

GATCGCCCTT CCCAACAGTT GCGCAGCCTG AATGGCGAAT GGCGCTTTGC CTGGTTTCCG      6660

GCACCAGAAG CGGTGCCGGA AAGCTGGCTG GAGTGCGATC TTCCTGAGGC CGATACGGTC      6720

GTCGTCCCCT CAAACTGGCA GATGCACGGT TACGATGCGC CCATCTACAC CAACGTAACC      6780

TATCCCATTA CGGTCAATCC GCCGTTTGTT CCCACGGAGA ATCCGACGGG TTGTTACTCG      6840

CTCACATTTA ATGTTGATGA AAGCTGGCTA CAGGAAGGCC AGACGCGAAT TATTTTTGAT      6900

GGCGTTCCTA TTGGTTAAAA AATGAGCTGA TTTAACAAAA ATTTAACGCG AATTTTAACA      6960

AAATATTAAC GTTTACAATT TAAATATTTG CTTATACAAT CTTCCTGTTT TTGGGGCTTT      7020

TCTGATTATC AACCGGGGTA CATATGATTG ACATGCTAGT TTTACGATTA CCGTTCATCG      7080

ATTCTCTTGT TTGCTCCAGA CTCTCAGGCA ATGACCTGAT AGCCTTTGTA GATCTCTCAA      7140

AAATAGCTAC CCTCTCCGGC ATTAATTTAT CAGCTAGAAC GGTTGAATAT CATATTGATG      7200

GTGATTTGAC TGTCTCCGGC CTTTCTCACC CTTTTGAATC TTTACCTACA CATTACTCAG      7260

GCATTGCATT TAAAATATAT GAGGGTTCTA AAAATTTTTA TCCTTGCGTT GAAATAAAGG      7320

CTTCTCCCGC AAAAGTATTA CAGGGTCATA ATGTTTTTGG TACAACCGAT TTAGCTTTAT      7380

GCTCTGAGGC TTTATTGCTT AATTTTGCTA ATTCTTTGCC TTGCCTGTAT GATTTATTGG      7440

ACGTT                                                                 7445
```

(2) INFORMATION FOR SEQ ID NO:2:

(i) SEQUENCE CHARACTERISTICS:
        (A) LENGTH: 7317 base pairs
        (B) TYPE: nucleic acid
        (C) STRANDEDNESS: both
        (D) TOPOLOGY: circular (xi) SEQUENCE DESCRIPTION: SEQ ID NO:2:

```
AATGCTACTA CTATTAGTAG AATTGATGCC ACCTTTTCAG CTCGCGCCCC AAATGAAAAT       60

ATAGCTAAAC AGGTTATTGA CCATTTGCGA AATGTATCTA ATGGTCAAAC TAAATCTACT      120

CGTTCGCAGA ATTGGGAATC AACTGTTACA TGGAATGAAA CTTCCAGACA CCGTACTTTA      180

GTTGCATATT TAAAACATGT TGAGCTACAG CACCAGATTC AGCAATTAAG CTCTAAGCCA      240

TCCGCAAAAA TGACCTCTTA TCAAAAGGAG CAATTAAAGG TACTCTCTAA TCCTGACCTG      300

TTGGAGTTTG CTTCCGGTCT GGTTCGCTTT GAAGCTCGAA TTAAAACGCG ATATTTGAAG      360

TCTTTCGGGC TTCCTCTTAA TCTTTTTGAT GCAATCCGCT TTGCTTCTGA CTATAATAGT      420

CAGGGTAAAG ACCTGATTTT TGATTTATGG TCATTCTCGT TTTCTGAACT GTTTAAAGCA      480
```

```
TTTGAGGGGG ATTCAATGAA TATTTATGAC GATTCCGCAG TATTGGACGC TATCCAGTCT      540

AAACATTTTA CTATTACCCC CTCTGGCAAA ACTTCTTTTG CAAAAGCCTC TCGCTATTTT      600

GGTTTTTATC GTCGTCTGGT AAACGAGGGT TATGATAGTG TTGCTCTTAC TATGCCTCGT      660

AATTCCTTTT GGCGTTATGT ATCTGCATTA GTTGAATGTG GTATTCCTAA ATCTCAACTG      720

ATGAATCTTT CTACCTGTAA TAATGTTGTT CCGTTAGTTC GTTTTATTAA CGTAGATTTT      780

TCTTCCCAAC GTCCTGACTG GTATAATGAG CCAGTTCTTA AAATCGCATA AGGTAATTCA      840

CAATGATTAA AGTTGAAATT AAACCATCTC AAGCCCAATT TACTACTCGT TCTGGTGTTT      900

CTCGTCAGGG CAAGCCTTAT TCACTGAATG AGCAGCTTTG TTACGTTGAT TTGGGTAATG      960

AATATCCGGT TCTTGTCAAG ATTACTCTTG ATGAAGGTCA GCCAGCCTAT GCGCCTGGTC     1020

TGTACACCGT TCATCTGTCC TCTTTCAAAG TTGGTCAGTT CGGTTCCCTT ATGATTGACC     1080

GTCTGCGCCT CGTTCCGGCT AAGTAACATG GAGCAGGTCG CGGATTTCGA CACAATTTAT     1140

CAGGCGATGA TACAAATCTC CGTTGTACTT TGTTTCGCGC TTGGTATAAT CGCTGGGGGT     1200

CAAAGATGAG TGTTTTAGTG TATTCTTTCG CCTCTTTCGT TTTAGGTTGG TGCCTTCGTA     1260

GTGGCATTAC GTATTTTACC CGTTTAATGG AAACTTCCTC ATGAAAAAGT CTTTAGTCCT     1320

CAAAGCCTCT GTAGCCGTTG CTACCCTCGT TCCGATGCTG TCTTTCGCTG CTGAGGGTGA     1380

CGATCCCGCA AAAGCGGCCT TTAACTCCCT GCAAGCCTCA GCGACCGAAT ATATCGGTTA     1440

TGCGTGGGCG ATGGTTGTTG TCATTGTCGG CGCAACTATC GGTATCAAGC TGTTTAAGAA     1500

ATTCACCTCG AAAGCAAGCT GATAAACCGA TACAATTAAA GGCTCCTTTT GGAGCCTTTT     1560

TTTTTGGAGA TTTTCAACGT GAAAAAATTA TTATTCGCAA TTCCTTTAGT TGTTCCTTTC     1620

TATTCTCACT CCGCTGAAAC TGTTGAAAGT TGTTTAGCAA AACCCCATAC AGAAAATTCA     1680

TTTACTAACG TCTGGAAAGA CGACAAAACT TTAGATCGTT ACGCTAACTA TGAGGGTTGT     1740

CTGTGGAATG CTACAGGCGT TGTAGTTTGT ACTGGTGACG AAACTCAGTG TTACGGTACA     1800

TGGGTTCCTA TTGGGCTTGC TATCCCTGAA AATGAGGGTG GTGGCTCTGA GGGTGGCGGT     1860

TCTGAGGGTG GCGGTTCTGA GGGTGGCGGT ACTAAACCTC CTGAGTACGG TGATACACCT     1920

ATTCCGGGCT ATACTTATAT CAACCCTCTC GACGGCACTT ATCCGCCTGG TACTGAGCAA     1980

AACCCCGCTA ATCCTAATCC TTCTCTTGAG GAGTCTCAGC CTCTTAATAC TTTCATGTTT     2040

CAGAATAATA GGTTCCGAAA TAGGCAGGGG GCATTAACTG TTTATACGGG CACTGTTACT     2100

CAAGGCACTG ACCCCGTTAA AACTTATTAC CAGTACACTC CTGTATCATC AAAAGCCATG     2160

TATGACGCTT ACTGGAACGG TAAATTCAGA GACTGCGCTT CCATTCTGG CTTTAATGAA      2220

GATCCATTCG TTTGTGAATA TCAAGGCCAA TCGTCTGACC TGCCTCAACC TCCTGTCAAT     2280

GCTGGCGGCG GCTCTGGTGG TGGTTCTGGT GGCGGCTCTG AGGGTGGTGG CTCTGAGGGT     2340

GGCGGTTCTG AGGGTGGCGG CTCTGAGGGA GGCGGTTCCG GTGGTGGCTC TGGTTCCGGT     2400

GATTTTGATT ATGAAAAGAT GGCAAACGCT AATAAGGGGG CTATGACCGA AAATGCCGAT     2460

GAAAACGCGC TACAGTCTGA CGCTAAAGGC AAACTTGATT CTGTCGCTAC TGATTACGGT     2520

GCTGCTATCG ATGGTTTCAT TGGTGACGTT TCCGGCCTTG CTAATGGTAA TGGTGCTACT     2580

GGTGATTTTG CTGGCTCTAA TTCCCAAATG GCTCAAGTCG GTGACGGTGA TAATTCACCT     2640

TTAATGAATA ATTTCCGTCA ATATTTACCT TCCCTCCCTC AATCGGTTGA ATGTCGCCCT     2700

TTTGTCTTTA GCGCTGGTAA ACCATATGAA TTTTCTATTG ATTGTGACAA AATAAACTTA     2760

TTCCGTGGTG TCTTTGCGTT TCTTTTATAT GTTGCCACCT TTATGTATGT ATTTTCTACG     2820
```

-continued

| | | | | | |
|---|---|---|---|---|---|
| TTTGCTAACA | TACTGCGTAA | TAAGGAGTCT | TAATCATGCC | AGTTCTTTTG | GGTATTCCGT | 2880 |
| TATTATTGCG | TTTCCTCGGT | TTCCTTCTGG | TAACTTTGTT | CGGCTATCTG | CTTACTTTTC | 2940 |
| TTAAAAAGGG | CTTCGGTAAG | ATAGCTATTG | CTATTTCATT | GTTTCTTGCT | CTTATTATTG | 3000 |
| GGCTTAACTC | AATTCTTGTG | GGTTATCTCT | CTGATATTAG | CGCTCAATTA | CCCTCTGACT | 3060 |
| TTGTTCAGGG | TGTTCAGTTA | ATTCTCCCGT | CTAATGCGCT | TCCCTGTTTT | TATGTTATTC | 3120 |
| TCTCTGTAAA | GGCTGCTATT | TTCATTTTTG | ACGTTAAACA | AAAAATCGTT | TCTTATTTGG | 3180 |
| ATTGGGATAA | ATAATATGGC | TGTTTATTTT | GTAACTGGCA | AATTAGGCTC | TGGAAAGACG | 3240 |
| CTCGTTAGCG | TTGGTAAGAT | TCAGGATAAA | ATTGTAGCTG | GGTGCAAAAT | AGCAACTAAT | 3300 |
| CTTGATTTAA | GGCTTCAAAA | CCTCCCGCAA | GTCGGGAGGT | TCGCTAAAAC | GCCTCGCGTT | 3360 |
| CTTAGAATAC | CGGATAAGCC | TTCTATATCT | GATTTGCTTG | CTATTGGGCG | CGGTAATGAT | 3420 |
| TCCTACGATG | AAAATAAAAA | CGGCTTGCTT | GTTCTCGATG | AGTGCGGTAC | TTGGTTTAAT | 3480 |
| ACCCGTTCTT | GGAATGATAA | GGAAAGACAG | CCGATTATTG | ATTGGTTTCT | ACATGCTCGT | 3540 |
| AAATTAGGAT | GGGATATTAT | TTTTCTTGTT | CAGGACTTAT | CTATTGTTGA | TAAACAGGCG | 3600 |
| CGTTCTGCAT | TAGCTGAACA | TGTTGTTTAT | TGTCGTCGTC | TGGACAGAAT | TACTTTACCT | 3660 |
| TTTGTCGGTA | CTTTATATTC | TCTTATTACT | GGCTCGAAAA | TGCCTCTGCC | TAAATTACAT | 3720 |
| GTTGGCGTTG | TTAAATATGG | CGATTCTCAA | TTAAGCCCTA | CTGTTGAGCG | TTGGCTTTAT | 3780 |
| ACTGGTAAGA | ATTTGTATAA | CGCATATGAT | ACTAAACAGG | CTTTTTCTAG | TAATTATGAT | 3840 |
| TCCGGTGTTT | ATTCTTATTT | AACGCCTTAT | TTATCACACG | GTCGGTATTT | CAAACCATTA | 3900 |
| AATTTAGGTC | AGAAGATGAA | GCTTACTAAA | ATATATTTGA | AAAGTTTTC | ACGCGTTCTT | 3960 |
| TGTCTTGCGA | TTGGATTTGC | ATCAGCATTT | ACATATAGTT | ATATAACCCA | ACCTAAGCCG | 4020 |
| GAGGTTAAAA | AGGTAGTCTC | TCAGACCTAT | GATTTTGATA | AATTCACTAT | TGACTCTTCT | 4080 |
| CAGCGTCTTA | ATCTAAGCTA | TCGCTATGTT | TTCAAGGATT | CTAAGGGAAA | ATTAATTAAT | 4140 |
| AGCGACGATT | TACAGAAGCA | AGGTTATTCA | CTCACATATA | TTGATTTATG | TACTGTTTCC | 4200 |
| ATTAAAAAAG | GTAATTCAAA | TGAAATTGTT | AAATGTAATT | AATTTTGTTT | TCTTGATGTT | 4260 |
| TGTTTCATCA | TCTTCTTTTG | CTCAGGTAAT | TGAAATGAAT | AATTCGCCTC | TGCGCGATTT | 4320 |
| TGTAACTTGG | TATTCAAAGC | AATCAGGCGA | ATCCGTTATT | GTTTCTCCCG | ATGTAAAAGG | 4380 |
| TACTGTTACT | GTATATTCAT | CTGACGTTAA | ACCTGAAAAT | CTACGCAATT | TCTTTATTTC | 4440 |
| TGTTTTACGT | GCTAATAATT | TTGATATGGT | TGGTTCAATT | CCTTCCATAA | TTCAGAAGTA | 4500 |
| TAATCCAAAC | AATCAGGATT | ATATTGATGA | ATTGCCATCA | TCTGATAATC | AGGAATATGA | 4560 |
| TGATAATTCC | GCTCCTTCTG | GTGGTTTCTT | TGTTCCGCAA | AATGATAATG | TTACTCAAAC | 4620 |
| TTTTAAAATT | AATAACGTTC | GGGCAAAGGA | TTTAATACGA | GTTGTCGAAT | TGTTTGTAAA | 4680 |
| GTCTAATACT | TCTAAATCCT | CAAATGTATT | ATCTATTGAC | GGCTCTAATC | TATTAGTTGT | 4740 |
| TAGTGCACCT | AAAGATATTT | TAGATAACCT | TCCTCAATTC | CTTTCTACTG | TTGATTTGCC | 4800 |
| AACTGACCAG | ATATTGATTG | AGGGTTTGAT | ATTTGAGGTT | CAGCAAGGTG | ATGCTTTAGA | 4860 |
| TTTTTCATTT | GCTGCTGGCT | CTCAGCGTGG | CACTGTTGCA | GGCGGTGTTA | ATACTGACCG | 4920 |
| CCTCACCTCT | GTTTTATCTT | CTGCTGGTGG | TTCGTTCGGT | ATTTTTAATG | GCGATGTTTT | 4980 |
| AGGGCTATCA | GTTCGCGCAT | TAAAGACTAA | TAGCCATTCA | AAAATATTGT | CTGTGCCACG | 5040 |
| TATTCTTACG | CTTTCAGGTC | AGAAGGGTTC | TATCTCTGTT | GGCCAGAATG | TCCCTTTTAT | 5100 |
| TACTGGTCGT | GTGACTGGTG | AATCTGCCAA | TGTAAATAAT | CCATTTCAGA | CGATTGAGCG | 5160 |
| TCAAAATGTA | GGTATTTCCA | TGAGCGTTTT | TCCTGTTGCA | ATGGCTGGCG | GTAATATTGT | 5220 |

-continued

```
TCTGGATATT ACCAGCAAGG CCGATAGTTT GAGTTCTTCT ACTCAGGCAA GTGATGTTAT      5280

TACTAATCAA AGAAGTATTG CTACAACGGT TAATTTGCGT GATGGACAGA CTCTTTTACT      5340

CGGTGGCCTC ACTGATTATA AAAACACTTC TCAAGATTCT GGCGTACCGT TCCTGTCTAA      5400

AATCCCTTTA ATCGGCCTCC TGTTTAGCTC CCGCTCTGAT TCCAACGAGG AAAGCACGTT      5460

ATACGTGCTC GTCAAAGCAA CCATAGTACG CGCCCTGTAG CGGCGCATTA AGCGCGGCGG      5520

GTGTGGTGGT TACGCGCAGC GTGACCGCTA CACTTGCCAG CGCCCTAGCG CCCGCTCCTT      5580

TCGCTTTCTT CCCTTCCTTT CTCGCCACGT TCGCCGGCTT TCCCCGTCAA GCTCTAAATC      5640

GGGGGCTCCC TTTAGGGTTC CGATTTAGTG CTTTACGGCA CCTCGACCCC AAAAAACTTG      5700

ATTTGGGTGA TGGTTCACGT AGTGGGCCAT CGCCCTGATA GACGGTTTTT CGCCCTTTGA      5760

CGTTGGAGTC CACGTTCTTT AATAGTGGAC TCTTGTTCCA AACTGGAACA ACACTCAACC      5820

CTATCTCGGG CTATTCTTTT GATTTATAAG GGATTTTGCC GATTTCGGAA CCACCATCAA      5880

ACAGGATTTT CGCCTGCTGG GGCAAACCAG CGTGGACCGC TTGCTGCAAC TCTCTCAGGG      5940

CCAGGCGGTG AAGGGCAATC AGCTGTTGCC CGTCTCGCTG GTGAAAAGAA AAACCACCCT      6000

GGCGCCCAAT ACGCAAACCG CCTCTCCCCG CGCGTTGGCC GATTCATTAA TGCAGCTGGC      6060

ACGACAGGTT TCCCGACTGG AAAGCGGGCA GTGAGCGCAA CGCAATTAAT GTGAGTTAGC      6120

TCACTCATTA GGCACCCCAG GCTTTACACT TTATGCTTCC GGCTCGTATG TTGTGTGGAA      6180

TTGTGAGCGG ATAACAATTT CACACGCCAA GGAGACAGTC ATAATGAAAT ACCTATTGCC      6240

TACGGCAGCC GCTGGATTGT TATTACTCGC TGCCCAACCA GCCATGGCCG AGCTCGTGAT      6300

GACCCAGACT CCAGATATCC AACAGGAATG AGTGTTAATT CTAGAACGCG TCACTTGGCA      6360

CTGGCCGTCG TTTTACAACG TCGTGACTGG GAAAACCCTG GCGTTACCCA AGCTTAATCG      6420

CCTTGCAGAA TTCCCTTTCG CCAGCTGGCG TAATAGCGAA GAGGCCCGCA CCGATCGCCC      6480

TTCCCAACAG TTGCGCAGCC TGAATGGCGA ATGGCGCTTT GCCTGGTTTC CGGCACCAGA      6540

AGCGGTGCCG GAAAGCTGGC TGGAGTGCGA TCTTCCTGAG GCCGATACGG TCGTCGTCCC      6600

CTCAAACTGG CAGATGCACG GTTACGATGC GCCCATCTAC ACCAACGTAA CCTATCCCAT      6660

TACGGTCAAT CCGCCGTTTG TTCCCACGGA GAATCCGACG GGTTGTTACT CGCTCACATT      6720

TAATGTTGAT GAAAGCTGGC TACAGGAAGG CCAGACGCGA ATTATTTTTG ATGGCGTTCC      6780

TATTGGTTAA AAAATGAGCT GATTTAACAA AAATTTAACG CGAATTTTAA CAAAATATTA      6840

ACGTTTACAA TTTAAATATT TGCTTATACA ATCTTCCTGT TTTTGGGGCT TTTCTGATTA      6900

TCAACCGGGG TACATATGAT TGACATGCTA GTTTTACGAT TACCGTTCAT CGATTCTCTT      6960

GTTTGCTCCA GACTCTCAGG CAATGACCTG ATAGCCTTTG TAGATCTCTC AAAAATAGCT      7020

ACCCTCTCCG GCATTAATTT ATCAGCTAGA ACGGTTGAAT ATCATATTGA TGGTGATTTG      7080

ACTGTCTCCG GCCTTTCTCA CCCTTTTGAA TCTTTACCTA CACATTACTC AGGCATTGCA      7140

TTTAAAATAT ATGAGGGTTC TAAAAATTTT TATCCTTGCG TTGAAATAAA GGCTTCTCCC      7200

GCAAAAGTAT TACAGGGTCA TAATGTTTTT GGTACAACCG ATTTAGCTTT ATGCTCTGAG      7260

GCTTTATTGC TTAATTTTGC TAATTCTTTG CCTTGCCTGT ATGATTTATT GGATGTT        7317
```

(2) INFORMATION FOR SEQ ID NO:3:

(i) SEQUENCE CHARACTERISTICS:
        (A) LENGTH: 7729 base pairs
        (B) TYPE: nucleic acid
        (C) STRANDEDNESS: both
        (D) TOPOLOGY: circular (xi) SEQUENCE DESCRIPTION: SEQ ID NO:3:

```
AATGCTACTA CTATTAGTAG AATTGATGCC ACCTTTTCAG CTCGCGCCCC AAATGAAAAT      60

ATAGCTAAAC AGGTTATTGA CCATTTGCGA AATGTATCTA ATGGTCAAAC TAAATCTACT     120

CGTTCGCAGA ATTGGGAATC AACTGTTACA TGGAATGAAA CTTCCAGACA CCGTACTTTA     180

GTTGCATATT TAAAACATGT TGAGCTACAG CACCAGATTC AGCAATTAAG CTCTAAGCCA     240

TCTGCAAAAA TGACCTCTTA TCAAAAGGAG CAATTAAAGG TACTCTCTAA TCCTGACCTG     300

TTGGAGTTTG CTTCCGGTCT GGTTCGCTTT GAAGCTCGAA TTAAAACGCG ATATTTGAAG     360

TCTTTCGGGC TTCCTCTTAA TCTTTTTGAT GCAATCCGCT TTGCTTCTGA CTATAATAGT     420

CAGGGTAAAG ACCTGATTTT TGATTTATGG TCATTCTCGT TTTCTGAACT GTTTAAAGCA     480

TTTGAGGGGG ATTCAATGAA TATTTATGAC GATTCCGCAG TATTGGACGC TATCCAGTCT     540

AAACATTTTA CTATTACCCC CTCTGGCAAA ACTTCTTTTG CAAAAGCCTC TCGCTATTTT     600

GGTTTTTATC GTCGTCTGGT AAACGAGGGT TATGATAGTG TTGCTCTTAC TATGCCTCGT     660

AATTCCTTTT GGCGTTATGT ATCTGCATTA GTTGAATGTG GTATTCCTAA ATCTCAACTG     720

ATGAATCTTT CTACCTGTAA TAATGTTGTT CCGTTAGTTC GTTTTATTAA CGTAGATTTT     780

TCTTCCCAAC GTCCTGACTG GTATAATGAG CCAGTTCTTA AAATCGCATA AGGTAATTCA     840

CAATGATTAA AGTTGAAATT AAACCATCTC AAGCCCAATT TACTACTCGT TCTGGTGTTT     900

CTCGTCAGGG CAAGCCTTAT TCACTGAATG AGCAGCTTTG TTACGTTGAT TTGGGTAATG     960

AATATCCGGT TCTTGTCAAG ATTACTCTTG ATGAAGGTCA GCCAGCCTAT GCGCCTGGTC    1020

TGTACACCGT TCATCTGTCC TCTTTCAAAG TTGGTCAGTT CGGTTCCCTT ATGATTGACC    1080

GTCTGCGCCT CGTTCCGGCT AAGTAACATG GAGCAGGTCG CGGATTTCGA CACAATTTAT    1140

CAGGCGATGA TACAAATCTC CGTTGTACTT TGTTTCGCGC TTGGTATAAT CGCTGGGGGT    1200

CAAAGATGAG TGTTTTAGTG TATTCTTTCG CCTCTTTCGT TTTAGGTTGG TGCCTTCGTA    1260

GTGGCATTAC GTATTTTACC CGTTTAATGG AAACTTCCTC ATGAAAAAGT CTTTAGTCCT    1320

CAAAGCCTCT GTAGCCGTTG CTACCCTCGT TCCGATGCTG TCTTTCGCTG CTGAGGGTGA    1380

CGATCCCGCA AAAGCGGCCT TTAACTCCCT GCAAGCCTCA GCGACCGAAT ATATCGGTTA    1440

TGCGTGGGCG ATGGTTGTTG TCATTGTCGG CGCAACTATC GGTATCAAGC TGTTTAAGAA    1500

ATTCACCTCG AAAGCAAGCT GATAAACCGA TACAATTAAA GGCTCCTTTT GGAGCCTTTT    1560

TTTTTGGAGA TTTTCAACGT GAAAAAATTA TTATTCGCAA TTCCTTTAGT TGTTCCTTTC    1620

TATTCTCACT CCGCTGAAAC TGTTGAAAGT TGTTTAGCAA AACCCCATAC AGAAAATTCA    1680

TTTACTAACG TCTGGAAAGA CGACAAAACT TTAGATCGTT ACGCTAACTA TGAGGGTTGT    1740

CTGTGGAATG CTACAGGCGT TGTAGTTTGT ACTGGTGACG AAACTCAGTG TTACGGTACA    1800

TGGGTTCCTA TTGGGCTTGC TATCCCTGAA AATGAGGGTG GTGGCTCTGA GGGTGGCGGT    1860

TCTGAGGGTG GCGGTTCTGA GGGTGGCGGT ACTAAACCTC CTGAGTACGG TGATACACCT    1920

ATTCCGGGCT ATACTTATAT CAACCCTCTC GACGGCACTT ATCCGCCTGG TACTGAGCAA    1980

AACCCCGCTA ATCCTAATCC TTCTCTTGAG GAGTCTCAGC CTCTTAATAC TTTCATGTTT    2040

CAGAATAATA GGTTCCGAAA TAGGCAGGGG GCATTAACTG TTTATACGGG CACTGTTACT    2100

CAAGGCACTG ACCCCGTTAA AACTTATTAC CAGTACACTC CTGTATCATC AAAAGCCATG    2160

TATGACGCTT ACTGGAACGG TAAATTCAGA GACTGCGCTT TCCATTCTGG CTTTAATGAA    2220

GATCCATTCG TTTGTGAATA TCAAGGCCAA TCGTCTGACC TGCCTCAACC TCCTGTCAAT    2280
```

```
GCTGGCGGCG GCTCTGGTGG TGGTTCTGGT GGCGGCTCTG AGGGTGGTGG CTCTGAGGGT      2340

GGCGGTTCTG AGGGTGGCGG CTCTGAGGGA GGCGGTTCCG GTGGTGGCTC TGGTTCCGGT      2400

GATTTTGATT ATGAAAAGAT GGCAAACGCT AATAAGGGGG CTATGACCGA AAATGCCGAT      2460

GAAAACGCGC TACAGTCTGA CGCTAAAGGC AAACTTGATT CTGTCGCTAC TGATTACGGT      2520

GCTGCTATCG ATGGTTTCAT TGGTGACGTT TCCGGCCTTG CTAATGGTAA TGGTGCTACT      2580

GGTGATTTTG CTGGCTCTAA TTCCCAAATG GCTCAAGTCG GTGACGGTGA TAATTCACCT      2640

TTAATGAATA ATTTCCGTCA ATATTTACCT TCCCTCCCTC AATCGGTTGA ATGTCGCCCT      2700

TTTGTCTTTA GCGCTGGTAA ACCATATGAA TTTTCTATTG ATTGTGACAA AATAAACTTA      2760

TTCCGTGGTG TCTTTGCGTT TCTTTTATAT GTTGCCACCT TTATGTATGT ATTTTCTACG      2820

TTTGCTAACA TACTGCGTAA TAAGGAGTCT TAATCATGCC AGTTCTTTTG GGTATTCCGT      2880

TATTATTGCG TTTCCTCGGT TTCCTTCTGG TAACTTTGTT CGGCTATCTG CTTACTTTTC      2940

TTAAAAGGG CTTCGGTAAG ATAGCTATTG CTATTTCATT GTTTCTTGCT CTTATTATTG      3000

GGCTTAACTC AATTCTTGTG GGTTATCTCT CTGATATTAG CGCTCAATTA CCCTCTGACT      3060

TTGTTCAGGG TGTTCAGTTA ATTCTCCCGT CTAATGCGCT TCCCTGTTTT TATGTTATTC      3120

TCTCTGTAAA GGCTGCTATT TTCATTTTTG ACGTTAAACA AAAAATCGTT TCTTATTTGG      3180

ATTGGGATAA ATAATATGGC TGTTTATTTT GTAACTGGCA AATTAGGCTC TGGAAAGACG      3240

CTCGTTAGCG TTGGTAAGAT TCAGGATAAA ATTGTAGCTG GGTGCAAAAT AGCAACTAAT      3300

CTTGATTTAA GGCTTCAAAA CCTCCCGCAA GTCGGGAGGT TCGCTAAAAC GCCTCGCGTT      3360

CTTAGAATAC CGGATAAGCC TTCTATATCT GATTTGCTTG CTATTGGGCG CGGTAATGAT      3420

TCCTACGATG AAAATAAAAA CGGCTTGCTT GTTCTCGATG AGTGCGGTAC TTGGTTTAAT      3480

ACCCGTTCTT GGAATGATAA GGAAAGACAG CCGATTATTG ATTGGTTTCT ACATGCTCGT      3540

AAATTAGGAT GGGATATTAT TTTTCTTGTT CAGGACTTAT CTATTGTTGA TAAACAGGCG      3600

CGTTCTGCAT TAGCTGAACA TGTTGTTTAT TGTCGTCGTC TGGACAGAAT TACTTTACCT      3660

TTTGTCGGTA CTTTATATTC TCTTATTACT GGCTCGAAAA TGCCTCTGCC TAAATTACAT      3720

GTTGGCGTTG TTAAATATGG CGATTCTCAA TTAAGCCCTA CTGTTGAGCG TTGGCTTTAT      3780

ACTGGTAAGA ATTTGTATAA CGCATATGAT ACTAAACAGG CTTTTTCTAG TAATTATGAT      3840

TCCGGTGTTT ATTCTTATTT AACGCCTTAT TTATCACACG GTCGGTATTT CAAACCATTA      3900

AATTTAGGTC AGAAGATGAA GCTTACTAAA ATATATTTGA AAAGTTTTC ACGCGTTCTT      3960

TGTCTTGCGA TTGGATTTGC ATCAGCATTT ACATATAGTT ATATAACCCA ACCTAAGCCG      4020

GAGGTTAAAA AGGTAGTCTC TCAGACCTAT GATTTTGATA AATTCACTAT TGACTCTTCT      4080

CAGCGTCTTA ATCTAAGCTA TCGCTATGTT TTCAAGGATT CTAAGGGAAA ATTAATTAAT      4140

AGCGACGATT TACAGAAGCA AGGTTATTCA CTCACATATA TTGATTTATG TACTGTTTCC      4200

ATTAAAAAAG GTAATTCAAA TGAAATTGTT AAATGTAATT AATTTTGTTT TCTTGATGTT      4260

TGTTTCATCA TCTTCTTTTG CTCAGGTAAT TGAAATGAAT AATTCGCCTC TGCGCGATTT      4320

TGTAACTTGG TATTCAAAGC AATCAGGCGA ATCCGTTATT GTTTCTCCCG ATGTAAAAGG      4380

TACTGTTACT GTATATTCAT CTGACGTTAA ACCTGAAAAT CTACGCAATT TCTTTATTTC      4440

TGTTTTACGT GCTAATAATT TTGATATGGT TGGTTCAATT CCTTCCATAA TTCAGAAGTA      4500

TAATCCAAAC AATCAGGATT ATATTGATGA ATTGCCATCA TCTGATAATC AGGAATATGA      4560

TGATAATTCC GCTCCTTCTG GTGGTTTCTT TGTTCCGCAA AATGATAATG TTACTCAAAC      4620

TTTTAAAATT AATAACGTTC GGGCAAAGGA TTTAATACGA GTTGTCGAAT TGTTTGTAAA      4680
```

```
GTCTAATACT TCTAAATCCT CAAATGTATT ATCTATTGAC GGCTCTAATC TATTAGTTGT    4740

TAGTGCACCT AAAGATATTT TAGATAACCT TCCTCAATTC CTTTCTACTG TTGATTTGCC    4800

AACTGACCAG ATATTGATTG AGGGTTTGAT ATTTGAGGTT CAGCAAGGTG ATGCTTTAGA    4860

TTTTTCATTT GCTGCTGGCT CTCAGCGTGG CACTGTTGCA GGCGGTGTTA ATACTGACCG    4920

CCTCACCTCT GTTTTATCTT CTGCTGGTGG TTCGTTCGGT ATTTTTAATG GCGATGTTTT    4980

AGGGCTATCA GTTCGCGCAT TAAAGACTAA TAGCCATTCA AAAATATTGT CTGTGCCACG    5040

TATTCTTACG CTTTCAGGTC AGAAGGGTTC TATCTCTGTT GGCCAGAATG TCCCTTTTAT    5100

TACTGGTCGT GTGACTGGTG AATCTGCCAA TGTAAATAAT CCATTTCAGA CGATTGAGCG    5160

TCAAAATGTA GGTATTTCCA TGAGCGTTTT TCCTGTTGCA ATGGCTGGCG GTAATATTGT    5220

TCTGGATATT ACCAGCAAGG CCGATAGTTT GAGTTCTTCT ACTCAGGCAA GTGATGTTAT    5280

TACTAATCAA AGAAGTATTG CTACAACGGT TAATTTGCGT GATGGACAGA CTCTTTTACT    5340

CGGTGGCCTC ACTGATTATA AAAACACTTC TCAAGATTCT GGCGTACCGT TCCTGTCTAA    5400

AATCCCTTTA ATCGGCCTCC TGTTTAGCTC CCGCTCTGAT TCCAACGAGG AAAGCACGTT    5460

ATACGTGCTC GTCAAAGCAA CCATAGTACG CGCCCTGTAG CGGCGCATTA AGCGCGGCGG    5520

GTGTGGTGGT TACGCGCAGC GTGACCGCTA CACTTGCCAG CGCCCTAGCG CCCGCTCCTT    5580

TCGCTTTCTT CCCTTCCTTT CTCGCCACGT TCGCCGGCTT TCCCCGTCAA GCTCTAAATC    5640

GGGGGCTCCC TTTAGGGTTC CGATTTAGTG CTTTACGGCA CCTCGACCCC AAAAAACTTG    5700

ATTTGGGTGA TGGTTCACGT AGTGGGCCAT CGCCCTGATA GACGGTTTTT CGCCCTTTGA    5760

CGTTGGAGTC CACGTTCTTT AATAGTGGAC TCTTGTTCCA AACTGGAACA ACACTCAACC    5820

CTATCTCGGG CTATTCTTTT GATTTATAAG GGATTTTGCC GATTTCGGAA CCACCATCAA    5880

ACAGGATTTT CGCCTGCTGG GGCAAACCAG CGTGGACCGC TTGCTGCAAC TCTCTCAGGG    5940

CCAGGCGGTG AAGGGCAATC AGCTGTTGCC CGTCTCGCTG GTGAAAAGAA AAACCACCCT    6000

GGCGCCCAAT ACGCAAACCG CCTCTCCCCG CGCGTTGGCC GATTCATTAA TGCAGCTGGC    6060

ACGACAGGTT TCCCGACTGG AAAGCGGGCA GTGAGCGCAA CGCAATTAAT GTGAGTTAGC    6120

TCACTCATTA GGCACCCCAG GCTTTACACT TTATGCTTCC GGCTCGTATG TTGTGTGGAA    6180

TTGTGAGCGG ATAACAATTT CACACGCGTC ACTTGGCACT GGCCGTCGTT TTACAACGTC    6240

GTGACTGGGA AAACCCTGGC GTTACCCAAG CTTTGTACAT GGAGAAAATA AAGTGAAACA    6300

AAGCACTATT GCACTGGCAC TCTTACCGTT ACTGTTTACC CCTGTGGCAA AGCCCAGGT    6360

CCAGCTGCTC GAGTCGGTCT TCCCCCTGGC ACCCTCCTCC AAGAGCACCT CTGGGGCAC    6420

AGCGGCCCTG GGCTGCCTGG TCAAGACTAA TTCCCCGAAC CGGTGACGGT GTCGTGGAAC    6480

TCAGGCGCCC TGACCAGCGG CGTGCACACC TTCCCGGCTG TCCTACAGTC CTCAGGACTC    6540

TACTCCCTCA GCAGCGTGGT GACCGTGCCC TCCAGCAGCT TGGGCACCCA GACCTACATC    6600

TGCAACGTGA ATCACAAGCC CAGCAACACC AAGGTGGACA AGAAAGCAGA GCCCAAATCT    6660

TGTACTAGTG GATCCTACCC GTACGACGTT CCGGACTACG CTTCTTAGGC TGAAGGCGAT    6720

GACCCTGCTA AGGCTGCATT CAATAGTTTA CAGGCAAGTG CTACTGAGTA CATTGGCTAC    6780

GCTTGGGCTA TGGTAGTAGT TATAGTTGGT GCTACCATAG GGATTAAATT ATTCAAAAAG    6840

TTTACGAGCA AGGCTTCTTA AGCAATAGCG AAGAGGCCCG CACCGATCGC CCTTCCCAAC    6900

AGTTGCGCAG CCTGAATGGC GAATGGCGCT TTGCCTGGTT TCCGGCACCA GAAGCGGTGC    6960

CGGAAAGCTG GCTGGAGTGC GATCTTCCTG AGGCCGATAC GGTCGTCGTC CCCTCAAACT    7020
```

-continued

| | |
|---|---|
| GGCAGATGCA CGGTTACGAT GCGCCCATCT ACACCAACGT AACCTATCCC ATTACGGTCA | 7080 |
| ATCCGCCGTT TGTTCCCACG GAGAATCCGA CGGGTTGTTA CTCGCTCACA TTTAATGTTG | 7140 |
| ATGAAAGCTG GCTACAGGAA GGCCAGACGC GAATTATTTT TGATGGCGTT CCTATTGGTT | 7200 |
| AAAAAATGAG CTGATTTAAC AAAAATTTAA CGCGAATTTT AACAAAATAT AACGTTTAC | 7260 |
| AATTTAAATA TTTGCTTATA CAATCTTCCT GTTTTTGGGG CTTTTCTGAT TATCAACCGG | 7320 |
| GGTACATATG ATTGACATGC TAGTTTTACG ATTACCGTTC ATCGATTCTC TTGTTTGCTC | 7380 |
| CAGACTCTCA GGCAATGACC TGATAGCCTT TGTAGATCTC TCAAAAATAG CTACCCTCTC | 7440 |
| CGGCATTAAT TTATCAGCTA GAACGGTTGA ATATCATATT GATGGTGATT TGACTGTCTC | 7500 |
| CGGCCTTTCT CACCCTTTTG AATCTTTACC TACACATTAC TCAGGCATTG CATTTAAAAT | 7560 |
| ATATGAGGGT TCTAAAAATT TTTATCCTTG CGTTGAAATA AAGGCTTCTC CCGCAAAAGT | 7620 |
| ATTACAGGGT CATAATGTTT TTGGTACAAC CGATTTAGCT TTATGCTCTG AGGCTTTATT | 7680 |
| GCTTAATTTT GCTAATTCTT TGCCTTGCCT GTATGATTTA TTGGACGTT | 7729 |

(2) INFORMATION FOR SEQ ID NO:4:

(i) SEQUENCE CHARACTERISTICS:
        (A) LENGTH: 7557 base pairs
        (B) TYPE: nucleic acid
        (C) STRANDEDNESS: both
        (D) TOPOLOGY: circular (xi) SEQUENCE DESCRIPTION: SEQ ID NO:4:

| | |
|---|---|
| AATGCTACTA CTATTAGTAG AATTGATGCC ACCTTTTCAG CTCGCGCCCC AAATGAAAAT | 60 |
| ATAGCTAAAC AGGTTATTGA CCATTTGCGA AATGTATCTA ATGGTCAAAC TAAATCTACT | 120 |
| CGTTCGCAGA ATTGGGAATC AACTGTTACA TGGAATGAAA CTTCCAGACA CCGTACTTTA | 180 |
| GTTGCATATT TAAAACATGT TGAGCTACAG CACCAGATTC AGCAATTAAG CTCTAAGCCA | 240 |
| TCCGCAAAAA TGACCTCTTA TCAAAAGGAG CAATTAAAGG TACTCTCTAA TCCTGACCTG | 300 |
| TTGGAGTTTG CTTCCGGTCT GGTTCGCTTT GAAGCTCGAA TTAAAACGCG ATATTTGAAG | 360 |
| TCTTTCGGGC TTCCTCTTAA TCTTTTTGAT GCAATCCGCT TTGCTTCTGA CTATAATAGT | 420 |
| CAGGGTAAAG ACCTGATTTT TGATTTATGG TCATTCTCGT TTTCTGAACT GTTTAAAGCA | 480 |
| TTTGAGGGGG ATTCAATGAA TATTTATGAC GATTCCGCAG TATTGGACGC TATCCAGTCT | 540 |
| AAACATTTTA CTATTACCCC CTCTGGCAAA ACTTCTTTTG CAAAAGCCTC TCGCTATTTT | 600 |
| GGTTTTTATC GTCGTCTGGT AAACGAGGGT TATGATAGTG TTGCTCTTAC TATGCCTCGT | 660 |
| AATTCCTTTT GGCGTTATGT ATCTGCATTA GTTGAATGTG GTATTCCTAA ATCTCAACTG | 720 |
| ATGAATCTTT CTACCTGTAA TAATGTTGTT CCGTTAGTTC GTTTTATTAA CGTAGATTTT | 780 |
| TCTTCCCAAC GTCCTGACTG GTATAATGAG CCAGTTCTTA AAATCGCATA AGGTAATTCA | 840 |
| CAATGATTAA AGTTGAAATT AAACCATCTC AAGCCCAATT TACTACTCGT TCTGGTGTTT | 900 |
| CTCGTCAGGG CAAGCCTTAT TCACTGAATG AGCAGCTTTG TTACGTTGAT TTGGGTAATG | 960 |
| AATATCCGGT TCTTGTCAAG ATTACTCTTG ATGAAGGTCA GCCAGCCTAT GCGCCTGGTC | 1020 |
| TGTACACCGT TCATCTGTCC TCTTTCAAAG TTGGTCAGTT CGGTTCCCTT ATGATTGACC | 1080 |
| GTCTGCGCCT CGTTCCGGCT AAGTAACATG GAGCAGGTCG CGGATTTCGA CACAATTTAT | 1140 |
| CAGGCGATGA TACAAATCTC CGTTGTACTT TGTTTCGCGC TTGGTATAAT CGCTGGGGGT | 1200 |
| CAAAGATGAG TGTTTTAGTG TATTCTTTCG CCTCTTTCGT TTTAGGTTGG TGCCTTCGTA | 1260 |
| GTGGCATTAC GTATTTTACC CGTTTAATGG AAACTTCCTC ATGAAAAAGT CTTTAGTCCT | 1320 |

-continued

| | | | | | |
|---|---|---|---|---|---|
| CAAAGCCTCT | GTAGCCGTTG | CTACCCTCGT | TCCGATGCTG | TCTTTCGCTG | CTGAGGGTGA | 1380 |
| CGATCCCGCA | AAAGCGGCCT | TTAACTCCCT | GCAAGCCTCA | GCGACCGAAT | ATATCGGTTA | 1440 |
| TGCGTGGGCG | ATGGTTGTTG | TCATTGTCGG | CGCAACTATC | GGTATCAAGC | TGTTTAAGAA | 1500 |
| ATTCACCTCG | AAAGCAAGCT | GATAAACCGA | TACAATTAAA | GGCTCCTTTT | GGAGCCTTTT | 1560 |
| TTTTTGGAGA | TTTTCAACGT | GAAAAAATTA | TTATTCGCAA | TTCCTTTAGT | TGTTCCTTTC | 1620 |
| TATTCTCACT | CCGCTGAAAC | TGTTGAAAGT | TGTTTAGCAA | AACCCCATAC | AGAAAATTCA | 1680 |
| TTTACTAACG | TCTGGAAAGA | CGACAAAACT | TTAGATCGTT | ACGCTAACTA | TGAGGGTTGT | 1740 |
| CTGTGGAATG | CTACAGGCGT | TGTAGTTTGT | ACTGGTGACG | AAACTCAGTG | TTACGGTACA | 1800 |
| TGGGTTCCTA | TTGGGCTTGC | TATCCCTGAA | AATGAGGGTG | GTGGCTCTGA | GGGTGGCGGT | 1860 |
| TCTGAGGGTG | GCGGTTCTGA | GGGTGGCGGT | ACTAAACCTC | CTGAGTACGG | TGATACACCT | 1920 |
| ATTCCGGGCT | ATACTTATAT | CAACCCTCTC | GACGGCACTT | ATCCGCCTGG | TACTGAGCAA | 1980 |
| AACCCCGCTA | ATCCTAATCC | TTCTCTTGAG | GAGTCTCAGC | CTCTTAATAC | TTTCATGTTT | 2040 |
| CAGAATAATA | GGTTCCGAAA | TAGGCAGGGG | GCATTAACTG | TTTATACGGG | CACTGTTACT | 2100 |
| CAAGGCACTG | ACCCCGTTAA | AACTTATTAC | CAGTACACTC | CTGTATCATC | AAAAGCCATG | 2160 |
| TATGACGCTT | ACTGGAACGG | TAAATTCAGA | GACTGCGCTT | TCCATTCTGG | CTTTAATGAA | 2220 |
| GATCCATTCG | TTTGTGAATA | TCAAGGCCAA | TCGTCTGACC | TGCCTCAACC | TCCTGTCAAT | 2280 |
| GCTGGCGGCG | GCTCTGGTGG | TGGTTCTGGT | GGCGGCTCTG | AGGGTGGTGG | CTCTGAGGGT | 2340 |
| GGCGGTTCTG | AGGGTGGCGG | CTCTGAGGGA | GGCGGTTCCG | GTGGTGGCTC | TGGTTCCGGT | 2400 |
| GATTTTGATT | ATGAAAAGAT | GGCAAACGCT | AATAAGGGGG | CTATGACCGA | AAATGCCGAT | 2460 |
| GAAAACGCGC | TACAGTCTGA | CGCTAAAGGC | AAACTTGATT | CTGTCGCTAC | TGATTACGGT | 2520 |
| GCTGCTATCG | ATGGTTTCAT | TGGTGACGTT | TCCGGCCTTG | CTAATGGTAA | TGGTGCTACT | 2580 |
| GGTGATTTTG | CTGGCTCTAA | TTCCCAAATG | GCTCAAGTCG | GTGACGGTGA | TAATTCACCT | 2640 |
| TTAATGAATA | ATTTCCGTCA | ATATTTACCT | TCCCTCCCTC | AATCGGTTGA | ATGTCGCCCT | 2700 |
| TTTGTCTTTA | GCGCTGGTAA | ACCATATGAA | TTTTCTATTG | ATTGTGACAA | AATAAACTTA | 2760 |
| TTCCGTGGTG | TCTTTGCGTT | TCTTTTATAT | GTTGCCACCT | TTATGTATGT | ATTTTCTACG | 2820 |
| TTTGCTAACA | TACTGCGTAA | TAAGGAGTCT | TAATCATGCC | AGTTCTTTTG | GGTATTCCGT | 2880 |
| TATTATTGCG | TTTCCTCGGT | TTCCTTCTGG | TAACTTTGTT | CGGCTATCTG | CTTACTTTTC | 2940 |
| TTAAAAAGGG | CTTCGGTAAG | ATAGCTATTG | CCTGTTTCTT | GCTCTTATTA | TTGGGCTTAA | 3000 |
| CTCAATTCTT | GTGGGTTATC | TCTCTGATAT | TAGCGCTCAA | TTACCCTCTG | ACTTTGTTCA | 3060 |
| GGGTGTTCAG | TTAATTCTCC | CGTCTAATGC | GCTTCCCTGT | TTTTATGTTA | TTCTCTCTGT | 3120 |
| AAAGGCTGCT | ATTTTCATTT | TTGACGTTAA | ACAAAAAATC | GTTTCTTATT | TGGATTGGGA | 3180 |
| TAAATAATAT | GGCTGTTTAT | TTTGTAACTG | GCAAATTAGG | CTCTGGAAAG | ACGCTCGTTA | 3240 |
| GCGTTGGTAA | GATTCAGGAT | AAAATTGTAG | CTGGGTGCAA | AATAGCAACT | AATCTTGATT | 3300 |
| TAAGGCTTCA | AAACCTCCCG | CAAGTCGGGA | GGTTCGCTAA | AACGCCTCGC | GTTCTTAGAA | 3360 |
| TACCGGATAA | GCCTTCTATA | TCTGATTTGC | TTGCTATTGG | GCGCGGTAAT | GATTCCTACG | 3420 |
| ATGAAAATAA | AAACGGCTTG | CTTGTTCTCG | ATGAGTGCGG | TACTTGGTTT | AATACCCGTT | 3480 |
| CTTGGAATGA | TAAGGAAAGA | CAGCCGATTA | TTGATTGGTT | TCTACATGCT | CGTAAATTAG | 3540 |
| GATGGGATAT | TATTTTTCTT | GTTCAGGACT | TATCTATTGT | TGATAAACAG | GCGCGTTCTG | 3600 |
| CATTAGCTGA | ACATGTTGTT | TATTGTCGTC | GTCTGGACAG | AATTACTTTA | CCTTTTGTCG | 3660 |
| GTACTTTATA | TTCTCTTATT | ACTGGCTCGA | AAATGCCTCT | GCCTAAATTA | CATGTTGGCG | 3720 |

```
TTGTTAAATA TGGCGATTCT CAATTAAGCC CTACTGTTGA GCGTTGGCTT TATACTGGTA    3780

AGAATTTGTA TAACGCATAT GATACTAAAC AGGCTTTTTC TAGTAATTAT GATTCCGGTG    3840

TTTATTCTTA TTTAACGCCT TATTTATCAC ACGGTCGGTA TTTCAAACCA TTAAATTTAG    3900

GTCAGAAGAT GAAGCTTACT AAAATATATT TGAAAAAGTT TTCACGCGTT CTTTGTCTTG    3960

CGATTGGATT TGCATCAGCA TTTACATATA GTTATATAAC CCAACCTAAG CCGGAGGTTA    4020

AAAAGGTAGT CTCTCAGACC TATGATTTTG ATAAATTCAC TATTGACTCT TCTCAGCGTC    4080

TTAATCTAAG CTATCGCTAT GTTTTCAAGG ATTCTAAGGG AAAATTAATT AATAGCGACG    4140

ATTTACAGAA GCAAGGTTAT TCACTCACAT ATATTGATTT ATGTACTGTT TCCATTAAAA    4200

AAGGTAATTC AAATGAAATT GTTAAATGTA ATTAATTTTG TTTTCTTGAT GTTTGTTTCA    4260

TCATCTTCTT TTGCTCAGGT AATTGAAATG AATAATTCGC CTCTGCGCGA TTTTGTAACT    4320

TGGTATTCAA AGCAATCAGG CGAATCCGTT ATTGTTTCTC CCGATGTAAA AGGTACTGTT    4380

ACTGTATATT CATCTGACGT TAAACCTGAA AATCTACGCA ATTTCTTTAT TTCTGTTTTA    4440

CGTGCTAATA ATTTTGATAT GGTTGGTTCA ATTCCTTCCA TAATTCAGAA GTATAATCCA    4500

AACAATCAGG ATTATATTGA TGAATTGCCA TCATCTGATA ATCAGGAATA TGATGATAAT    4560

TCCGCTCCTT CTGGTGGTTT CTTTGTTCCG CAAAATGATA ATGTTACTCA AACTTTTAAA    4620

ATTAATAACG TTCGGGCAAA GGATTTAATA CGAGTTGTCG AATTGTTTGT AAAGTCTAAT    4680

ACTTCTAAAT CCTCAAATGT ATTATCTATT GACGGCTCTA ATCTATTAGT TGTTAGTGCA    4740

CCTAAAGATA TTTTAGATAA CCTTCCTCAA TTCCTTTCTA CTGTTGATTT GCCAACTGAC    4800

CAGATATTGA TTGAGGGTTT GATATTTGAG GTTCAGCAAG GTGATGCTTT AGATTTTTCA    4860

TTTGCTGCTG GCTCTCAGCG TGGCACTGTT GCAGGCGGTG TTAATACTGA CCGCCTCACC    4920

TCTGTTTTAT CTTCTGCTGG TGGTTCGTTC GGTATTTTTA ATGGCGATGT TTTAGGGCTA    4980

TCAGTTCGCG CATTAAAGAC TAATAGCCAT TCAAAAATAT TGTCTGTGCC ACGTATTCTT    5040

ACGCTTTCAG GTCAGAAGGG TTCTATCTCT GTTGGCCAGA ATGTCCCTTT TATTACTGGT    5100

CGTGTGACTG GTGAATCTGC CAATGTAAAT AATCCATTTC AGACGATTGA GCGTCAAAAT    5160

GTAGGTATTT CCATGAGCGT TTTTCCTGTT GCAATGGCTG GCGGTAATAT TGTTCTGGAT    5220

ATTACCAGCA AGGCCGATAG TTTGAGTTCT TCTACTCAGG CAAGTGATGT TATTACTAAT    5280

CAAAGAAGTA TTGCTACAAC GGTTAATTTG CGTGATGGAC AGACTCTTTT ACTCGGTGGC    5340

CTCACTGATT ATAAAAACAC TTCTCAAGAT TCTGGCGTAC CGTTCCTGTC TAAAATCCCT    5400

TTAATCGGCC TCCTGTTTAG CTCCCGCTCT GATTCCAACG AGGAAAGCAC GTTATACGTG    5460

CTCGTCAAAG CAACCATAGT ACGCGCCCTG TAGCGGCGCA TTAAGCGCGG CGGGTGTGGT    5520

GGTTACGCGC AGCGTGACCG CTACACTTGC CAGCGCCCTA GCGCCCGCTC CTTTCGCTTT    5580

CTTCCCTTCC TTTCTCGCCA CGTTCGCCGG CTTTCCCCGT CAAGCTCTAA ATCGGGGGCT    5640

CCCTTTAGGG TTCCGATTTA GTGCTTTACG GCACCTCGAC CCCAAAAAAC TTGATTTGGG    5700

TGATGGTTCA CGTAGTGGGC CATCGCCCTG ATAGACGGTT TTTCGCCCTT TGACGTTGGA    5760

GTCCACGTTC TTTAATAGTG GACTCTTGTT CCAAACTGGA ACAACACTCA ACCCTATCTC    5820

GGGCTATTCT TTTGATTTAT AAGGGATTTT GCCGATTTCG GAACCACCAT CAAACAGGAT    5880

TTTCGCCTGC TGGGGCAAAC CAGCGTGGAC CGCTTGCTGC AACTCTCTCA GGGCCAGGCG    5940

GTGAAGGGCA ATCAGCTGTT GCCCGTCTCG CTGGTGAAAA GAAAAACCAC CCTGGCGCCC    6000

AATACGCAAA CCGCCTCTCC CCGCGCGTTG GCCGATTCAT TAATGCAGCT GGCACGACAG    6060
```

-continued

```
GTTTCCCGAC TGGAAAGCGG GCAGTGAGCG CAACGCAATT AATGTGAGTT AGCTCACTCA      6120

TTAGGCACCC CAGGCTTTAC ACTTTATGCT TCCGGCTCGT ATGTTGTGTG GAATTGTGAG      6180

CGGATAACAA TTTCACACGC CAAGGAGACA GTCATAATGA AATACCTATT GCCTACGGCA      6240

GCCGCTGGAT TGTTATTACT CGCTGCCCAA CCAGCCATGG CCGAGCTCTT CCCGCCATCT      6300

GATGAGCAGT TGAAATCTGG AACTGCCTCT GTTGTGTGCC TGCTGAATAA CTTCTATCCC      6360

AGAGAGGCCA AGTACAGTG GAAGGTGGAT AACGCCCTCC AATCGGGTAA CTCCCAGGAG      6420

AGTGTCACAG AGCAGGACAG CAAGGACAGC ACCTACAGCC TCAGCAGCAC CCTGACGCTG      6480

AGCAAAGCAG ACTACGAGAA ACACAAAGTC TACGCCTGCG AAGTCACCCA TCAGGGCCTG      6540

AGCTCGCCCG TCACAAAGAG CTTCAACAGG GGAGAGTGTT CTAGAACGCG TCACTTGGCA      6600

CTGGCCGTCG TTTTACAACG TCGTGACTGG GAAAACCCTG GCGTTACCCA AGCTTAATCG      6660

CCTTGCAGAA TTCCCTTTCG CCAGCTGGCG TAATAGCGAA GAGGCCCGCA CCGATCGCCC      6720

TTCCCAACAG TTGCGCAGCC TGAATGGCGA ATGGCGCTTT GCCTGGTTTC CGGCACCAGA      6780

AGCGGTGCCG GAAAGCTGGC TGGAGTGCGA TCTTCCTGAG GCCGATACGG TCGTCGTCCC      6840

CTCAAACTGG CAGATGCACG GTTACGATGC GCCCATCTAC ACCAACGTAA CCTATCCCAT      6900

TACGGTCAAT CCGCCGTTTG TTCCCACGGA GAATCCGACG GGTTGTTACT CGCTCACATT      6960

TAATGTTGAT GAAAGCTGGC TACAGGAAGG CCAGACGCGA ATTATTTTTG ATGGCGTTCC      7020

TATTGGTTAA AAAATGAGCT GATTTAACAA AAATTTAACG CGAATTTTAA CAAAATATTA      7080

ACGTTTACAA TTTAAATATT TGCTTATACA ATCTTCCTGT TTTTGGGGCT TTTCTGATTA      7140

TCAACCGGGG TACATATGAT TGACATGCTA GTTTTACGAT TACCGTTCAT CGATTCTCTT      7200

GTTTGCTCCA GACTCTCAGG CAATGACCTG ATAGCCTTTG TAGATCTCTC AAAAATAGCT      7260

ACCCTCTCCG GCATTAATTT ATCAGCTAGA ACGGTTGAAT ATCATATTGA TGGTGATTTG      7320

ACTGTCTCCG GCCTTTCTCA CCCTTTTGAA TCTTTACCTA CACATTACTC AGGCATTGCA      7380

TTTAAAATAT ATGAGGGTTC TAAAAATTTT TATCCTTGCG TTGAAATAAA GGCTTCTCCC      7440

GCAAAAGTAT TACAGGGTCA TAATGTTTTT GGTACAACCG ATTTAGCTTT ATGCTCTGAG      7500

GCTTTATTGC TTAATTTTGC TAATTCTTTG CCTTGCCTGT ATGATTTATT GGATGTT       7557
```

(2) INFORMATION FOR SEQ ID NO:5:

(i) SEQUENCE CHARACTERISTICS:
        (A) LENGTH: 8118 base pairs
        (B) TYPE: nucleic acid
        (C) STRANDEDNESS: both
        (D) TOPOLOGY: circular (xi) SEQUENCE DESCRIPTION: SEQ ID NO:5:

```
AATGCTACTA CTATTAGTAG AATTGATGCC ACCTTTTCAG CTCGCGCCCC AAATGAAAAT        60

ATAGCTAAAC AGGTTATTGA CCATTTGCGA AATGTATCTA ATGGTCAAAC TAAATCTACT       120

CGTTCGCAGA ATTGGGAATC AACTGTTACA TGGAATGAAA CTTCCAGACA CCGTACTTTA       180

GTTGCATATT TAAAACATGT TGAGCTACAG CACCAGATTC AGCAATTAAG CTCTAAGCCA       240

TCTGCAAAAA TGACCTCTTA TCAAAAGGAG CAATTAAAGG TACTCTCTAA TCCTGACCTG       300

TTGGAGTTTG CTTCCGGTCT GGTTCGCTTT GAAGCTCGAA TTAAAACGCG ATATTTGAAG       360

TCTTTCGGGC TTCCTCTTAA TCTTTTTGAT GCAATCCGCT TTGCTTCTGA CTATAATAGT       420

CAGGGTAAAG ACCTGATTTT TGATTTATGG TCATTCTCGT TTTCTGAACT GTTTAAAGCA       480

TTTGAGGGGG ATTCAATGAA TATTTATGAC GATTCCGCAG TATTGGACGC TATCCAGTCT       540
```

-continued

```
AAACATTTTA CTATTACCCC CTCTGGCAAA ACTTCTTTTG CAAAAGCCTC TCGCTATTTT    600

GGTTTTTATC GTCGTCTGGT AAACGAGGGT TATGATAGTG TTGCTCTTAC TATGCCTCGT    660

AATTCCTTTT GGCGTTATGT ATCTGCATTA GTTGAATGTG GTATTCCTAA ATCTCAACTG    720

ATGAATCTTT CTACCTGTAA TAATGTTGTT CCGTTAGTTC GTTTTATTAA CGTAGATTTT    780

TCTTCCCAAC GTCCTGACTG GTATAATGAG CCAGTTCTTA AAATCGCATA AGGTAATTCA    840

CAATGATTAA AGTTGAAATT AAACCATCTC AAGCCCAATT TACTACTCGT TCTGGTGTTT    900

CTCGTCAGGG CAAGCCTTAT TCACTGAATG AGCAGCTTTG TTACGTTGAT TTGGGTAATG    960

AATATCCGGT TCTTGTCAAG ATTACTCTTG ATGAAGGTCA GCCAGCCTAT GCGCCTGGTC   1020

TGTACACCGT TCATCTGTCC TCTTTCAAAG TTGGTCAGTT CGGTTCCCTT ATGATTGACC   1080

GTCTGCGCCT CGTTCCGGCT AAGTAACATG GAGCAGGTCG CGGATTTCGA CACAATTTAT   1140

CAGGCGATGA TACAAATCTC CGTTGTACTT TGTTTCGCGC TTGGTATAAT CGCTGGGGGT   1200

CAAAGATGAG TGTTTTAGTG TATTCTTTCG CCTCTTTCGT TTTAGGTTGG TGCCTTCGTA   1260

GTGGCATTAC GTATTTTACC CGTTTAATGG AAACTTCCTC ATGAAAAAGT CTTTAGTCCT   1320

CAAAGCCTCT GTAGCCGTTG CTACCCTCGT TCCGATGCTG TCTTTCGCTG CTGAGGGTGA   1380

CGATCCCGCA AAAGCGGCCT TTAACTCCCT GCAAGCCTCA GCGACCGAAT ATATCGGTTA   1440

TGCGTGGGCG ATGGTTGTTG TCATTGTCGG CGCAACTATC GGTATCAAGC TGTTTAAGAA   1500

ATTCACCTCG AAAGCAAGCT GATAAACCGA TACAATTAAA GGCTCCTTTT GGAGCCTTTT   1560

TTTTTGGAGA TTTTCAACGT GAAAAAATTA TTATTCGCAA TTCCTTTAGT TGTTCCTTTC   1620

TATTCTCACT CCGCTGAAAC TGTTGAAAGT TGTTTAGCAA ACCCCATAC AGAAAATTCA   1680

TTTACTAACG TCTGGAAAGA CGACAAAACT TTAGATCGTT ACGCTAACTA TGAGGGTTGT   1740

CTGTGGAATG CTACAGGCGT TGTAGTTTGT ACTGGTGACG AAACTCAGTG TTACGGTACA   1800

TGGGTTCCTA TTGGGCTTGC TATCCCTGAA AATGAGGGTG GTGGCTCTGA GGGTGGCGGT   1860

TCTGAGGGTG GCGGTTCTGA GGGTGGCGGT ACTAAACCTC CTGAGTACGG TGATACACCT   1920

ATTCCGGGCT ATACTTATAT CAACCCTCTC GACGGCACTT ATCCGCCTGG TACTGAGCAA   1980

AACCCCGCTA ATCCTAATCC TTCTCTTGAG GAGTCTCAGC CTCTTAATAC TTTCATGTTT   2040

CAGAATAATA GGTTCCGAAA TAGGCAGGGG GCATTAACTG TTTATACGGG CACTGTTACT   2100

CAAGGCACTG ACCCCGTTAA AACTTATTAC CAGTACACTC CTGTATCATC AAAAGCCATG   2160

TATGACGCTT ACTGGAACGG TAAATTCAGA GACTGCGCTT TCCATTCTGG CTTTAATGAA   2220

GATCCATTCG TTTGTGAATA TCAAGGCCAA TCGTCTGACC TGCCTCAACC TCCTGTCAAT   2280

GCTGGCGGCG GCTCTGGTGG TGGTTCTGGT GGCGGCTCTG AGGGTGGTGG CTCTGAGGGT   2340

GGCGGTTCTG AGGGTGGCGG CTCTGAGGGA GGCGGTTCCG GTGGTGGCTC TGGTTCCGGT   2400

GATTTTGATT ATGAAAAGAT GGCAAACGCT AATAAGGGGG CTATGACCGA AAATGCCGAT   2460

GAAAACGCGC TACAGTCTGA CGCTAAAGGC AAACTTGATT CTGTCGCTAC TGATTACGGT   2520

GCTGCTATCG ATGGTTTCAT TGGTGACGTT TCCGGCCTTG CTAATGGTAA TGGTGCTACT   2580

GGTGATTTTG CTGGCTCTAA TTCCCAAATG GCTCAAGTCG GTGACGGTGA TAATTCACCT   2640

TTAATGAATA ATTTCCGTCA ATATTTACCT TCCCTCCCTC AATCGGTTGA ATGTCGCCCT   2700

TTTGTCTTTA GCGCTGGTAA ACCATATGAA TTTTCTATTG ATTGTGACAA AATAAACTTA   2760

TTCCGTGGTG TCTTTGCGTT TCTTTTATAT GTTGCCACCT TTATGTATGT ATTTTCTACG   2820

TTTGCTAACA TACTGCGTAA TAAGGAGTCT TAATCATGCC AGTTCTTTTG GGTATTCCGT   2880

TATTATTGCG TTTCCTCGGT TTCCTTCTGG TAACTTTGTT CGGCTATCTG CTTACTTTTC   2940
```

-continued

```
TTAAAAAGGG CTTCGGTAAG ATAGCTATTG CTATTTCATT GTTTCTTGCT CTTATTATTG   3000
GGCTTAACTC AATTCTTGTG GGTTATCTCT CTGATATTAG CGCTCAATTA CCCTCTGACT   3060
TTGTTCAGGG TGTTCAGTTA ATTCTCCCGT CTAATGCGCT TCCCTGTTTT TATGTTATTC   3120
TCTCTGTAAA GGCTGCTATT TTCATTTTTG ACGTTAAACA AAAAATCGTT TCTTATTTGG   3180
ATTGGGATAA ATAATATGGC TGTTTATTTT GTAACTGGCA AATTAGGCTC TGGAAAGACG   3240
CTCGTTAGCG TTGGTAAGAT TCAGGATAAA ATTGTAGCTG GGTGCAAAAT AGCAACTAAT   3300
CTTGATTTAA GGCTTCAAAA CCTCCCGCAA GTCGGGAGGT TCGCTAAAAC GCCTCGCGTT   3360
CTTAGAATAC CGGATAAGCC TTCTATATCT GATTTGCTTG CTATTGGGCG CGGTAATGAT   3420
TCCTACGATG AAAATAAAAA CGGCTTGCTT GTTCTCGATG AGTGCGGTAC TTGGTTTAAT   3480
ACCCGTTCTT GGAATGATAA GGAAAGACAG CCGATTATTG ATTGGTTTCT ACATGCTCGT   3540
AAATTAGGAT GGGATATTAT TTTTCTTGTT CAGGACTTAT CTATTGTTGA TAAACAGGCG   3600
CGTTCTGCAT TAGCTGAACA TGTTGTTTAT TGTCGTCGTC TGGACAGAAT TACTTTACCT   3660
TTTGTCGGTA CTTTATATTC TCTTATTACT GGCTCGAAAA TGCCTCTGCC TAAATTACAT   3720
GTTGGCGTTG TTAAATATGG CGATTCTCAA TTAAGCCCTA CTGTTGAGCG TTGGCTTTAT   3780
ACTGGTAAGA ATTTGTATAA CGCATATGAT ACTAAACAGG CTTTTTCTAG TAATTATGAT   3840
TCCGGTGTTT ATTCTTATTT AACGCCTTAT TTATCACACG GTCGGTATTT CAAACCATTA   3900
AATTTAGGTC AGAAGATGAA GCTTACTAAA ATATATTTGA AAAAGTTTTC ACGCGTTCTT   3960
TGTCTTGCGA TTGGATTTGC ATCAGCATTT ACATATAGTT ATATAACCCA ACCTAAGCCG   4020
GAGGTTAAAA AGGTAGTCTC TCAGACCTAT GATTTTGATA AATTCACTAT TGACTCTTCT   4080
CAGCGTCTTA ATCTAAGCTA TCGCTATGTT TTCAAGGATT CTAAGGGAAA ATTAATTAAT   4140
AGCGACGATT TACAGAAGCA AGGTTATTCA CTCACATATA TTGATTTATG TACTGTTTCC   4200
ATTAAAAAAG GTAATTCAAA TGAAATTGTT AAATGTAATT AATTTTGTTT TCTTGATGTT   4260
TGTTTCATCA TCTTCTTTTG CTCAGGTAAT TGAAATGAAT AATTCGCCTC TGCGCGATTT   4320
TGTAACTTGG TATTCAAAGC AATCAGGCGA ATCCGTTATT GTTTCTCCCG ATGTAAAAGG   4380
TACTGTTACT GTATATTCAT CTGACGTTAA ACCTGAAAAT CTACGCAATT TCTTTATTTC   4440
TGTTTTACGT GCTAATAATT TTGATATGGT TGGTTCAATT CCTTCCATAA TTCAGAAGTA   4500
TAATCCAAAC AATCAGGATT ATATTGATGA ATTGCCATCA TCTGATAATC AGGAATATGA   4560
TGATAATTCC GCTCCTTCTG GTGGTTTCTT TGTTCCGCAA AATGATAATG TTACTCAAAC   4620
TTTTAAAATT AATAACGTTC GGGCAAAGGA TTTAATACGA GTTGTCGAAT TGTTTGTAAA   4680
GTCTAATACT TCTAAATCCT CAAATGTATT ATCTATTGAC GGCTCTAATC TATTAGTTGT   4740
TAGTGCACCT AAAGATATTT TAGATAACCT TCCTCAATTC CTTTCTACTG TTGATTTGCC   4800
AACTGACCAG ATATTGATTG AGGGTTTGAT ATTTGAGGTT CAGCAAGGTG ATGCTTTAGA   4860
TTTTTCATTT GCTGCTGGCT CTCAGCGTGG CACTGTTGCA GGCGGTGTTA ATACTGACCG   4920
CCTCACCTCT GTTTTATCTT CTGCTGGTGG TTCGTTCGGT ATTTTTAATG GCGATGTTTT   4980
AGGGCTATCA GTTCGCGCAT TAAAGACTAA TAGCCATTCA AAAATATTGT CTGTGCCACG   5040
TATTCTTACG CTTTCAGGTC AGAAGGGTTC TATCTCTGTT GGCCAGAATG TCCCTTTTAT   5100
TACTGGTCGT GTGACTGGTG AATCTGCCAA TGTAAATAAT CCATTTCAGA CGATTGAGCG   5160
TCAAAATGTA GGTATTTCCA TGAGCGTTTT CCTGTTGCA ATGGCTGGCG GTAATATTGT   5220
TCTGGATATT ACCAGCAAGG CCGATAGTTT GAGTTCTTCT ACTCAGGCAA GTGATGTTAT   5280
```

```
TACTAATCAA AGAAGTATTG CTACAACGGT TAATTTGCGT GATGGACAGA CTCTTTTACT      5340

CGGTGGCCTC ACTGATTATA AAAACACTTC TCAAGATTCT GGCGTACCGT TCCTGTCTAA      5400

AATCCCTTTA ATCGGCCTCC TGTTTAGCTC CCGCTCTGAT TCCAACGAGG AAAGCACGTT      5460

ATACGTGCTC GTCAAAGCAA CCATAGTACG CGCCCTGTAG CGGCGCATTA AGCGCGGCGG      5520

GTGTGGTGGT TACGCGCAGC GTGACCGCTA CACTTGCCAG CGCCCTAGCG CCCGCTCCTT      5580

TCGCTTTCTT CCCTTCCTTT CTCGCCACGT TCGCCGGCTT TCCCCGTCAA GCTCTAAATC      5640

GGGGGCTCCC TTTAGGGTTC CGATTTAGTG CTTTACGGCA CCTCGACCCC AAAAAACTTG      5700

ATTTGGGTGA TGGTTCACGT AGTGGGCCAT CGCCCTGATA GACGGTTTTT CGCCCTTTGA      5760

CGTTGGAGTC CACGTTCTTT AATAGTGGAC TCTTGTTCCA AACTGGAACA ACACTCAACC      5820

CTATCTCGGG CTATTCTTTT GATTTATAAG GGATTTTGCC GATTTCGGAA CCACCATCAA      5880

ACAGGATTTT CGCCTGCTGG GGCAAACCAG CGTGGACCGC TTGCTGCAAC TCTCTCAGGG      5940

CCAGGCGGTG AAGGGCAATC AGCTGTTGCC CGTCTCGCTG GTGAAAAGAA AAACCACCCT      6000

GGCGCCCAAT ACGCAAACCG CCTCTCCCCG CGCGTTGGCC GATTCATTAA TGCAGCTGGC      6060

ACGACAGGTT TCCCGACTGG AAAGCGGGCA GTGAGCGCAA CGCAATTAAT GTGAGTTAGC      6120

TCACTCATTA GGCACCCCAG GCTTTACACT TTATGCTTCC GGCTCGTATG TTGTGTGGAA      6180

TTGTGAGCGG ATAACAATTT CACACGCCAA GGAGACAGTC ATAATGAAAT ACCTATTGCC      6240

TACGGCAGCC GCTGGATTGT TATTACTCGC TGCCCAACCA GCCATGGCCG AGCTCTTCCC      6300

GCCATCTGAT GAGCAGTTGA AATCTGGAAC TGCCTCTGTT GTGTGCCTGC TGAATAACTT      6360

CTATCCCAGA GAGGCCAAAG TACAGTGGAA GGTGGATAAC GCCCTCCAAT CGGGTAACTC      6420

CCAGGAGAGT GTCACAGAGC AGGACAGCAA GGACAGCACC TACAGCCTCA GCAGCACCCT      6480

GACGCTGAGC AAAGCAGACT ACGAGAAACA CAAAGTCTAC GCCTGCGAAG TCACCCATCA      6540

GGGCCTGAGC TCGCCCGTCA CAAAGAGCTT CAACAGGGGA GAGTGTTCTA GAACGCGTCA      6600

CTTGGCACTG GCCGTCGTTT TACAACGTCG TGACTGGGAA AACCCTGGCG TTACCCAAGC      6660

TTTGTACATG GAGAAAATAA AGTGAAACAA AGCACTATTG CACTGGCACT CTTACCGTTA      6720

CTGTTTACCC CTGTGGCAAA AGCCGCCTCC ACCAAGGGCC CATCGGTCTT CCCCCTGGCA      6780

CCCTCCTCCA AGAGCACCTC TGGGGGCACA GCGGCCCTGG GCTGCCTGGT CAAGACTAAT      6840

TCCCCGAACC GGTGACGGTG TCGTGGAACT CAGGCGCCCT GACCAGCGGC GTGCACACCT      6900

TCCCGGCTGT CCTACAGTCC TCAGGACTCT ACTCCCTCAG CAGCGTGGTG ACCGTGCCCT      6960

CCAGCAGCTT GGGCACCCAG ACCTACATCT GCAACGTGAA TCACAAGCCC AGCAACACCA      7020

AGGTGGACAA GAAAGCAGAG CCCAAATCTT GTACTAGTGG ATCCTACCCG TACGACGTTC      7080

CGGACTACGC TTCTTAGGCT GAAGGCGATG ACCCTGCTAA GGCTGCATTC AATAGTTTAC      7140

AGGCAAGTGC TACTGAGTAC ATTGGCTACG CTTGGGCTAT GGTAGTAGTT ATAGTTGGTG      7200

CTACCATAGG GATTAAATTA TTCAAAAAGT TTACGAGCAA GGCTTCTTAA GCAATAGCGA      7260

AGAGGCCCGC ACCGATCGCC CTTCCCAACA GTTGCGCAGC CTGAATGGCG AATGGCGCTT      7320

TGCCTGGTTT CCGGCACCAG AAGCGGTGCC GGAAAGCTGG CTGGAGTGCG ATCTTCCTGA      7380

GGCCGATACG GTCGTCGTCC CCTCAAACTG GCAGATGCAC GGTTACGATG CGCCCATCTA      7440

CACCAACGTA ACCTATCCCA TTACGGTCAA TCCGCCGTTT GTTCCCACGG AGAATCCGAC      7500

GGGTTGTTAC TCGCTCACAT TTAATGTTGA TGAAAGCTGG CTACAGGAAG GCCAGACGCG      7560

AATTATTTTT GATGGCGTTC CTATTGGTTA AAAAATGAGC TGATTTAACA AAAATTTAAC      7620

GCGAATTTTA ACAAAATATT AACGTTTACA ATTTAAATAT TTGCTTATAC AATCTTCCTG      7680
```

```
TTTTTGGGGC TTTTCTGATT ATCAACCGGG GTACATATGA TTGACATGCT AGTTTTACGA      7740

TTACCGTTCA TCGATTCTCT TGTTTGCTCC AGACTCTCAG GCAATGACCT GATAGCCTTT      7800

GTAGATCTCT CAAAAATAGC TACCCTCTCC GGCATTAATT TATCAGCTAG AACGGTTGAA      7860

TATCATATTG ATGGTGATTT GACTGTCTCC GGCCTTTCTC ACCCTTTTGA ATCTTTACCT      7920

ACACATTACT CAGGCATTGC ATTTAAAATA TATGAGGGTT CTAAAAATTT TTATCCTTGC      7980

GTTGAAATAA AGGCTTCTCC CGCAAAAGTA TTACAGGGTC ATAATGTTTT TGGTACAACC      8040

GATTTAGCTT TATGCTCTGA GGCTTTATTG CTTAATTTTG CTAATTCTTT GCCTTGCCTG      8100

TATGATTTAT TGGACGTT                                                    8118

(2) INFORMATION FOR SEQ ID NO:6:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ix) FEATURE:
        (A) NAME/KEY: misc_difference
        (B) LOCATION: replace(5, "")
        (D) OTHER INFORMATION: /note= "S REPRESENTS EQUAL MIXTURE
            OF G AND C"

(ix) FEATURE:
        (A) NAME/KEY: misc_difference
        (B) LOCATION: replace(6, "")
        (D) OTHER INFORMATION: /note= "M REPRESENTS EQUAL MIXTURE
            OF A AND C"

(ix) FEATURE:
        (A) NAME/KEY: misc_difference
        (B) LOCATION: replace(8, "")
        (D) OTHER INFORMATION: /note= "R REPRESENTS EQUAL MIXTURE
            OF A AND G"

(ix) FEATURE:
        (A) NAME/KEY: misc_difference
        (B) LOCATION: replace(11, "")
        (D) OTHER INFORMATION: /note= "K REPRESENTS EQUAL MIXTURE
            OF G AND T"

(ix) FEATURE:
        (A) NAME/KEY: misc_difference
        (B) LOCATION: replace(20, "")
        (D) OTHER INFORMATION: /note= "W REPRESENTS EQUAL MIXTURE
            OF A AND T"

(xi) SEQUENCE DESCRIPTION: SEQ ID NO:6:

AGGTSMARCT KCTCGAGTCW GG                                               22

(2) INFORMATION FOR SEQ ID NO:7:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:7:

AGGTCCAGCT GCTCGAGTCT GG                                               22

(2) INFORMATION FOR SEQ ID NO:8:

(i) SEQUENCE CHARACTERISTICS:
        (A) LENGTH: 22 base pairs
        (B) TYPE: nucleic acid
```

```
        (C) STRANDEDNESS: single
        (D) TOPOLOGY: linear (xi) SEQUENCE DESCRIPTION: SEQ ID NO:8:

AGGTCCAGCT GCTCGAGTCA GG                                              22

(2) INFORMATION FOR SEQ ID NO:9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:9:

AGGTCCAGCT TCTCGAGTCT GG                                              22

(2) INFORMATION FOR SEQ ID NO:10:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:10:

AGGTCCAGCT TCTCGAGTCA GG                                              22

(2) INFORMATION FOR SEQ ID NO:11:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:11:

AGGTCCAACT GCTCGAGTCT GG                                              22

(2) INFORMATION FOR SEQ ID NO:12:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:12:

AGGTCCAACT GCTCGAGTCA GG                                              22

(2) INFORMATION FOR SEQ ID NO:13:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:13:

AGGTCCAACT TCTCGAGTCT GG                                              22

(2) INFORMATION FOR SEQ ID NO:14:

(i) SEQUENCE CHARACTERISTICS:
        (A) LENGTH: 22 base pairs
        (B) TYPE: nucleic acid
        (C) STRANDEDNESS: single
```

(D) TOPOLOGY: linear (xi) SEQUENCE DESCRIPTION: SEQ ID NO:14:

AGGTCCAACT TCTCGAGTCA GG                                           22

(2) INFORMATION FOR SEQ ID NO:15:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ix) FEATURE:
        (A) NAME/KEY: misc_difference
        (B) LOCATION: replace(5..6, "")
        (D) OTHER INFORMATION: /note= "N=INOSINE"

(ix) FEATURE:
        (A) NAME/KEY: misc_difference
        (B) LOCATION: replace(8, "")
        (D) OTHER INFORMATION: /note= "N=INOSINE"

(ix) FEATURE:
        (A) NAME/KEY: misc_difference
        (B) LOCATION: replace(11, "")
        (D) OTHER INFORMATION: /note= "N=INOSINE"

(ix) FEATURE:
        (A) NAME/KEY: misc_difference
        (B) LOCATION: replace(20, "")
        (D) OTHER INFORMATION: /note= "W REPRESENTS EQUAL MIXTURE
            OF A AND T"

(xi) SEQUENCE DESCRIPTION: SEQ ID NO:15:

AGGTNNANCT NCTCGAGTCW GG                                           22

(2) INFORMATION FOR SEQ ID NO:16:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:16:

CTATTAACTA GTAACGGTAA CAGTGGTGCC TTGCCCCA                           38

(2) INFORMATION FOR SEQ ID NO:17:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:17:

AGGCTTACTA GTACAATCCC TGGGCACAAT                                    30

(2) INFORMATION FOR SEQ ID NO:18:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:18:

CCAGTTCCGA GCTCGTTGTG ACTCAGGAAT CT                                 32

(2) INFORMATION FOR SEQ ID NO:19:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:19:

CCAGTTCCGA GCTCGTGTTG ACGCAGCCGC CC                        32

(2) INFORMATION FOR SEQ ID NO:20:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:20:

CCAGTTCCGA GCTCGTGCTC ACCCAGTCTC CA                        32

(2) INFORMATION FOR SEQ ID NO:21:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:21:

CCAGTTCCGA GCTCCAGATG ACCCAGTCTC CA                        32

(2) INFORMATION FOR SEQ ID NO:22:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:22:

CCAGATGTGA GCTCGTGATG ACCCAGACTC CA                        32

(2) INFORMATION FOR SEQ ID NO:23:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:23:

CCAGATGTGA GCTCGTCATG ACCCAGTCTC CA                        32

(2) INFORMATION FOR SEQ ID NO:24:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:24:

CCAGTTCCGA GCTCGTGATG ACACAGTCTC CA                        32

(2) INFORMATION FOR SEQ ID NO:25:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:25:

GCAGCATTCT AGAGTTTCAG CTCCAGCTTG CC                                        32

(2) INFORMATION FOR SEQ ID NO:26:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:26:

GCGCCGTCTA GAATTAACAC TCATTCCTGT TGAA                                  34

(2) INFORMATION FOR SEQ ID NO:27:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:27:

GATCCTAGGC TGAAGGCGAT GACCCTGCTA AGGCTGC                             37

(2) INFORMATION FOR SEQ ID NO:28:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:28:

ATTCAATAGT TTACAGGCAA GTGCTACTGA GTACA                                35

(2) INFORMATION FOR SEQ ID NO:29:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:29:

TTGGCTACGC TTGGGCTATG GTAGTAGTTA TAGTT                                35

(2) INFORMATION FOR SEQ ID NO:30:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:30:

GGTGCTACCA TAGGGATTAA ATTATTCAAA AAGTT                                35

(2) INFORMATION FOR SEQ ID NO:31:

```
    (i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:31:

TACGAGCAAG GCTTCTTA                                                  18

(2) INFORMATION FOR SEQ ID NO:32:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:32:

AGCTTAAGAA GCCTTGCTCG TAAACTTTTT GAATAATTT                           39

(2) INFORMATION FOR SEQ ID NO:33:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:33:

AATCCCTATG GTAGCACCAA CTATAACTAC TACCAT                              36

(2) INFORMATION FOR SEQ ID NO:34:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:34:

AGCCCAAGCG TAGCCAATGT ACTCAGTAGC ACTTG                               35

(2) INFORMATION FOR SEQ ID NO:35:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:35:

CCTGTAAACT ATTGAATGCA GCCTTAGCAG GGTC                                34

(2) INFORMATION FOR SEQ ID NO:36:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:36:

ATCGCCTTCA GCCTAG                                                    16

(2) INFORMATION FOR SEQ ID NO:37:
```

(i) SEQUENCE CHARACTERISTICS:
    (A) LENGTH: 21 base pairs
    (B) TYPE: nucleic acid
    (C) STRANDEDNESS: single
    (D) TOPOLOGY: linear (xi) SEQUENCE DESCRIPTION: SEQ ID NO:37:

CATTTTTGCA GATGGCTTAG A          21

(2) INFORMATION FOR SEQ ID NO:38:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:38:

TAGCATTAAC GTCCAATA          18

(2) INFORMATION FOR SEQ ID NO:39:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:39:

ATATATTTTA GTAAGCTTCA TCTTCT          26

(2) INFORMATION FOR SEQ ID NO:40:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:40:

GACAAAGAAC GCGTGAAAAC TTT          23

(2) INFORMATION FOR SEQ ID NO:41:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:41:

GCGGGCCTCT TCGCTATTGC TTAAGAAGCC TTGCT          35

(2) INFORMATION FOR SEQ ID NO:42:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (xi) SEQUENCE DESCRIPTION: SEQ ID NO:42:

AAACGACGGC CAGTGCCAAG TGACGCGTGT GAAATTGTTA TCC          43

(2) INFORMATION FOR SEQ ID NO:43:

(i) SEQUENCE CHARACTERISTICS:

(A) LENGTH: 43 base pairs
(B) TYPE: nucleic acid
(C) STRANDEDNESS: single
(D) TOPOLOGY: linear (xi) SEQUENCE DESCRIPTION: SEQ ID NO:43:

GGCGAAAGGG AATTCTGCAA GGCGATTAAG CTTGGGTAAC GCC        43

(2) INFORMATION FOR SEQ ID NO:44:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:44:

GGCGTTACCC AAGCTTTGTA CATGGAGAAA ATAAAG        36

(2) INFORMATION FOR SEQ ID NO:45:

(i) SEQUENCE CHARACTERISTICS:
(A) LENGTH: 42 base pairs
(B) TYPE: nucleic acid
(C) STRANDEDNESS: single
(D) TOPOLOGY: linear (xi) SEQUENCE DESCRIPTION: SEQ ID NO:45:

TGAAACAAAG CACTATTGCA CTGGCACTCT TACCGTTACC GT        42

(2) INFORMATION FOR SEQ ID NO:46:

(i) SEQUENCE CHARACTERISTICS:
(A) LENGTH: 42 base pairs
(B) TYPE: nucleic acid
(C) STRANDEDNESS: single
(D) TOPOLOGY: linear (xi) SEQUENCE DESCRIPTION: SEQ ID NO:46:

TACTGTTTAC CCCTGTGACA AAAGCCGCCC AGGTCCAGCT GC        42

(2) INFORMATION FOR SEQ ID NO:47:

(i) SEQUENCE CHARACTERISTICS:
(A) LENGTH: 44 base pairs
(B) TYPE: nucleic acid
(C) STRANDEDNESS: single
(D) TOPOLOGY: linear (xi) SEQUENCE DESCRIPTION: SEQ ID NO:47:

TCGAGTCAGG CCTATTGTGC CCAGGGATTG TACTAGTGGA TCCG        44

(2) INFORMATION FOR SEQ ID NO:48:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:48:

TGGCGAAAGG GAATTCGGAT CCACTAGTAC AATCCCTG        38

(2) INFORMATION FOR SEQ ID NO:49:

(i) SEQUENCE CHARACTERISTICS:
(A) LENGTH: 42 base pairs

```
            (B) TYPE: nucleic acid
            (C) STRANDEDNESS: single
            (D) TOPOLOGY: linear (xi) SEQUENCE DESCRIPTION: SEQ ID NO:49:

GGCACAATAG GCCTGACTCG AGCAGCTGGA CCAGGGCGGC TT                    42

(2) INFORMATION FOR SEQ ID NO:50:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (xi) SEQUENCE DESCRIPTION: SEQ ID NO:50:

TTGTCACAGG GGTAAACAGT AACGGTAACG GTAAGTGTGC CA                    42

(2) INFORMATION FOR SEQ ID NO:51:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (xi) SEQUENCE DESCRIPTION: SEQ ID NO:51:

GTGCAATAGT GCTTTGTTTC ACTTTATTTT CTCCATGTAC AA                    42

(2) INFORMATION FOR SEQ ID NO:52:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:52:

TAACGGTAAG AGTGCCAGTG C                                           21

(2) INFORMATION FOR SEQ ID NO:53:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (xi) SEQUENCE DESCRIPTION: SEQ ID NO:53:

CACCTTCATG AATTCGGCAA GGAGACAGTC AT                               32

(2) INFORMATION FOR SEQ ID NO:54:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (xi) SEQUENCE DESCRIPTION: SEQ ID NO:54:

AATTCGCCAA GGAGACAGTC AT                                          22

(2) INFORMATION FOR SEQ ID NO:55:

(i) SEQUENCE CHARACTERISTICS:
            (A) LENGTH: 39 base pairs
            (B) TYPE: nucleic acid
```

```
        (C) STRANDEDNESS: single
        (D) TOPOLOGY: linear (xi) SEQUENCE DESCRIPTION: SEQ ID NO:55:

AATGAAATAC CTATTGCCTA CGGCAGCCGC TGGATTGTT                              39

(2) INFORMATION FOR SEQ ID NO:56:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:56:

ATTACTCGCT GCCCAACCAG CCATGGCCGA GCTCGTGAT                              39

(2) INFORMATION FOR SEQ ID NO:57:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:57:

GACCCAGACT CCAGATATCC AACAGGAATG AGTGTTAAT                              39

(2) INFORMATION FOR SEQ ID NO:58:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (xi) SEQUENCE DESCRIPTION: SEQ ID NO:58:

TCTAGAACGC GTC                                                          13

(2) INFORMATION FOR SEQ ID NO:59:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO:59:

TTCAGGTTGA AGCTTACGCG TTCTAGAATT AACACTCATT CCTGT                       45

(2) INFORMATION FOR SEQ ID NO:60:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:60:

TGGATATCTG GAGTCTGGGT CATCACGAGC TCGGCCATG                              39

(2) INFORMATION FOR SEQ ID NO:61:

(i) SEQUENCE CHARACTERISTICS:
        (A) LENGTH: 39 base pairs
        (B) TYPE: nucleic acid
        (C) STRANDEDNESS: single
```

(D) TOPOLOGY: linear (xi) SEQUENCE DESCRIPTION: SEQ ID NO:61:

GCTGGTTGGG CAGCGAGTAA TAACAATCCA GCGGCTGCC                          39

(2) INFORMATION FOR SEQ ID NO:62:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:62:

GTAGGCAATA GGTATTTCAT TATGACTGTC CTTGGCG                            37

(2) INFORMATION FOR SEQ ID NO:63:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:63:

TGACTGTCTC CTTGGCGTGT GAAATTGTTA                                    30

(2) INFORMATION FOR SEQ ID NO:64:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:64:

TAACACTCAT TCCGGATGGA ATTCTGGAGT CTGGGT                             36

(2) INFORMATION FOR SEQ ID NO:65:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:65:

GCCAGTGCCA AGTGACGCGT TCTA                                          24

(2) INFORMATION FOR SEQ ID NO:66:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:66:

ATATATTTTA GTAAGCTTCA TCTTCT                                        26

(2) INFORMATION FOR SEQ ID NO:67:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:67:

GACAAAGAAC GCGTGAAAAC TTT                                                23

(2) INFORMATION FOR SEQ ID NO:68:

(i) SEQUENCE CHARACTERISTICS:
         (A) LENGTH: 76 base pairs
         (B) TYPE: nucleic acid
         (C) STRANDEDNESS: single
         (D) TOPOLOGY: linear (xi) SEQUENCE DESCRIPTION: SEQ ID NO:68:

CTGAACCTGT CTGGGACCAC AGTTGATGCT ATAGGATCAG ATCTAGAATT CATTTAGAGA        60

CTGGCCTGGC TTCTGC                                                        76

(2) INFORMATION FOR SEQ ID NO:69:

(i) SEQUENCE CHARACTERISTICS:
         (A) LENGTH: 80 base pairs
         (B) TYPE: nucleic acid
         (C) STRANDEDNESS: single
         (D) TOPOLOGY: linear (xi) SEQUENCE DESCRIPTION: SEQ ID NO:69:

TCGACCGTTG GTAGGAATAA TGCAATTAAT GGAGTAGCTC TAAATTCAGA ATTCATCTAC        60

ACCCAGTGCA TCCAGTAGCT                                                    80

(2) INFORMATION FOR SEQ ID NO:70:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (xi) SEQUENCE DESCRIPTION: SEQ ID NO:70:

GGTAAACAGT AACGGTAAGA GTGCCAG                                            27

(2) INFORMATION FOR SEQ ID NO:71:

(i) SEQUENCE CHARACTERISTICS:
         (A) LENGTH: 54 base pairs
         (B) TYPE: nucleic acid
         (C) STRANDEDNESS: single
         (D) TOPOLOGY: linear (xi) SEQUENCE DESCRIPTION: SEQ ID NO:71:

CGCCTTCAGC CTAAGAAGCG TAGTCCGGAA CGTCGTACGG GTAGGATCCA CTAG              54

(2) INFORMATION FOR SEQ ID NO:72:

(i) SEQUENCE CHARACTERISTICS:
         (A) LENGTH: 41 base pairs
         (B) TYPE: nucleic acid
         (C) STRANDEDNESS: single
         (D) TOPOLOGY: linear (xi) SEQUENCE DESCRIPTION: SEQ ID NO:72:

CACCGGTTCG GGAATTAGT CTTGACCAGG CAGCCCAGGG C                             41

(2) INFORMATION FOR SEQ ID NO:73:

(i) SEQUENCE CHARACTERISTICS:
         (A) LENGTH: 51 base pairs

-continued

```
        (B)  TYPE: nucleic acid
        (C)  STRANDEDNESS: single
        (D)  TOPOLOGY: linear (xi) SEQUENCE DESCRIPTION: SEQ ID NO:73:

ATTCCACACA TTATACGAGC CGGAAGCATA AAGTGTCAAG CCTGGGGTGC C                51

(2) INFORMATION FOR SEQ ID NO:74:

(i) SEQUENCE CHARACTERISTICS:
        (A)  LENGTH: 42 base pairs
        (B)  TYPE: nucleic acid
        (C)  STRANDEDNESS: single
        (D)  TOPOLOGY: linear (xi) SEQUENCE DESCRIPTION: SEQ ID NO:74:

CTGCTCATCA GATGGCGGGA AGAGCTCGGC CATGGCTGGT TG                          42

(2) INFORMATION FOR SEQ ID NO:75:

(i) SEQUENCE CHARACTERISTICS:
        (A)  LENGTH: 42 base pairs
        (B)  TYPE: nucleic acid
        (C)  STRANDEDNESS: single
        (D)  TOPOLOGY: linear (xi) SEQUENCE DESCRIPTION: SEQ ID NO:75:

GAACAGAGTG ACCGAGGGGG CGAGCTCGGC CATGGCTGGT TG                          42

(2) INFORMATION FOR SEQ ID NO:76:

(i) SEQUENCE CHARACTERISTICS:
        (A)  LENGTH: 19 base pairs
        (B)  TYPE: nucleic acid
        (C)  STRANDEDNESS: single
        (D)  TOPOLOGY: linear (ii) MOLECULE TYPE: cDNA (xi) SEQUENCE DESCRIPTION: SEQ ID NO:76:

GGGCTTTTGC CACAGGGGT                                                    19
```